(12) United States Patent
Frank et al.

(10) Patent No.: US 8,642,775 B2
(45) Date of Patent: Feb. 4, 2014

(54) VANILLOID RECEPTOR LIGANDS, PHARMACEUTICAL COMPOSITIONS CONTAINING THEM, PROCESS FOR MAKING THEM, AND USE THEREOF FOR TREATING PAIN AND OTHER CONDITIONS

(75) Inventors: Robert Frank, Aachen (DE); Gregor Bahrenberg, Aachen (DE); Thomas Christoph, Aachen (DE); Klaus Schiene, Juechen (DE); Jean De Vry, Stolberg (DE); Derek Saunders, Aachen (DE); Michael Przewosny, Aachen (DK); Bernd Sundermann, Friedrichsdorf (DE); Jewoo Lee, Gyenggi-Do (KR)

(73) Assignee: Gruenenthal GmbH, Aachen (DE)

( * ) Notice: Subject to any disclaimer, the term of this patent is extended or adjusted under 35 U.S.C. 154(b) by 150 days.

(21) Appl. No.: 12/103,198

(22) Filed: Apr. 15, 2008

(65) Prior Publication Data

US 2008/0262039 A1     Oct. 23, 2008

(30) Foreign Application Priority Data

Apr. 16, 2007 (DE) .......................... 10 2007 018 151

(51) Int. Cl.
*C07D 213/62* (2006.01)
*A61K 31/44* (2006.01)

(52) U.S. Cl.
USPC ........................................ 546/300; 514/357

(58) Field of Classification Search
USPC ....................................................... 546/300
See application file for complete search history.

(56) References Cited

U.S. PATENT DOCUMENTS

| | | | |
|---|---|---|---|
| 6,630,495 B1 * | 10/2003 | Cooke et al. | 514/357 |
| 6,821,992 B1 * | 11/2004 | Cooke et al. | 514/336 |
| 7,135,493 B2 | 11/2006 | Urano et al. | |
| 2004/0229889 A1 | 11/2004 | Urano et al. | |
| 2005/0107619 A1 | 5/2005 | Grammenos et al. | |

FOREIGN PATENT DOCUMENTS

| | | |
|---|---|---|
| EP | 1 403 235 A | 3/2004 |
| JP | 2003-506465 A5 | 2/2003 |
| JP | 2003-506466 A1 | 2/2003 |
| JP | 2006-518341 A | 8/2006 |
| JP | 2006-526660 A | 11/2006 |
| JP | 2007-501246 A | 1/2007 |
| WO | WO 01/11965 A | 2/2001 |
| WO | WO 01/11966 A | 2/2001 |
| WO | WO 02/100819 A1 | 12/2002 |
| WO | WO 03/076392 A2 | 9/2003 |
| WO | WO 03/076406 A1 | 9/2003 |
| WO | WO 2004/063169 A1 | 7/2004 |
| WO | WO 2004/108133 A2 | 12/2004 |
| WO | WO 2005/016890 A1 | 2/2005 |
| WO | WO 2005/073193 A1 | 8/2005 |
| WO | WO 2005/080324 A1 | 9/2005 |
| WO | WO 2007/039114 A | 4/2007 |

OTHER PUBLICATIONS

DiMarzo, V. et al. "Brain TRPV1: a depressing TR(i)P down memory lane?" Trends in Pharmacological Sciences, 2008, vol. 29 (12), 594-600.*
Malmberg, A and Riley, K., eds, Turning Up the Heat on Pain: TRPV1Receptors in Pain and Inflammation, 2005, Verlag Basel, pp. 58, 65, 171, 172, 179-180, 197.*
Sigma-Aldrich online catalog screen shots from http://www.sigmaaldrich.com, accessed Aug. 31, 2010.*
Patani, G., Chem. Rev. 1996, vol. 96, pp. 3147-3176.*
International Search Report mailed Dec. 5, 2008, with English translation, ten (10) pages.
International Preliminary Report on Patentability mailed Nov. 19, 2009, with English translation, twelve (12) pages.
Database Registry, Chemical Abstracts Service, Columbus, Ohio. Jul. 29, 2001, XP002486939, CAS RN: 349411-19-4.
Database Registry, Chemical Abstracts Service, Columbus, Ohio. Oct. 8, 2001, XP002486940, CAS RN: 360770-08-7.
Database Registry, Chemical Abstracts Service, Columbus, Ohio. May 26, 2006, XP002486941, CAS RN: 885662-85-1.
G. Ahern, Activation of TRPV1 by the Satiety Factor Oleoylethanolamide, The Journal of Biological Chemistry, vol. 278, No. 33, Aug. 15, pp. 30429-30434, 2003.
L.A. Birder et al., Altered urinary bladder function in mice lacking the vanilloid receptor TRPV1, Nature Neuroscience, vol. 5, No. 9, Sep. 2002, pp. 856-860.
E. Bodo et al., A Hot New Twist to Hair Biology: Involvement of Vanilloid Receptor-1 (VR1/TRPV1) Signaling in Human Hair Growth Control, American Journal of Pathology, vol. 166, No. 4, Apr. 2005, pp. 985-998.
D. Dawbarn et al., Intranigral Injection of Capsaicin Enhances Motor Activity and Depletes Nigral 5-Hydroxytryptamine But Not Substance P, Neuropharmacology, vol. 20, pp. 341-346, 1981.

(Continued)

*Primary Examiner* — Janet L Andres
*Assistant Examiner* — Heidi Reese
(74) *Attorney, Agent, or Firm* — Crowell & Moring LLP

(57) ABSTRACT

Vanilloid receptor ligand compounds corresponding to formula I:

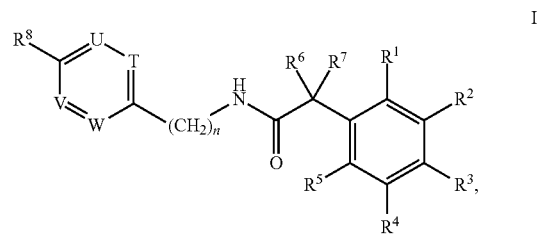

a process for producing such compounds, pharmaceutical compositions containing them, and the use of such compounds to treat pain and various other vanilloid receptor mediated conditions.

28 Claims, No Drawings

(56) References Cited

OTHER PUBLICATIONS

P. Geppetti et al., Activation and sensitisation of the vanilloid receptor: role in gastrointestinal inflammation and function, British Journal of Pharmacology, 2004, vol. 141, No. 8, pp. 1313-1320.
J. Ghilardi et al., Selective Blockade of the Capasicin Receptor TRPV1 Attenuates Bone Cancer Pain, The Journal of Neuroscience, Mar. 23, 2005, vol. 25, No. 12, pp. 3126-3131.
P. Holzer, TRPV1 and the gut: from a tasty receptor for a painful vanilloid to a key player in hyperalgesia, European Journal of Pharmacology 500, 2004, pp. 231-241.
H. Rami et al., The therapeutic potential of TRPV1 (VRI) antagonists: clinical answers await, Drug Discover Today: Therapeutic Strategies, vol. 1, No. 1, 2004, pp. 97-104.
C. Maggi, Therapeutic Potential of Capsaicin-like Molecules: Studies in Animals and Humans, Life Sciences, vol. 51, pp. 1777-1781 1992.
S. Marinelli et al., Presynaptic Facilitation of Glutamatergic Synapses to Dopaminergic Neurons of the Rat Substantia Nigra by Endogenous Stimulation of Vanilloid Receptors, The Journal of Neuroscience, Apr. 15, 2003, vol. 23, No. 8, pp. 3136-3144.
H. Pan et al., Sensing Tissue Ischemia: Another New Function for Capsaicin Receptors?, Circulation Journal of the American Heart Association, Circulation 2004, vol. 110, Issue 13, pp. 1826-1831.
H. Schultz, The spice of life is at the root of cardiac pain, Journal of Physiology (2003), 551.2, p. 400.
Y. Yiangou et al., Vanilloid receptor 1 immunoreactivity in inflamed human bowel, The Lancet, vol. 357, p. 1338-1339, Apr. 28, 2001.
M. Zahner et al., Cardiac vanilloid receptor 1-expressing afferent nerves and their role in the cardiogenic sympathetic reflex in rats, Journal of Physiology (2003) 551.2, pp. 515-523.
T. Sprenger et al., Migraine pathogenesis and state of pharmacological treatment options, BMC Medicine 2009, 7:71.
G.A. Lambert et al., The effects of the TRPV1 receptor antagonist SB-705498 on trigeminovascular sensitisation and neurotransmission, Nauyn-Schmied Arch Pharmacol (2009) vol. 380, pp. 311-325.
R. Planells-Cases et al., Functional aspects and mechanisms of TRPV1 involvement in neurogenic inflammation that leads to thermal hyperalgesia, Pflugers Arch—Eur J. Physiol (2005) vol. 451, pp. 151-159.
V. Micale et al., Altered responses of dopamine D3 receptor null mice to excitotoxic or anxiogenic stimuli: Possible involvement of the endocannabinoid and endovanilloid systems, Neurobiology of Disease 36 (2009), pp. 70-80.
M. Fu et al., TRPV1: A potential target for antiepileptogenesis, Medical Hypotheses 73 (2009), pp. 100-102.
F. Leung, Capsaicin-sensitive intestinal mucosal afferent mechanism and body fat distribution, Life Sciences 83 (2008), pp. 1-5.
A. Suri et al., The emerging role of TRPV1 in diabetes and obesity, TRENDS in Pharmacological Sciences, vol. 29, No. 1, pp. 29-36 (2007).
J. Li et al., Increased GFR and renal excretory function by activation of TRPV in the isolated prefused kidney, Pharmacological Research vol. 57, Issue 3 (2008), pp. 239-246.
M. Ghasemi et al., Effect of anandamide on nonadrenergic noncholinergic-mediated relaxation of rat corpus cavernosum, European Journal of Pharmacology vol. 544, Issues 1-3 (2006), pp. 138-145.
S. Mandadi et al., Locomotor Networks Are Targets of Modulation by Sensory Transient Receptor Potential Vanilloid 1 and Transient Receptor Potential Melastatin 8 Channels, Neuroscience 162 (2009) pp. 1377-1397.
R. Marsch et a., Reduced Anxiety, Conditioned Fear, and Hippocampal Long-Term Potentiation in Transient Receptor Potential Vanilloid Type 1 Receptor-Deficient Mice, The Journal of Neuroscience, Jan. 24, 2007, vol. 27, No. 4, pp. 832-839.
H. Eilers, Anesthetic Activation of Nociceptors: Adding Insult to Injury?, Molecular Interventions, Oct. 2008, vol. 8, Issue 5, pp. 226-229.
Won-Sik Shim et al., TRPV1 Mediates Histamine-Induced Itching via the Activation of Phospolipase $A_2$ and 12-Lipoxygenase, The Journal of Neuroscience, Feb. 28, 2007, vol. 27, No. 9, pp. 2331-2337.
W. Huang, Enhanced postmyocardial infarction fibrosis via stimulation of the transforming growth factor-B-Smad2 signaling pathway: role of transient receptor potential vanilloid type 1 channels, Journal of Hypertension vol. 27 (2009).
I.-J You et al., Society for Neuroscience. Abstract. vol. 912.22 (2007).
Donnerer J. et al., Pharmacology. Feb. 2005; vol. 73, Issue 2, pp. 97-101 (2005). E pub Oct. 18, 2004.
Min Fu et al., TRPV1 : A potential target for antiepileptogenesis, Medical Hypothesis 73 (2009) 100-102.
John J. Adcock, TRPV1 receptors in sensitisation of cough and pain reflexes, Pulmonary Pharmacology & Therapeutics 22 (2009) 65-70.
Teshamae S. Monteith et al., Acute Migraine Therapy: New Drugs and New Approaches, Current Treatment in Neurology (2011) 13:1-14.
Magdalene M. Moran et al., Transient receptor potential channels as therapeutic targets, Nature Reviews, Drug Discovery, vol. 10, Aug. 2011, pp. 601-620.
Celia D. Cruz et al., Intrathecal delivery of resiniferatoxin (RTX) reduces detrusor overactivity and spinal expression of TRPV1 in spinal cord injured animals, Experiemental Neurology 214 (2008) 301-308.
Naoki Yoshimura et al., Therapeutic receptor targets for lower urinary tract dysfunction, Naunyn-Schmiedeberg's Arch Pharmacol (2008) 377:437-448.
Carlos Silva et al., Bladder sensory desensitization decreases urinary urgency, BMC Urology 2007, 7:9.
Klaus Urbahns et al., Naphthol derivatives as TRPV1 inhibitors for the treatment of urinary incontinence, Bioorganic & Medicinal Chemistry Letters 21 (2011) 3354-3357.
CAPLUS, 1995: 347083.
Malmberg et al., "Turning up the Heat on Pain: TRPV1 Receptors in Pain and Inflammation," 2005, contents, pp. 3-22, 55-69, 167-187, 191-209.
Silverman, Richard B., "The Organic Chemistry of Drug Design and Drug Action," $2^{nd}$ edition, 2004, pp. 29-32.
Khimii, 1987, pp. 2538-2544.
Klopman et al., Quantitative structure-agonist activity relationship of capsaicin analogues, The Journal of Computer-Aided Molecular Design, No. 9, 1995, pp. 283-294.
Chemical Abstracts 349411-19-4, 360770-08-7 and 885662-85-1, Registry Chemical Abstracts Service, (two (2) pages), 2006.
Chemical Abstract 1988:528124, (Caplus), (one (1) page).
Aldrich, Catalog Handbook of Chemicals, 1992-1993, p. 260, (two (2) pages).

\* cited by examiner

VANILLOID RECEPTOR LIGANDS, PHARMACEUTICAL COMPOSITIONS CONTAINING THEM, PROCESS FOR MAKING THEM, AND USE THEREOF FOR TREATING PAIN AND OTHER CONDITIONS

The present invention relates to novel vanilloid receptor ligands, to processes for the production thereof, to medicinal drugs containing said compounds and to the use of said compounds for the production of medicinal drugs.

The treatment of pain, particularly neuropathic pain, is of great significance in the medical field. There is a global need for effective pain therapies. The urgent need for action to provide a patient-friendly und targeted treatment of chronic and non-chronic states of pain, this being taken to mean the successful und satisfactory treatment of pain for patients, is documented by the large number of scientific papers which have recently appeared in the field of applied analgesics or in basic research concerning nociception.

A suitable starting point for the treatment of pain; particularly of pain selected from the group consisting of acute pain, chronic pain, neuropathic pain, and visceral pain and more preferably neuropathic pain; is the vanilloid receptor of subtype 1 (VR1/TRPV1), frequently also designated as the capsaicin receptor. This receptor is stimulated, inter alia, by vanilloids such as capsaicin, heat, and protons and plays a central part in the generation of pain. Furthermore, it is significant for a large number of other physiological and pathophysiological processes such as migraine; states of depression; neurodegenerative disorders; cognitive disorders; anxiety; epilepsy; coughing; diarrhea; pruritus; inflammations; disorders of the cardiovascular system; food intake disorders; medicine addiction; medicine abuse and, in particular, urinary incontinence.

It is thus an object of the invention to provide novel compounds which are particularly suitable for use as pharmacologically active substances in medicinal drugs, preferably in medicinal drugs for treatment of disorders or diseases that are at least partially mediated by vanilloid receptors 1 (VR1/TRPV1 receptors). It has now been found, surprisingly, that the substituted compounds of the general formula I stated below show excellent affinity to the vanilloid receptor of subtype 1 (VR1/TRPV1 receptor) and are therefore particularly suitable for the prophylaxis and/or treatment of disorders or diseases which are at least partially mediated by vanilloid receptors 1 (VR1/TRPV1). The substituted compounds corresponding to the following formula I also show anti-inflammatory activity.

It is thus at object of the present invention to provide substituted compounds of the general formula I,

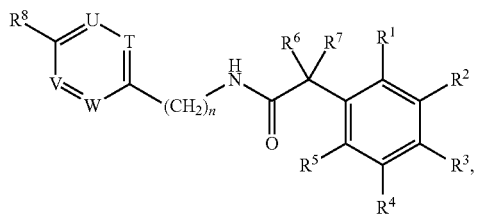

I in which
n stands for 0, 1, 2, 3, or 4;
$R^1$ stands for H; F; Cl; Br; I; —$SF_5$; —$NO_2$; —CN; —$NH_2$; —OH; —SH; —C(=O)—$NH_2$; —S(=O)$_2$—$NH_2$; —C(=O)—NH—OH; —C(=O)—OH; —C(=O)—H; —S(=O)$_2$—OH; —C(=NH)—$NH_2$; —C(=NH)—NH—$R^9$; —N=C($NH_2$)$_2$; —N=C($NHR^{10}$)—($NHR^{11}$); —O—P(=O)$_2$—O—$R^{12}$; —$NHR^{13}$; —$NR^{14}R^{15}$; —NH—C(=O)—$R^{13}$; —$OR^{16}$; —$SR^{17}$; —C(=O)—$NHR^{18}$; —C(=O)—$NR^{19}R^{20}$; —S(=O)$_2$—$NHR^{21}$; —S(=O)$_2$—$NR^{22}R^{23}$; —C(=O)—$OR^{24}$; —C(=O)—$R^{25}$; —S(=O)—$R^{26}$; or —S(=O)$_2$—$R^{27}$ or for a linear or branched, saturated or unsaturated, unsubstituted or at least monosubstituted aliphatic $C_{1-10}$ radical;
$R^2$ stands for H; F; Cl; Br; I; —$SF_5$; —$NO_2$; —CN; —$NH_2$; —OH; —SH; —C(=O)—$NH_2$; —S(=O)$_2$—$NH_2$; —C(=O)—NH—OH; —C(=O)—OH; —C(=O)—H; —S(=O)$_2$—OH; —C(=NH)—$NH_2$; —C(=NH)—NH—$R^9$; —N=C($NH_2$)$_2$; —N=C($NHR^{10}$)—($NHR^{11}$); —O—P(=O)$_2$—O—$R^{12}$; —$NHR^{13}$; —$NR^{14}R^{15}$; —NH—C(=O)—$R^{13}$; —$OR^{16}$; —$SR^{17}$; —C(=O)—$NHR^{18}$; —C(=O)—$NR^{19}R^{20}$; —S(=O)$_2$—$NHR^{21}$; —S(=O)$_2$—$NR^{22}R^{23}$; —C(=O)—$OR^{24}$; —C(=O)—$R^{25}$; —S(=O)—$R^{26}$; or —S(=O)$_2$—$R^{27}$ or for a linear or branched, saturated or unsaturated, unsubstituted or at least monosubstituted aliphatic $C_{1-10}$ radical;
$R^3$ stands for H; F; Cl; Br; I; —$SF_5$; —$NO_2$; —CN; —$NH_2$; —OH; —SH; —C(=O)—$NH_2$; —S(=O)$_2$—$NH_2$; —C(=O)—NH—OH; —C(=O)—OH; —C(=O)—H; —S(=O)$_2$—OH; —C(=NH)—$NH_2$; —C(=NH)—NH—$R^9$; —N=C($NH_2$)$_2$; —N=C($NHR^{10}$)—($NHR^{11}$); —O—P(=O)$_2$—O—$R^{12}$; —$NHR^{13}$; —$NR^{14}R^{15}$; —NH—C(=O)—$R^{13}$; —$OR^{16}$; —$SR^{17}$; —C(=O)—$NHR^{18}$; —C(=O)—$NR^{19}R^{20}$; —S(=O)$_2$—$NHR^{21}$; —S(=O)$_2$—$NR^{22}R^{23}$; —C(=O)—$OR^{24}$; —C(=O)—$R^{25}$; —S(=O)—$R^{26}$; or —S(=O)$_2$—$R^{27}$ or for a linear or branched, saturated or unsaturated, unsubstituted or at least monosubstituted aliphatic $C_{1-10}$ radical;
$R^4$ stands for H; F; Cl; Br; I; —$SF_5$; —$NO_2$; —CN; —$NH_2$; —OH; —SH; —C(=O)—$NH_2$; —S(=O)$_2$—$NH_2$; —C(=O)—NH—OH; —C(=O)—OH; —C(=O)—H; —S(=O)$_2$—OH; —C(=NH)—$NH_2$; —C(=NH)—NH—$R^9$; —N=C($NH_2$)$_2$; —N=C($NHR^{10}$)—($NHR^{11}$); —O—P(=O)$_2$—O—$R^{12}$; —$NHR^{13}$; —$NR^{14}R^{15}$; —NH—C(=O)—$R^{13}$; —$OR^{16}$; —$SR^{17}$; —C(=O)—$NHR^{18}$; —C(=O)—$NR^{19}R^{20}$; —S(=O)$_2$—$NHR^{21}$; —S(=O)$_2$—$NR^{22}R^{23}$; —C(=O)—$OR^{24}$; —C(=O)—$R^{25}$; —S(=O)—$R^{26}$; or —S(=O)$_2$—$R^{27}$ or for a linear or branched, saturated or unsaturated, unsubstituted or at least monosubstituted aliphatic $C_{1-10}$ radical;
$R^5$ stands for H; F; Cl; Br; I; —$SF_5$; —$NO_2$; —CN; —$NH_2$; —OH; —SH; —C(=O)—$NH_2$; —S(=O)$_2$—$NH_2$; —C(=O)—NH—OH; —C(=O)—OH; —C(=O)—H; —S(=O)$_2$—OH; —C(=NH)—$NH_2$; —C(=NH)—NH—$R^9$; —N=C($NH_2$)$_2$; —N=C($NHR^{10}$)—($NHR^{11}$); —O—P(=O)$_2$—O—$R^{12}$; —$NHR^{13}$; —$NR^{14}R^{15}$; —NH—C(=O)—$R^{13}$; —$OR^{16}$; —$SR^{17}$; —C(=O)—$NHR^{18}$; —C(=O)—$NR^{19}R^{20}$; —S(=O)$_2$—$NHR^{21}$; —S(=O)$_2$—$NR^{22}R^{23}$; —C(=O)—$OR^{24}$; —C(=O)—$R^{25}$; —S(=O)—$R^{26}$; or —S(=O)$_2$—$R^{27}$ or for a linear or branched, saturated or unsaturated, unsubstituted or at least monosubstituted aliphatic $C_{1-10}$ radical;
$R^6$ stands in each case for hydrogen or for a linear or branched, saturated or unsaturated, unsubstituted or at least monosubstituted aliphatic $C_{1-10}$ radical;
$R^7$ stands for hydrogen or —OH;
or
$R^6$ and $R^7$ form, together with the interconnecting carbon atom as ring member, a saturated or unsaturated, unsubstituted or at least monosubstituted three-membered, four-membered, five-membered, or six-membered cycloaliphatic radical;

$R^8$ stands for —$SF_5$; —O—$CF_3$; —$CF_3$; —O—$CFH_2$; —O—$CF_2H$; —$CFH_2$; —$CF_2H$; or for an unsubstituted or at least monosubstituted tert-butyl radical;

T stands for C—$R^{35}$ and U stands for C—$R^{36}$ and V stands for N and W stands for C—$R^{38}$; or T stands for C—$R^{35}$ and U stands for N and V stands for C—$R^{37}$ and W stands for C—$R^{38}$; or T stands for N and U stands for C—$R^{36}$ and V stands for C—$R^{37}$ and W stands for C—$R^{38}$; or T stands for N and U stands for N and V stands for C—$R^{37}$ and W stands for C—$R^{38}$; or T stands for N and U stands for C—$R^{36}$ and V stands for N and W stands for C—$R^{38}$; or T stands for C—$R^{35}$ and U stands for N and V stands for N and W stands for C—$R^{38}$; or T stands for C—$R^{35}$ and U stands for C—$R^{36}$ and V stands for C—$R^{37}$ and W stands for C—$R^{38}$;

$R^9, R^{10}, R^{11}, R^{12}, R^{13}, R^{14}, R^{15}, R^{16}, R^{17}, R^{18}, R^{19}, R^{20}, R^{21}, R^{22}, R^{23}, R^{24}, R^{25}, R^{26}$ and $R^{27}$ each independently stand for a linear or branched, saturated or unsaturated, unsubstituted or at least monosubstituted aliphatic $C_{1-10}$ radical;

for an unsaturated or saturated, unsubstituted or at least monosubstituted, three-membered, four-membered, five-membered, six-membered, seven-membered, eight-membered, or nine-membered cycloaliphatic radical optionally containing at least one heteroatom as ring member, which can be condensed with a saturated or unsaturated, unsubstituted or at least monosubstituted monocyclic or polycyclic ring system and/or can be bonded via a linear or branched, unsubstituted or at least monosubstituted $C_{1-6}$ alkylene group or two to six-membered heteroalkylene group;

or for an unsubstituted or at least monosubstituted five-membered to fourteen-membered aryl radical or heteroaryl radical, which can be condensed with a saturated or unsaturated, unsubstituted or at least monosubstituted monocyclic or polycyclic ring system and/or can be bonded via a linear or branched, unsubstituted or at least monosubstituted $C_{1-6}$ alkylene group or two to six-membered heteroalkylene group;

$R^{35}$, $R^{36}$, and $R^{37}$ each independently stand for H; F; Cl; Br; I; —$SF_5$; —$NO_2$; —$CF_3$; and —CN; —$NH_2$; —OH; —SH; —C(=O)—$NH_2$; —S(=O)$_2$—$NH_2$; —C(=O)—NH—OH; —C(=O)—OH; —C(=O)—H; and —S(=O)$_2$—OH; —$NHR^{13}$; —$NR^{14}R^{15}$; —NH—C(=O)—$R^{13}$; —$OR^{16}$; —$SR^{17}$; —C(=O)—$NHR^{18}$; —C(=O)—$NR^{19}R^{20}$; —S(=O)$_2$—$NHR^{21}$; and —S(=O)$_2$—$NR^{22}R^{23}$; —C(=O)—$OR^{24}$; —C(=O)—$R^{25}$; —S(=O)—$R^{26}$; —S(=O)$^2R^{27}$ for a linear or branched, saturated or unsaturated, unsubstituted or at least monosubstituted aliphatic $C_{1-10}$ radical;

or for an unsubstituted or at least monosubstituted five-membered to fourteen-membered aryl radical or heteroaryl radical, which can be condensed with a saturated or unsaturated, unsubstituted or at least monosubstituted monocyclic or polycyclic ring system and/or can be bonded via a linear or branched, unsubstituted or at least monosubstituted $C_{1-6}$ alkylene group or $C_{2-6}$ alkenylene group or $C_{2-6}$-alkynylene group;

$R^{38}$ stands for F; Cl; Br; I; —$SF_5$; —$NO_2$; —$CF_3$; —$CF_2Cl$; —CN; —$NH_2$; —OH; —SH; —C(=O)—$NH_2$; —S(=O)$_2$—$NH_2$; —C(=O)—NH—OH; and —C(=O)—OH; —C(=O)—H; —S(=O)$_2$—OH; —$NHR^{39}$;

—$NR^{40}R^{41}$; —$OR^{42}$; —$SR^{43}$; —C(=O)—$NHR^{44}$; —C(=O)—$NR^{45}R^{46}$; and —S(=O)$_2$—$NHR^{47}$; —S(=O)$_2$—$NR^{48}R^{49}$; —C(=O)—$OR^{50}$; —C(=O)—$R^{51}$; —S(=O)—$R^{52}$; —S(=O)$_2$—$R^{53}$; —C(=NH)—$NH_2$; —C(=NH)—NH—$R^{54}$; —N=C($NH_2$)$_2$; and —N=C($NHR^{55}$)—($NHR^{56}$);

for a linear or branched, saturated or unsaturated, unsubstituted or at least monosubstituted aliphatic $C_{1-10}$ radical;

for an unsaturated or saturated, unsubstituted or at least monosubstituted three-membered, four-membered, five-membered, six-membered, seven-membered, eight-membered, or nine-membered cycloaliphatic radical optionally exhibiting at least one heteroatom as ring member, each of which is bonded to the parent structure over a carbon atom in the ring of the cycloaliphatic radical and is condensed with a saturated or unsaturated, unsubstituted or at least monosubstituted monocyclic or polycyclic ring system and/or can be bonded via a linear or branched, unsubstituted or at least monosubstituted $C_{1-6}$ alkylene group or $C_{2-6}$ alkenylene group or $C_{2-6}$ alkynylene group;

or for an unsubstituted or at least monosubstituted five-membered to fourteen-membered aryl radical or heteroaryl radical, which can be condensed with a saturated or unsaturated, unsubstituted or at least monosubstituted monocyclic or polycyclic ring system and/or can be bonded via a linear or branched, unsubstituted or at least monosubstituted $C_{1-6}$ alkylene group or $C_{2-6}$ alkenylene group or $C_{2-6}$-alkynylene group;

$R^{39}, R^{40}, R^{41}, R^{42}, R^{43}, R^{44}, R^{45}, R^{46}, R^{47}, R^{48}, R^{49}, R^{50}, R^{51}, R^{52}, R^{53}, R^{54}, R^{55}$, and $R^{56}$ each independently stand for a linear or branched, saturated or unsaturated, unsubstituted or at least monosubstituted aliphatic $C_{1-10}$ radical;

for an unsaturated or saturated, unsubstituted or at least monosubstituted, three-membered, four-membered, five-membered, six-membered, seven-membered, eight-membered, or nine-membered cycloaliphatic radical optionally containing at least one heteroatom as ring member, which can be condensed with a saturated or unsaturated, unsubstituted or at least monosubstituted monocyclic or polycyclic ring system and/or can be bonded via a linear or branched, unsubstituted or at least monosubstituted $C_{1-6}$ alkylene group or two to six-membered heteroalkylene group;

or for an unsubstituted or at least monosubstituted five-membered to fourteen-membered aryl radical or heteroaryl radical, which can be condensed with a saturated or unsaturated, unsubstituted or at least monosubstituted monocyclic or polycyclic ring system and/or can be bonded via a linear or branched, unsubstituted or at least monosubstituted $C_{1-6}$ alkylene group or two to six-membered heteroalkylene group;

or $R^{40}$ and $R^{41}$ form, together with the interconnecting nitrogen atom as ring member, a saturated or unsaturated four-membered, five-membered, six-membered, seven-membered, eight-membered, or nine-membered heterocycloaliphatic radical, which is unsubstituted or substituted by 1, 2, 3, 4, or 5 radicals $R^{57}$ and optionally exhibits at least one further heteroatom as ring member, and which can be condensed with a saturated or unsaturated, unsubstituted or at least monosubstituted monocyclic or polycyclic ring system;

$R^{57}$ stands for —$NHR^{58}$, —$NR^{59}R^{60}$, or for a linear or branched, saturated or unsaturated, unsubstituted or at least monosubstituted aliphatic $C_{1-10}$ radical;

$R^{58}$, $R^{59}$, and $R^{60}$ each independently stand for —C(=O)—$R^{61}$;

for a linear or branched, saturated or unsaturated, unsubstituted or at least monosubstituted aliphatic $C_{1-10}$ radical or for an unsubstituted or at least monosubstituted five-membered to fourteen-membered aryl radical or heteroaryl radical, which can be condensed with a saturated or unsaturated, unsubstituted or at least monosubstituted monocyclic or polycyclic ring system and/or can be bonded via a linear or branched, unsubstituted or at least monosubstituted $C_{1-6}$ alkylene group or $C_{2-6}$ alkenylene group or $C_{2-6}$ alkynylene group;

and $R^{61}$ stands for a linear or branched, saturated or unsaturated, unsubstituted or at least monosubstituted aliphatic $C_{1-10}$ radical;

each optionally in the form of one of the pure stereoisomers thereof, particularly enantiomers or diastereoisomers thereof, the racemates thereof or in the form of a mixture of stereoisomers, particularly the enantiomers and/or diastereoisomers, in an arbitrary mixing ratio, or each in the form of corresponding salts, or each in the form of corresponding solvates;

wherein the aforementioned aliphatic $C_{1-10}$ radicals and tert-butyl radicals can each be optionally substituted by 1, 2, 3, 4, 5, 6, 7, 8, or 9 substituents independently selected from the group consisting of F, Cl, Br, I, —CN, —NO$_2$, —OH, —NH$_2$, —SH, —O($C_{1-5}$ alkyl), —S($C_{1-5}$ alkyl), —NH($C_{1-5}$ alkyl), —N($C_{1-5}$ alkyl)-($C_{1-5}$ alkyl), —C(=O)—O—($C_{1-5}$ alkyl), —O—C(=O)—($C_{1-5}$ alkyl), —O-phenyl, phenyl, —OCF$_3$, and —SCF$_3$;

the aforementioned two to six-membered heteroalkylene groups, $C_{1-6}$ alkylene groups, and $C_{2-6}$ alkenylene groups and $C_{2-6}$ alkynylene groups can each be optionally substituted by 1, 2, 3, 4, 5, 6, 7, 8, or 9 substituents independently selected from the group consisting of F, Cl, Br, I, —CN, —NO$_2$, —OH, —NH$_2$, —SH, —O($C_{1-5}$ alkyl), —S($C_{1-5}$ alkyl), —NH($C_{1-5}$ alkyl), —N($C_{1-5}$ alkyl)-($C_{1-5}$ alkyl), —OCF$_3$, and —SCF$_3$;

the aforementioned heteroalkylene groups each optionally exhibit 1, 2, or 3 heteroatom(s) independently selected from the group consisting of oxygen, sulfur, and nitrogen (NH) as link(s);

the aforementioned (hetero)cycloaliphatic radicals are optionally each substituted by 1, 2, 3, 4, or 5 substituents independently selected from the group consisting of —($C_{1-6}$ alkylene)—OH, =CH$_2$, —O—($C_{1-5}$ alkylene)oxetanyl, —($C_{1-5}$ alkylene)—O—($C_{1-5}$ alkylene)oxetanyl, —CH$_2$—NH—($C_{1-5}$ alkyl), —CH$_2$—N($C_{1-5}$ alkyl)$_2$, —N[C(=O)—($C_{1-5}$ alkyl)]phenyl, —CH$_2$—O—($C_{1-5}$ alkyl), oxo (=O), thioxo (=S), F, Cl, Br, I, —CN, —CF$_3$, —SF$_5$, —OH, —O—($C_{1-5}$ alkyl), —O—C(=O)—($C_{1-5}$ alkyl), —NH$_2$, —NO$_2$, —O—CF$_3$, —S—CF$_3$, —SH, —S—($C_{1-5}$ alkyl), —($C_{1-5}$ alkyl), —C(=O)—($C_{1-5}$ alkyl), —C(=O)—OH, —C(=O)—O—($C_{1-5}$ alkyl), —NH—($C_{1-5}$ alkyl), —N($C_{1-5}$ alkyl)$_2$, —NH-phenyl, —N($C_{1-5}$ alkyl)phenyl, cyclohexyl, cyclopentyl, (4,5)-dihydroisoxazolyl, thiazolyl, (1,2,5)-thiadiazolyl, thiophenyl, phenethyl, piperidinyl, pyrrolidinyl, —(CH$_2$)pyridinyl, pyridinyl, —O-phenyl, —O-benzyl, phenyl, and benzyl, and the cyclic moiety of the radicals oxetanyl, (4,5)-dihydroisoxazolyl, thiazolyl, (1,2,5)-thiadiazolyl, thiophenyl, phenethyl, —N[C(=O)—($C_{1-5}$ alkyl)]phenyl, —NH-phenyl, —N($C_{1-5}$ alkyl)phenyl, —(CH$_2$)pyridinyl, pyridinyl, —O-phenyl, —O-benzyl, phenyl, and benzyl can each be substituted by 1, 2, 3, 4, or 5 substituents independently selected from the group consisting of F, Cl, Br, —OH, —CF$_3$, —SF$_5$, —CN, —NO$_2$, —($C_{1-5}$ alkyl, —O—($C_{1-5}$ alkyl), —O—CF$_3$, —S—CF$_3$, phenyl, and —O-benzyl, and, unless otherwise stated, the aforementioned (hetero)cycloaliphatic radicals can each optionally exhibit 1, 2, or 3 (further) heteroatom(s) independently selected from the group consisting of oxygen, nitrogen, and sulfur;

the rings of the aforementioned monocyclic or polycyclic ring systems can each be optionally substituted by 1, 2, 3, 4, or 5 substituents independently selected from the group consisting of oxo (=O), thioxo (=S), F, Cl, Br, I, —CN, —CF$_3$, —SF$_5$, —OH, —O—($C_{1-5}$ alkyl), —NH$_2$, —NO$_2$, —O—CF$_3$, —S—CF$_3$, —SH, —S—($C_{1-5}$ alkyl), —($C_{1-5}$ alkyl), —C(=O)—($C_{1-5}$ alkyl), —C(=O)—OH, —C(=O)—O—($C_{1-5}$ alkyl), —NH—($C_{1-5}$ alkyl), —N($C_{1-5}$ alkyl)$_2$, —O-phenyl, —O-benzyl, phenyl, and benzyl, and the cyclic moiety of the radicals —O-phenyl, —O-benzyl, phenyl, and benzyl can each be substituted by 1, 2, 3, 4, or 5 substituents independently selected from the group consisting of F, Cl, Br, —OH, —CF$_3$, —SF$_5$, —CN, —NO$_2$, —($C_{1-5}$ alkyl), —O—($C_{1-5}$ alkyl), —O—CF$_3$, —S—CF$_3$, phenyl, and —O-benzyl, and the rings of the aforementioned monocyclic or polycyclic ring systems are each five-membered, six-membered, or seven-membered and can each optionally exhibit 1, 2, 3, 4, or 5 heteroatom(s) as ring member(s), which are independently selected from the group consisting of oxygen, nitrogen, and sulfur;

and the aforementioned aryl radicals or heteroaryl radicals can each be optionally substituted by 1, 2, 3, 4, or 5 substituents independently selected from the group consisting of F, Cl, Br, I, —CN, —CF$_3$, —SF$_5$, —OH, —O—($C_{1-5}$ alkyl), —NH$_2$, —NO$_2$, —O—CF$_3$, —S—CF$_3$, —SH, —S—($C_{1-5}$ alkyl), —($C_{1-5}$ alkyl), —C(=O)—OH, —C(=O)—O—($C_{1-5}$ alkyl), —NH—($C_{1-5}$ alkyl), —N($C_{1-5}$ alkyl)$_2$, —NH—S(=O)$_2$—($C_{1-5}$ alkyl), —NH—C(=O)—O—($C_{1-5}$ alkyl), —C(=O)—H, —C(=O)—($C_{1-5}$ alkyl), —C(=O)—NH$_2$, —C(=O)—NH—($C_{1-5}$ alkyl), —C(=O)—N—($C_{1-5}$ alkyl)$_2$, —O-phenyl, —O-benzyl, phenyl, and benzyl, and the cyclic moiety of the radicals —O-phenyl, —O-benzyl, phenyl, and benzyl can each be substituted by 1, 2, 3, 4, or 5 substituents independently selected from the group consisting of F, Cl, Br, —OH, —CF$_3$, —SF$_5$, —CN, —NO$_2$, —($C_{1-5}$ alkyl), —O—($C_{1-5}$ alkyl), —O—CF$_3$, —S—CF$_3$, phenyl, and —O-benzyl, and the aforementioned heteroaryl radicals can each optionally exhibit 1, 2, 3, 4, or 5 heteroatom(s) independently selected from the group consisting of oxygen, nitrogen, and sulfur as ring member(s).

The term "heteroalkylene" designates an alkylene chain in which one or more carbons have each been replaced by a heteroatom independently selected from the group consisting of oxygen, sulfur and nitrogen (NH). Heteroalkylene groups can preferably contain 1, 2, or 3 heteroatom(s) and more preferably one heteroatom, independently selected from the group consisting of oxygen, sulfur and nitrogen (NH), as link(s). Heteroalkylene groups can preferably be two to six-membered and more preferably two or three-membered.

Examples of heteroalkylene groups include —CH$_2$—CH$_2$—O—CH$_2$—, —CH$_2$—CH(CH$_3$)—O—CH$_2$—, —(CH$_2$)—O—, —(CH$_2$)$_2$—O—, —(CH$_2$)$_3$—O—, —(CH$_2$)$_4$—O—, —O—(CH$_2$)—, —O—(CH$_2$)$_2$—, —O—(CH$_2$)$_3$—, —O—(CH$_2$)$_4$—, —C(C$_2$H$_5$)—(H)—O—, —O—C(C$_2$H$_5$)—(H)—, —CH$_2$—O—CH$_2$—, —CH$_2$—S—CH$_2$—, —CH$_2$—NH—CH$_2$—, —CH$_2$—NH—, and —CH$_2$—CH$_2$—NH—CH$_2$—CH$_2$.

If one or more of the aforementioned substituents exhibit a linear or branched $C_{1-6}$ alkylene group, these can be preferably selected from the group consisting of —(CH$_2$)—, —(CH$_2$)$_2$—, —C(H)—(CH$_3$)—, —(CH$_2$)$_3$—, —(CH$_2$)$_4$—, —(CH$_2$)$_5$—, —C(H)—(C(H)—(CH$_3$)$_2$)—, and —C(C$_2$H$_5$)—(H)—.

Saturated or unsaturated C$_{1-10}$ aliphatic radicals can stand for a C$_{1-10}$ alkyl, C$_{2-10}$ alkenyl, or C$_{2-10}$ alkynyl radical. C$_{2-10}$ alkenyl radicals have at least one and preferably 1, 2, 3, or 4 C—C double bonds and C$_{2-10}$ alkynyl radicals at least one and preferably 1, 2, 3, or 4 C—C triple bonds.

Preference is given to C$_{1-10}$ alkyl radicals selected from the group consisting of methyl, ethyl, n-propyl, isopropyl, n-butyl, sec-butyl, isobutyl, tert-butyl, n-pentyl, 3-methylbut-1-yl, 2-pentyl, 3-pentyl, sec-pentyl, neopentyl, 4-methylpent-1-yl, (3,3)-dimethylbut-1-yl, n-hexyl, n-heptyl, 2-heptyl, 3-heptyl, 4-heptyl, n-octyl, n-nonyl, 2-nonyl, 3-nonyl, 4-nonyl, 5-nonyl, and (2,6)-dimethylhept-4-yl, which can be optionally substituted by 1, 2, 3, 4, 5, 6, 7, 8, or 9 substituents independently selected from the group consisting of —O-phenyl, —O—C(=O)—CH$_3$, —O—C(=O)—C$_2$H$_5$, —O—C(=O)—CH(CH$_3$)$_2$, —O—C(=O)—C(CH$_3$)$_3$, —C(=O)—O—CH$_3$, —C(=O)—O—C$_2$H$_5$, —C(=O)—O—CH(CH$_3$)$_2$, —C(=O)—O—C(CH$_3$)$_3$, F, Cl, Br, I, —CN, —NO$_2$, —OH, —NH$_2$, —SH, —O—CH$_3$, —O—C$_2$H$_5$, —O—CH(CH$_3$)$_2$, —O—C(CH$_3$)$_3$, —S—CH$_3$, —S—C$_2$H$_5$, —S—CH(CH$_3$)$_2$, —S—C(CH$_3$)$_3$, —NH—CH$_3$, —NH—C$_2$H$_5$, —NH—C(CH$_3$)$_3$, —N(CH$_3$)$_2$, —N(C$_2$H$_5$)$_2$, —N(CH$_3$)—(C$_2$H$_5$), —OCF$_3$, and —SCF$_3$.

In another preferred embodiment, C$_{2-10}$ alkenyl radicals are selected from the group consisting of vinyl, 1-propenyl, 2-propenyl, 1-butenyl, 2-butenyl, 3-butenyl, 2-methylpropen-1-yl, 3-methylbut-2-en-1-yl, (3,3)-dimethylbut-1-enyl, 2-methylbuten-2-yl, 1-pentenyl, 2-pentenyl, 3-pentenyl, 4-pentenyl, 1-hexenyl, 1-heptenyl, and 1-octenyl, which can be optionally substituted by 1, 2, or 3 substituents independently selected from the group consisting of F, Cl, Br, I, —CN, —NO$_2$, —OH, —NH$_2$, —SH, —O—CH$_3$, —O—C$_2$H$_5$, —O—CH(CH$_3$)$_2$, —O—C(CH$_3$)$_3$, —S—CH$_3$, —S—C$_2$H$_5$, —S—CH(CH$_3$)$_2$, —S—C(CH$_3$)$_3$, —NH—CH$_3$, —NH—C$_2$H$_5$, —NH—C(CH$_3$)$_3$, —N(CH$_3$)$_2$, —N(C$_2$H$_5$)$_2$, —N(CH$_3$)—(C$_2$H$_5$), —OCF$_3$, and —SCF$_3$.

Preference is also given to C$_{2-10}$ alkynyl radicals selected from the group consisting of (3,3)-dimethylbut-1-ynyl, 4-methylpent-1-ynyl, 1-hexynyl, ethynyl, 1-propynyl, 2-propynyl, 1-butynyl, 2-butynyl, 3-butynyl, 1-pentynyl, 2-pentynyl, 3-pentynyl, and 4-pentynyl, which can be optionally substituted by 1, 2, or 3 substituents independently selected from the group consisting of F, Cl, Br, I, —CN, —NO$_2$, —OH, —NH$_2$, —SH, —O—CH$_3$, —O—C$_2$H$_5$, —O—CH(CH$_3$)$_2$, —O—C(CH$_3$)$_3$, —S—CH$_3$, —S—C$_2$H$_5$, —S—CH(CH$_3$)$_2$, —S—C(CH$_3$)$_3$, —NH—CH$_3$, —NH—C$_2$H$_5$, —NH—C(CH$_3$)$_3$, —N(CH$_3$)$_2$, —N(C$_2$H$_5$)$_2$, —N(CH$_3$)—(C$_2$H$_5$), —OCF$_3$, and —SCF$_3$.

Particularly preferred optionally substituted C$_{1-10}$ aliphatic radicals are selected from the group consisting of methyl, —CF$_3$, —CHF$_2$, —CH$_2$F, —CF$_2$Cl, —CCl$_2$F, —CCl$_3$, —CBr$_3$, —CH$_2$—CN, —CH$_2$—O—CH$_3$, —CH$_2$—O—CF$_3$, —CH$_2$—SF$_3$, —CH$_2$—NH$_2$, —CH$_2$—OH, —CH$_2$—SH, —CH$_2$—NH—CH$_3$, —CH$_2$—N(CH$_3$)$_2$, —CH$_2$—N(C$_2$H$_5$)$_2$, —CH$_2$—N(CH$_3$)—(C$_2$H$_5$), ethyl, —CF$_2$—CH$_3$, —CHF—CF$_2$Cl, —CF$_2$—CFCl$_2$, —CFCl—CF$_2$Cl, —CFCl—CFCl$_2$, —CH$_2$—CH$_2$—NH$_2$, —CH$_2$—CH$_2$—OH, —CH$_2$—CH$_2$—SH, —CH$_2$—CH$_2$—NH—CH$_3$, —CH$_2$—CH$_2$—N(CH$_3$)$_2$, —CH$_2$—CH$_2$—N(C$_2$H$_5$)$_2$, —CH$_2$—CH$_2$—N(CH$_3$)—(C$_2$H$_5$), —CH$_2$—CF$_3$, —C$_2$F$_5$, —CH$_2$—CCl$_3$, —CH$_2$—CBr$_3$, —CH$_2$—CH$_2$—CN, n-propyl, —CH$_2$—CH$_2$—CH$_2$—OH, —CH$_2$—CH$_2$—CH$_2$—SH, —CH$_2$—CH$_2$—CH$_2$—NH$_2$, —CH$_2$—CH$_2$—CH$_2$—NH—CH$_3$, —CH$_2$—CH$_2$—CH$_2$—N(CH$_3$)$_2$, —CH$_2$—CH$_2$—CH$_2$—N(C$_2$H$_5$)$_2$, —CH$_2$—CH$_2$—CH$_2$—N(CH$_3$)—(C$_2$H$_5$), —CH$_2$—CH$_2$—O—CH$_3$, —CF$_2$—CF$_2$—CF$_3$, —CF(CF$_3$)$_2$, isopropyl, —CH$_2$—CH$_2$—CH$_2$—CN, —CH$_2$—O—CH$_2$—CH$_3$, —CH$_2$—CH$_2$—SF$_3$, —CH$_2$—CH$_2$—OCF$_3$, —CH(CH$_3$)—(O—CH$_3$), —CH(CH$_3$)—(S—CH$_3$), n-butyl, —CF$_2$—CF$_2$—CF$_2$—CF$_3$, —CH$_2$—CH$_2$—CH$_2$—CN, —CH$_2$—CH$_2$—CH$_2$—CF$_3$, —CH$_2$—CH$_2$—CH$_2$—CF$_3$, —CH$_2$—O—C(=O)—CH$_3$, —CH$_2$—O—C(=O)—C$_2$H$_5$, —CH$_2$—O—C(=O)—CH(CH$_3$)$_2$, —CH$_2$—O—C(=O)—C(CH$_3$)$_3$, —CH$_2$—C(=O)—O—CH$_3$, —CH$_2$—C(=O)—O—C$_2$H$_5$, —CH$_2$—C(=O)—O—C(CH$_3$)$_3$, —CH$_2$—CH$_2$—O—CH$_3$, —CH$_2$—CH$_2$—O—C$_2$H$_5$, —CH$_2$—CH$_2$—O-phenyl, —CH$_2$—CH$_2$—CH$_2$—O—CH$_3$, sec-butyl, isobutyl, tert-butyl, n-pentyl, sec-pentyl, neopentyl, n-hexyl, vinyl, 1-propenyl, 2-propenyl, 1-butenyl, 2-butenyl, 3-butenyl, 2-methylbutene-2-yl, (1,1,2)-trifluoro-1-butenyl, 1-pentenyl, 2-pentenyl, 3-pentenyl, 4-pentenyl, —CF=CF$_2$, —CCl=CCl$_2$, —CH$_2$—CF=CF$_2$, —CH$_2$—CCl=CCl$_2$, —C≡C—I, —C≡C—, and —C≡C—Cl.

If one or more of the aforementioned substituents stand for a (hetero)cycloaliphatic radical, which can be optionally condensed with a saturated or unsaturated, unsubstituted or at least monosubstituted monocyclic or polycyclic ring system, this can preferably be selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl, thiomorpholinyl, tetrahydropyranyl, oxetanyl, (1,2,3,6)-tetrahydropyridinyl, azepanyl, azocanyl, diazepanyl, dithiolanyl, (1,3,4,5)-tetrahydropyrido[4.3-b]indolyl, (3,4)-dihydro-1H-isoquinolinyl, (1,3,4,9)-tetrahydro[b]carbolinyl, and (1,3)-thiazolidinyl.

As examples of suitable (hetero)cycloaliphatic radicals, which can be unsubstituted or monosubstituted or polysubstituted and are condensed with a monocyclic or bicyclic ring system, there may be mentioned (4,5,6,7)-tetrahydroisoxazolo[5.4-c]pyridinyl, (2,3)-dihydro-1H-indenyl, 3-azabicyclo[3.1.1]heptyl, 3-acabicyclo[3.2.1]octyl, 6-azabicyclo[3.3.1]heptyl, 8-acabicyclo[3.2.1]octyl, isoindolyl, indolyl, (1,2,3,4)-tetrahydroquinolinyl, (1,2,3,4)-tetrahydroisoquinolinyl, (2,3)-dihydro-1H-isoindolyl, (1,2,3,4)-tetrahydronaphthyl, (2,3)-dihydrobenzo[1.4]dioxinyl, benzo[1.3]dioxolyl, (1,4)-benzodioxanyl, (2,3)-dihydrothieno[3.4-b][1.4]dioxinyl, (3,4)-dihydro-2H-benzo[1,4]oxazinyl, octahydro-1H-isoindolyl, and octahydropyrrolo[3.4-c]pyrrolyl.

(Hetero)cycloaliphatic radicals can form, within the scope of the present invention, a spirocyclic radical with another (hetero)cycloaliphatic radical via a carbon atom common to both rings.

Examples of suitable spirocyclic radicals include a 6-azaspiro[2.5]octyl radical, an 8-azaspiro[4.5]decyl radical and a 1-oxa-2,8-diazaspiro[4.5]dec-2-enyl radical. More preferably the (hetero)cycloaliphatic radicals can each be optionally substituted by 1, 2, 3, 4, or 5 substituents independently selected from the group consisting of oxo (=O), thioxo (=S), F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —NH$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl, tert-butyl, n-pentyl, —C(=O)—CH$_3$, —C(=O)—C$_2$H$_5$, —C(=O)—CH(CH$_3$)$_2$, —C(=O)—C(CH$_3$)$_3$, —C(=O)—OH, —C(=O)—O—CH$_3$, —C(=O)—O—C$_2$H$_5$, —C(=O)—O—CH(CH$_3$)$_2$, —C(=O)—O—C(CH$_3$)$_3$, —NH—CH$_3$, —NH—C$_2$H$_5$, —NH—C(CH$_3$)$_3$, —N(CH$_3$)$_2$, —N(C$_2$H$_5$)$_2$, —N(CH$_3$)—(C$_2$H$_5$), —CH$_2$—OH, —CH$_2$—

CH₂—OH, =CH₂, —CH₂—O—CH₂-oxetanyl, —O—CH₂-oxetanyl, —CH₂—N(CH₃)₂, —CH₂—N(C₂H₅)₂, —CH₂—NH—CH₃, —CH₂—NH—C₂H₅, —N—[C(=O)—C₂H₅]-phenyl, —N—[C(=O)—CH₃]-phenyl, —CH₂—O—CH₃, —CH₂—O—CH₂—CH₃, —NH-phenyl, —N(CH₃)phenyl, —N(C₂H₅)phenyl, —N(C₂H₅)phenyl, —O—CH₂—CH₂—CH₂—CH₃, (4,5)-dihydroisoxazolyl, thiazolyl, (1,2,5)-thiadiazolyl, thiophenyl, phenethyl, cyclohexyl, cyclopentyl, piperidinyl, pyrrolidinyl, —O—C(=O)—CH₃, —O—C(=O)—C₂H₅, —O—C(=O)—C(CH₃)₃, —(CH₂)pyridinyl, pyridinyl, —O-phenyl, —O-benzyl, phenyl, and benzyl, and the cyclic moiety of the radicals oxetanyl, (4,5)-dihydroisoxazolyl, thiazolyl, (1,2,5)-thiadiazolyl, thiophenyl, phenethyl, —N—[C(=O)—C₂H₅]phenyl, —N—[C(=O)—CH₃]phenyl, —NH-phenyl, —N(CH₃)phenyl, —N(C₂H₅)phenyl, —(CH₂)pyridinyl, pyridinyl, —O-phenyl, —O-benzyl, phenyl, and benzyl can each be substituted by 1, 2, 3, 4, or 5 substituents independently selected from the group consisting of F, Cl, Br, —OH, —CF₃, —SF₅, —CN, —NO₂, methyl, ethyl, n-propyl, isopropyl, n-butyl, sec-butyl, isobutyl, tert-butyl, —O—CH₃, —O—C₂H₅, —O—CH(CH₃)₂, —O—C(CH₃)₃, —O—CF₃, —S—CF₃, phenyl, and —O-benzyl.

If one or more of the aforementioned substituents stand for an aryl radical, this can preferably be selected from the group consisting of phenyl and naphthyl (1-naphthyl and 2-naphthyl).

If one or more of the aforementioned substituents stand for a heteroaryl radical, this can preferably be selected from the group consisting of tetrazolyl, thiophenyl, furanyl, pyrrolyl, pyrazolyl, pyrazinyl, pyranyl, triazolyl, pyridinyl, imidazolyl, indolyl, isoindolyl, benzo[b]furanyl, benzo[b]thiophenyl, benzoxazolyl, benzisoxazolyl, thiazolyl, oxazolyl, isoxazolyl, pyridazinyl, pyrazinyl, pyrimidinyl, indazolyl, quinoxalinyl, quinolinyl, and isoquinolinyl.

Examples of suitable aryl and heteroaryl radicals, which may be unsubstituted or monosubstituted or polysubstituted and are condensed with a monocyclic or bicyclic ring system, include isoindolyl, indolyl, (1,2,3,4)-tetrahydroquinolinyl, (1,2,3,4)-tetrahydroisoquinolinyl, (2,3)-dihydro-1H-isoindolyl, (1,2,3,4)-tetrahydronaphthyl, (2,3)-dihydrobenzo[1.4]dioxinyl, (2,3)-dihydrothieno[3.4-b][1.4]dioxinyl, benzo[1.3]dioxolyl, and (1,4)-benzodioxanyl.

More preferably, the aryl radicals or heteroaryl radicals can each be optionally substituted by 1, 2, 3, 4, or 5 substituents independently selected from the group consisting of F, Cl, Br, I, —CN, —CF₃, —SF₅, —OH, —O—CH₃, —O—C₂H₅, —O—CH(CH₃)₂, —O—C(CH₃)₃, —NH₂, —NO₂, —O—CF₃, —S—CF₃, —SH, —S—CH₃, —S—C₂H₅, —S—CH(CH₃)₂, —S—C(CH₃)₃, methyl, ethyl, n-propyl, isopropyl, n-butyl, sec-butyl, isobutyl, tert-butyl, n-pentyl, —C(=O)—OH, —C(=O)—O—CH₃, —C(=O)—O—C₂H₅, —C(=O)—O—CH(CH₃)₂, —C(=O)—O—C(CH₃)₃, —NH—CH₃, —NH—C₂H₅, —NH—C(CH₃)₃, —N(CH₃)₂, —N(C₂H₅)₂, —N(CH₃)—(C₂H₅), —NH—S(=O)₂—CH₃, —NH—S(=O)₂—C₂H₅, —NH—S(=O)₂—CH(CH₃)₂, —NH—C(=O)—O—CH₃, —NH—C(=O)—O—C₂H₅, —NH—C(=O)—O—C(CH₃)₃, —C(=O)—H, —C(=O)—CH₃, —C(=O)—C₂H₅, —C(=O)—CH(CH₃)₂, —C(=O)—C(CH₃)₃, —C(=O)—NH₂, —C(=O)—NH—CH₃, —C(=O)—NH—C₂H₅, —C(=O)—N(CH₃)₂, —C(=O)—N(C₂H₅)₂, —O-phenyl, —O-benzyl, phenyl, and benzyl, and the cyclic moiety of the radicals —O-phenyl, —O-benzyl, phenyl, and benzyl can each be substituted by 1, 2, 3, 4, or 5 substituents independently selected from the group consisting of F, Cl, Br, —OH, —CF₃, —SF₅, —CN, —NO₂, methyl, ethyl, n-propyl, isopropyl, n-butyl, sec-butyl, isobutyl, tert-butyl, —O—CH₃, —O—C₂H₅, —O—CH(CH₃)₂, —O—C(CH₃)₃, —O—CF₃, —S—CF₃, phenyl, and —O-benzyl.

If a polycyclic ring system such as a bicyclic ring system is present, the different rings can independently exhibit a different degree of saturation, i.e. be saturated or unsaturated. A polycyclic ring system is preferably a bicyclic ring system.

Examples of aryl radicals condensed with a monocyclic or polycyclic ring system include (1,3)-benzodioxolyl and (1,4)-benzodioxanyl.

If one or more of the aforementioned substituents have a monocyclic or polycyclic ring system, this can preferably be substituted by 1, 2, 3, 4, or 5 substituents independently selected from the group consisting of oxo (=O), thioxo (=S), F, Cl, Br, I, —CN, —CF₃, —SF₅, —OH, —O—CH₃, —O—C₂H₅, —O—CH(CH₃)₂, —O—C(CH₃)₃, —NH₂, —NO₂, —O—CF₃, —S—CF₃, —SH, —S—CH₃, —S—C₂H₅, —S—CH(CH₃)₂, —S—C(CH₃)₃, methyl, ethyl, n-propyl, isopropyl, n-butyl, sec-butyl, isobutyl, tert-butyl, n-pentyl, —C(=O)—OH, —C(=O)—O—CH₃, —C(=O)—O—C₂H₅, —C(=O)—O—CH(CH₃)₂, —C(=O)—O—C(CH₃)₃, —NH—CH₃, —NH—C₂H₅, —NH—C(CH₃)₃, —N(CH₃)₂, —N(C₂H₅)₂, —N(CH₃)—(C₂H₅), —NH—C(=O)—O—CH₃, —NH—C(=O)—O—C₂H₅, —NH—C(=O)—O—C(CH₃)₃, —C(=O)—H, —C(=O)—CH₃, —C(=O)—C₂H₅, —C(=O)—CH(CH₃)₂, —C(=O)—C(CH₃)₃, —C(=O)—NH₂, —C(=O)—NH—CH₃, —C(=O)-nH—C₂H₅, —C(=O)—N(CH₃)₂, —C(=O)—N(C₂H₅)₂, —O-phenyl, —O-benzyl, phenyl, and benzyl, and the cyclic moiety of the radicals —O-phenyl, —O-benzyl, phenyl, and benzyl can each be substituted by 1, 2, 3, 4, or 5 substituents independently selected from the group consisting of F, Cl, Br, —OH, —CF₃, —SF₅, —CN, —NO₂, methyl, ethyl, n-propyl, isopropyl, n-butyl, sec-butyl, isobutyl, tert-butyl, —O—CH₃, —O—C₂H₅, —O—CH(CH₃)₂, —O—C(CH₃)₃, —O—CF₃, —S—CF₃, phenyl, and —O-benzyl.

If $R^{41}$ and $R^{42}$ together with the interconnecting nitrogen atom as ring member form a heterocycloaliphatic radical, which is substituted by 1, 2, 3, 4, or 5 radicals $R^{57}$, said radicals $R^{57}$ may each be independently from one another selected from the above given meanings.

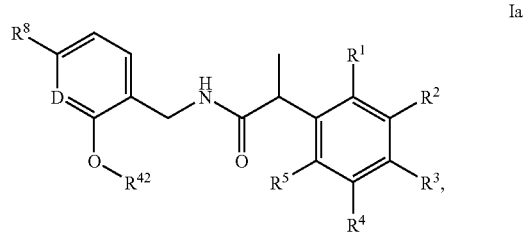

Ia in which
D stands for N or CH;
$R^1$ stands for H; F; Cl; Br; I; —NO₂; —CF₃; —CN; —NH₂; —OH; —NH—C(=O)—$R^{13}$; —O$R^{16}$; —S$R^{17}$; —S(=O)₂—NR²²R²³; —S(=O)₂—$R^{27}$, or for a radical selected from the group consisting of methyl, —CF₃, —CHF₂, —CH₂F, ethyl, n-propyl, isopropyl, n-butyl, sec-butyl, isobutyl, and tert-butyl;
$R^2$ stands for H; F; Cl; Br; I; —NO₂; —CF₃; —CN; —NH₂; —OH; —NH—C(=O)—$R^{13}$; —O$R^{16}$; —S$R^{17}$; —S(=O)₂—NR²²R²³; —S(=O)₂—$R^{27}$, or for a radical selected from the group consisting of methyl, —CF₃, —CHF$_2$, —CH$_2$F, ethyl, n-propyl, isopropyl, n-butyl, sec-butyl, isobutyl, and tert-butyl;

R$^3$ stands for H; F; Cl; Br; I; —NO$_2$; —CF$_3$; —CN; —NH$_2$; —OH; —NH—C(=O)—R$^{13}$; —OR$^{16}$; —SR$^{17}$; —S(=O)$_2$—NR$^{22}$R$^{23}$; —S(=O)$_2$—R$^{27}$, or for a radical selected from the group consisting of methyl, —CF$_3$, —CHF$_2$, —CH$_2$F, ethyl, n-propyl, isopropyl, n-butyl, sec-butyl, isobutyl, and tert-butyl;

R$^4$ stands for H; F; Cl; Br; I; —NO$_2$; —CF$_3$; —CN; —NH$_2$; —OH; —NH—C(=O)—R$^{13}$; —OR$^{16}$; —SR$^{17}$; —S(=O)$_2$—NR$^{22}$R$^{23}$; —S(=O)$_2$—R$^{27}$, or for a radical selected from the group consisting of methyl, —CF$_3$, —CHF$_2$, —CH$_2$F, ethyl, n-propyl, isopropyl, n-butyl, sec-butyl, isobutyl, and tert-butyl;

R$^5$ stands for H; F; Cl; Br; I; —NO$_2$; —CF$_3$; —CN; —NH$_2$; —OH; —NH—C(=O)—R$^{13}$; —OR$^{16}$; —SR$^{17}$; —S(=O)$_2$—NR$^{22}$R$^{23}$; —S(=O)$_2$—R$^{27}$, or for a radical selected from the group consisting of methyl, —CF$_3$, —CHF$_2$, —CH$_2$F, ethyl, n-propyl, isopropyl, n-butyl, sec-butyl, isobutyl, and tert-butyl;

R$^8$ stands for —SF$_5$; —O—CF$_3$; —CF$_3$; tert-butyl; or —C(CH$_3$)$_2$(CH$_2$OH);

R$^{13}$, R$^{16}$, R$^{17}$, R$^{22}$, R$^{23}$ and R$^{27}$, each independently stand for a radical selected from the group consisting of methyl, —CF$_3$, —CHF$_2$, —CH$_2$F, ethyl, —CF$_2$—CH$_3$, —CH$_2$—CF$_3$, —C$_2$F$_5$, n-propyl, isopropyl, n-butyl, sec-butyl, isobutyl, tert-butyl, n-pentyl, 3-pentyl, n-heptyl, 4-heptyl, n-octyl, n-nonyl, 5-nonyl, (2,6)-dimethylhept-4-yl, 3-methylbutyl, n-hexyl, (3,3)-dimethylbutyl and ethenyl;

R$^{42}$ stands for a radical selected from the group consisting of methyl, —CH$_2$—O—CH$_3$, ethyl, n-propyl, n-butyl, sec-butyl, isobutyl, tert-butyl, n-pentyl, 3-pentyl, n-hexyl, (3,3)-dimethylbutyl, —CH$_2$—CH$_2$—O—CH$_3$, —CH$_2$—CH$_2$—O—C$_2$H$_5$, and —CH$_2$—CH$_2$—CH$_2$—O—CH$_3$;

or for a radical selected from the group consisting of 2,3-dihydro-1H-indenyl, cyclopropyl, oxetanyl, cyclobutyl, cyclopentyl, cyclohexyl, imidazolidinyl, tetrahydrofuranyl, tetrahydrothiophenyl, pyrrolidinyl, piperidinyl, morpholinyl, piperazinyl, azepanyl, diazepanyl, azocanyl, and thiomorpholinyl, each of which can be optionally substituted by 1, 2, 3, 4, or 5 substituents independently selected from the group consisting of methyl, ethyl, n-propyl, isopropyl, n-butyl, sec-butyl, isobutyl, tert-butyl, and n-pentyl;

in each case optionally in the form of one of the pure stereoisomers thereof, particularly enantiomers or diastereoisomers, or the racemates thereof or in the form of a mixture of stereoisomers, particularly the enantiomers and/or diastereoisomers, in an arbitrary mixing ratio, or in each case in the form of corresponding salts, or in each case in the form of corresponding solvates.

Special preference is given to compounds of the general formula Ia,

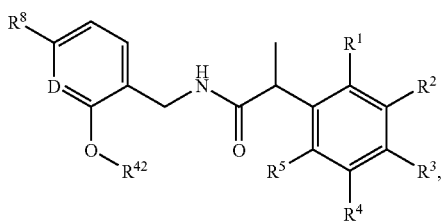

in which

D stands for N or CH;

R$^1$ stands for H; F; Cl; Br; I; methyl, ethyl, —NO$_2$; —OH; —NH$_2$; —NH—C(=O)—R$^{13}$; —OR$^{16}$; —SR$^{17}$; —S(=O)$_2$—NR$^{22}$R$^{23}$ or —(S=O)—R$^{27}$, R$^2$ stands for H; F; Cl; Br; I; methyl, ethyl, —NO$_2$; —OH; —NH$_2$; —NH—C(=O)—R$^{13}$; —OR$^{16}$; —SR$^{17}$; —S(=O)$_2$—NR$^{22}$R$^{23}$ or —(S=O)—R$^{27}$;

R$^3$ stands for H; F; Cl; Br; I; methyl, ethyl, —NO$_2$; —OH; —NH$_2$; —NH—C(=O)—R$^{13}$; —OR$^{16}$; —SR$^{17}$; —S(=O)$_2$—NR$^{22}$R$^{23}$ or —(S=O)—R$^{27}$;

R$^4$ stands for H; F; Cl; Br; I; methyl, ethyl, —NO$_2$; —OH; —NH$_2$; —NH—C(=O)—R$^{13}$; —OR$^{16}$; —SR$^{17}$; —S(=O)$_2$—NR$^{22}$R$^{23}$ or —(S=O)—R$^{27}$;

R$^5$ stands for H; F; Cl; Br; I; methyl, ethyl, —NO$_2$; —OH; —NH$_2$; —NH—C(=O)—R$^{13}$; —OR$^{16}$; —SR$^{17}$; —S(=O)$_2$—NR$^{22}$R$^{23}$ or —(S=O)—R$^{27}$;

R$^8$ stands for —SF$_5$; —O—CF$_3$; —CF$_3$; tert-butyl; or —C(CH$_3$)$_2$(CH$_2$OH);

R$^{13}$, R$^{16}$, R$^{17}$, R$^{22}$, R$^{23}$ and R$^{27}$ each independently stand for a radical selected from the group consisting of methyl, ethyl, n-propyl, isopropyl, n-butyl, sec-butyl, isobutyl, tert-butyl, n-pentyl and ethenyl;

R$^{42}$ stands for a radical selected from the group consisting of methyl, ethyl, n-propyl, n-butyl, sec-butyl, isobutyl, tert-butyl, n-pentyl, 3-pentyl, n-hexyl, and (3,3)-dimethylbutyl;

or for a radical selected from the group consisting of cyclopropyl, cyclobutyl, cyclopentyl, cyclohexyl, and cycloheptyl, each of which can be optionally substituted by 1, 2, 3, 4, or 5 substituents independently selected from the group consisting of methyl, ethyl, n-propyl, isopropyl, n-butyl, sec-butyl, isobutyl, tert-butyl, and n-pentyl;

in each case optionally in the form of one of the pure stereoisomers thereof, particularly enantiomers or diastereoisomers, or the racemates thereof or in the form of a mixture of stereoisomers, particularly the enantiomers and/or diastereoisomers, in an arbitrary mixing ratio, or in each case in the form of corresponding salts, or in each case in the form of corresponding solvates.

Very special preference is given to compounds of the general formula Ia,

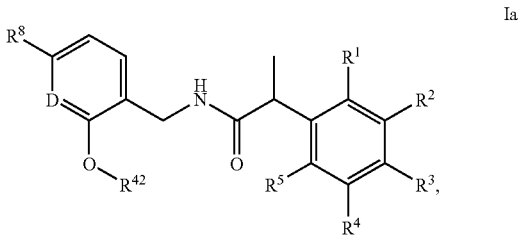

in which

D stands for N or CH;

R$^1$ stands for H; F; Cl; Br or I;

R$^2$ stands for H; F; Cl; Br; I; methyl; —OH; —NH$_2$ or —OR$^{16}$;

R$^3$ stands for H; F; Cl; Br; I; —NO$_2$; —OH; —NH$_2$; —NH—C(=O)—R$^{13}$, —OR$^{16}$; SR$^{17}$; —S(=O)—NR$^{22}$R$^{23}$ or —S(=O)—R$^{27}$;

R$^4$ stands for H; F; Cl; Br; I; methyl, —OH; —NH$_2$ or —OR$^{16}$;

R$^5$ stands for H; F; Cl; Br; or I;

R$^8$ stands for —SF$_5$; —O—CF$_3$; —CF$_3$; tert-butyl; or —C(CH$_3$)$_2$(CH$_2$OH);

$R^{13}$, $R^{16}$, $R^{17}$, $R^{22}$, $R^{23}$ and $R^{27}$ each independently stand for a radical selected from the group consisting of methyl, ethyl, n-propyl, isopropyl, n-butyl, sec-butyl, isobutyl, tert-butyl, n-pentyl and ethenyl;

$R^{42}$ stands for a radical selected from the group consisting of methyl, ethyl, n-propyl, n-butyl, sec-butyl, isobutyl, tert-butyl, n-pentyl, 3-pentyl, n-hexyl, and (3,3)-dimethylbutyl;

or for a radical selected from the group consisting of cyclopropyl, cyclobutyl, cyclopentyl, cyclohexyl, and cycloheptyl, each of which can be optionally substituted by 1, 2, 3, 4, or 5 substituents independently selected from the group consisting of methyl, ethyl, n-propyl, isopropyl, n-butyl, sec-butyl, isobutyl, tert-butyl, and n-pentyl;

in each case optionally in the form of one of the pure stereoisomers thereof, particularly enantiomers or diastereoisomers, or the racemates thereof or in the form of a mixture of stereoisomers, particularly the enantiomers and/or diastereoisomers, in an arbitrary mixing ratio, or in each case in the form of corresponding salts, or in each case in the form of corresponding solvates.

Preference is given to compounds of the general formula Ib,

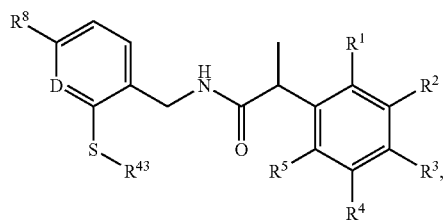

Ib in which

D stands for N or CH;

$R^1$ stands for H; F; Cl; Br; I; —$NO_2$; —$CF_3$; —CN; —$NH_2$; —OH; —NH—C(=O)—$R^{13}$; —$OR^{16}$; —$SR^{17}$; —S(=O)$_2$—$NR^{22}R^{23}$; —S(=O)$_2$—$R^{27}$, or for a radical selected from the group consisting of methyl, —$CF_3$, —$CHF_2$, —$CH_2F$, ethyl, n-propyl, isopropyl, n-butyl, sec-butyl, isobutyl, and tert-butyl;

$R^2$ stands for H; F; Cl; Br; I; —$NO_2$; —$CF_3$; —CN; —$NH_2$; —OH; —NH—C(=O)—$R^{13}$; —$OR^{16}$; —$SR^{17}$; —S(=O)$_2$—$NR^{22}R^{23}$; —S(=O)$_2$—$R^{27}$, or for a radical selected from the group consisting of methyl, —$CF_3$, —$CHF_2$, —$CH_2F$, ethyl, n-propyl, isopropyl, n-butyl, sec-butyl, isobutyl, and tert-butyl;

$R^3$ stands for H; F; Cl; Br; I; —$NO_2$; —$CF_3$; —CN; —$NH_2$; —OH; —NH—C(=O)—$R^{13}$; —$OR^{16}$; —$SR^{17}$; —S(=O)$_2$—$NR^{22}R^{23}$; —S(=O)$_2$—$R^{27}$, or for a radical selected from the group consisting of methyl, —$CF_3$, —$CHF_2$, —$CH_2F$, ethyl, n-propyl, isopropyl, n-butyl, sec-butyl, isobutyl, and tert-butyl;

$R^4$ stands for H; F; Cl; Br; I; —$NO_2$; —$CF_3$; —CN; —$NH_2$; —OH; —NH—C(=O)—$R^{13}$; —$OR^{16}$; —$SR^{17}$; —S(=O)$_2$—$NR^{22}R^{23}$; —S(=O)$_2$—$R^{27}$, or for a radical selected from the group consisting of methyl, —$CF_3$, —$CHF_2$, —$CH_2F$, ethyl, n-propyl, isopropyl, n-butyl, sec-butyl, isobutyl, and tert-butyl;

$R^5$ stands for H; F; Cl; Br; I; —$NO_2$; —$CF_3$; —CN; —$NH_2$; —OH; —NH—C(=O)—$R^{13}$; —$OR^{16}$; —$SR^{17}$; —S(=O)$_2$—$NR^{22}R^{23}$; —S(=O)$_2$—$R^{27}$, or for a radical selected from the group consisting of methyl, —$CF_3$, —$CHF_2$, —$CH_2F$, ethyl, n-propyl, isopropyl, n-butyl, sec-butyl, isobutyl, and tert-butyl;

$R^8$ stands for —$SF_5$; —O—$CF_3$; —$CF_3$; tert-butyl; or —$C(CH_3)_2(CH_2OH)$;

$R^{13}$, $R^{16}$, $R^{17}$, $R^{22}$, $R^{23}$ and $R^{27}$ each independently stand for a radical selected from the group consisting of methyl, —$CF_3$, —$CHF_2$, —$CH_2F$, ethyl, —$CF_2$—$CH_3$, —$CH_2$—$CF_3$, —$C_2F_5$, n-propyl, isopropyl, n-butyl, sec-butyl, isobutyl, tert-butyl, n-pentyl, 3-pentyl, n-heptyl, 4-heptyl, n-octyl, n-nonyl, 5-nonyl, (2,6)-dimethylhept-4-yl, 3-methylbutyl, n-hexyl, (3,3)-dimethylbutyl and ethenyl;

$R^{43}$ stands for a radical selected from the group consisting of methyl, —$CH_2$—O—$CH_3$, ethyl, n-propyl, n-butyl, sec-butyl, isobutyl, tert-butyl, n-pentyl, 3-pentyl, n-hexyl, (3,3)-dimethylbutyl, —$CH_2$—$CH_2$—O—$CH_3$, —$CH_2$—$CH_2$—O—$C_2H_5$, and —$CH_2$—$CH_2$—$CH_2$—O—$CH_3$;

or for a radical selected from the group consisting of 2,3-dihydro-1H-indenyl, cyclopropyl, oxetanyl, cyclobutyl, cyclopentyl, cyclohexyl, imidazolidinyl, tetrahydrofuranyl, tetrahydrothiophenyl, pyrrolidinyl, piperidinyl, morpholinyl, piperazinyl, azepanyl, diazepanyl, azocanyl, and thiomorpholinyl, each of which can be optionally substituted by 1, 2, 3, 4, or 5 substituents independently selected from the group consisting of methyl, ethyl, n-propyl, isopropyl, n-butyl, sec-butyl, isobutyl, tert-butyl, and n-pentyl;

in each case optionally in the form of one of the pure stereoisomers thereof, particularly enantiomers or diastereoisomers, or the racemates thereof or in the form of a mixture of stereoisomers, particularly the enantiomers and/or diastereoisomers, in an arbitrary mixing ratio, or in each case in the form of corresponding salts, or in each case in the form of corresponding solvates.

Special preference is given to compounds of the general formula Ib,

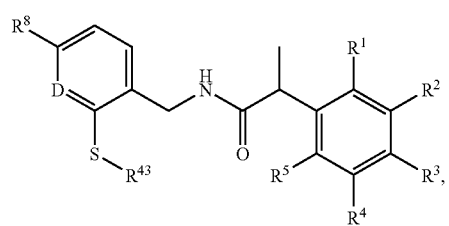

Ib in which

D stands for N or CH;

$R^1$ stands for H; F; Cl; Br; I; methyl, ethyl, —$NO_2$; —OH; —$NH_2$; —NH—C(=O)—$R^{13}$; —$OR^{16}$; —$SR^{17}$—S(=O)$_2$—$NR^{22}R^{23}$ or —(S=O)—$R^{27}$, $R^2$ stands for H; F; Cl; Br; I; methyl, ethyl, —$NO_2$; —OH; —$NH_2$; —NH—C(=O)—$R^{13}$; —$OR^{16}$; —$SR^{17}$, —S(=O)$_2$—$NR^{22}R^{23}$ or —(S=O)—$R^{27}$;

$R^3$ stands for H; F; Cl; Br; I; methyl, ethyl, —$NO_2$; —OH; —$NH_2$; —NH—C(=O)—$R^{13}$; —$OR^{16}$; —$SR^{17}$, —S(=O)$_2$—$NR^{22}R^{23}$ or —(S=O)—$R^{27}$;

$R^4$ stands for H; F; Cl; Br; I; methyl, ethyl, —$NO_2$; —OH; —$NH_2$; —NH—C(=O)—$R^{13}$; —$OR^{16}$; —$SR^{17}$, —S(=O)$_2$—$NR^{22}R^{23}$ or —(S=O)—$R^{27}$;

$R^5$ stands for H; F; Cl; Br; I; methyl, ethyl, —$NO_2$; —OH; —$NH_2$; —NH—C(=O)—$R^{13}$; —$OR^{16}$; —$SR^{17}$, —S(=O)$_2$—$NR^{22}R^{23}$ or —(S=O)—$R^{27}$;

$R^8$ stands for —$SF_5$; —O—$CF_3$; —$CF_3$; tert-butyl; or —$C(CH_3)_2(CH_2OH)$;

$R^{13}$, $R^{16}$, $R^{17}$, $R^{22}$, $R^{23}$ and $R^{27}$ each independently stand for a radical selected from the group consisting of methyl, ethyl, n-propyl, isopropyl, n-butyl, sec-butyl, isobutyl, tert-butyl, n-pentyl, and ethenyl;

$R^{43}$ stands for a radical selected from the group consisting of methyl, ethyl, n-propyl, n-butyl, sec-butyl, isobutyl, tert-butyl, n-pentyl, 3-pentyl, n-hexyl, and (3,3)-dimethylbutyl;

or for a radical selected from the group consisting of cyclopropyl, cyclobutyl, cyclopentyl, cyclohexyl, and cycloheptyl, each of which can be optionally substituted by 1, 2, 3, 4, or 5 substituents independently selected from the group consisting of methyl, ethyl, n-propyl, isopropyl, n-butyl, sec-butyl, isobutyl, tert-butyl, and n-pentyl;

in each case optionally in the form of one of the pure stereoisomers thereof, particularly enantiomers or diastereoisomers, or the racemates thereof or in the form of a mixture of stereoisomers, particularly the enantiomers and/or diastereoisomers, in an arbitrary mixing ratio, or in each case in the form of corresponding salts, or in each case in the form of corresponding solvates.

Very special preference is given to compounds of the general formula Ib,

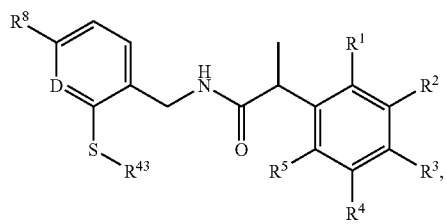

in which

D stands for N or CH;

$R^1$ stands for H; F; Cl; Br or I;

$R^2$ stands for H; F; Cl; Br; I; methyl; —OH; —$NH_2$ or —$OR^{16}$;

$R^3$ stands for H; F; Cl; Br; I; —$NO_2$; —OH; —$NH_2$; —NH—C(=O)—$R^{13}$, —$OR^{16}$; $SR^{17}$; —S(=O)—$NR^{22}R^{23}$ or —S(=O)—$R^{27}$;

$R^4$ stands for H; F; Cl; Br; I; methyl; —OH; —$NH_2$ or —$OR^{16}$;

$R^5$ stands for H; F; Cl; Br; or I;

$R^8$ stands for —$SF_5$; —O—$CF_3$; —$CF_3$; tert-butyl; or —C($CH_3$)$_2$($CH_2OH$);

$R^{13}$, $R^{16}$, $R^{17}$, $R^{22}$, $R^{23}$ and $R^{27}$ each independently stand for a radical selected from the group consisting of methyl, ethyl, n-propyl, isopropyl, n-butyl, sec-butyl, isobutyl, tert-butyl, n-pentyl, and ethenyl;

$R^{43}$ stands for a radical selected from the group consisting of methyl, ethyl, n-propyl, n-butyl, sec-butyl, isobutyl, tert-butyl, n-pentyl, 3-pentyl, n-hexyl, and (3,3)-dimethylbutyl;

or for a radical selected from the group consisting of cyclopropyl, cyclobutyl, cyclopentyl, cyclohexyl, and cycloheptyl, each of which can be optionally substituted by 1, 2, 3, 4, or 5 substituents independently selected from the group consisting of methyl, ethyl, n-propyl, isopropyl, n-butyl, sec-butyl, isobutyl, tert-butyl, and n-pentyl;

in each case optionally in the form of one of the pure stereoisomers thereof, particularly enantiomers or diastereoisomers, or the racemates thereof or in the form of a mixture of stereoisomers, particularly the enantiomers and/or diastereoisomers, in an arbitrary mixing ratio, or in each case in the form of corresponding salts, or in each case in the form of corresponding solvates.

Preference is given to compounds of the general formula Ic,

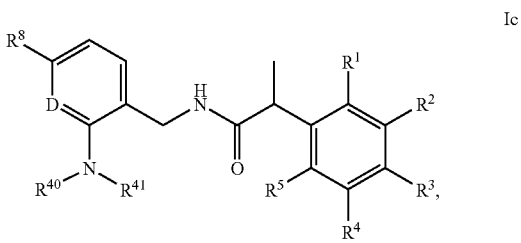

in which

D stands for N or CH;

$R^1$ stands for H; F; Cl; Br; I; —$NO_2$; —$CF_3$; —CN; —$NH_2$; —OH; —NH—C(=O)—$R^{13}$; —$OR^{16}$; —$SR^{17}$; —S(=O)$_2$—$NR^{22}R^{23}$; —S(=O)$_2$—$R^{27}$, or for a radical selected from the group consisting of methyl, —$CF_3$, —$CHF_2$, —$CH_2F$, ethyl, n-propyl, isopropyl, n-butyl, sec-butyl, isobutyl, and tert-butyl;

$R^2$ stands for H; F; Cl; Br; I; —$NO_2$; —$CF_3$; —CN; —$NH_2$; —OH; —NH—C(=O)—$R^{13}$; —$OR^{16}$; —$SR^{17}$; —S(=O)$_2$—$NR^{22}R^{23}$; —S(=O)$_2$—$R^{27}$, or for a radical selected from the group consisting of methyl, —$CF_3$, —$CHF_2$, —$CH_2F$, ethyl, n-propyl, isopropyl, n-butyl, sec-butyl, isobutyl, and tert-butyl;

$R^3$ stands for H; F; Cl; Br; I; —$NO_2$; —$CF_3$; —CN; —$NH_2$; —OH; —NH—C(=O)—$R^{13}$; —$OR^{16}$; —$SR^{17}$; —S(=O)$_2$—$NR^{22}R^{23}$; —S(=O)$_2$—$R^{27}$, or for a radical selected from the group consisting of methyl, —$CF_3$, —$CHF_2$, —$CH_2F$, ethyl, n-propyl, isopropyl, n-butyl, sec-butyl, isobutyl, and tert-butyl;

$R^4$ stands for H; F; Cl; Br; I; —$NO_2$; —$CF_3$; —CN; —$NH_2$; —OH; —NH—C(=O)—$R^{13}$; —$OR^{16}$; —$SR^{17}$; —S(=O)$_2$—$NR^{22}R^{23}$; —S(=O)$_2$—$R^{27}$, or for a radical selected from the group consisting of methyl, —$CF_3$, —$CHF_2$, —$CH_2F$, ethyl, n-propyl, isopropyl, n-butyl, sec-butyl, isobutyl, and tert-butyl;

$R^5$ stands for H; F; Cl; Br; I; —$NO_2$; —$CF_3$; —CN; —$NH_2$; —OH; —NH—C(=O)—$R^{13}$; —$OR^{16}$; —$SR^{17}$; —S(=O)$_2$—$NR^{22}R^{23}$; —S(=O)$_2$—$R^{27}$, or for a radical selected from the group consisting of methyl, —$CF_3$, —$CHF_2$, —$CH_2F$, ethyl, n-propyl, isopropyl, n-butyl, sec-butyl, isobutyl, and tert-butyl;

$R^8$ stands for —$SF_5$; —O—$CF_3$; —$CF_3$; tert-butyl; or —C($CH_3$)$_2$($CH_2OH$);

$R^{13}$, $R^{16}$, $R^{17}$, $R^{22}$, $R^{23}$ and $R^{27}$ each independently stand for a radical selected from the group consisting of methyl, —$CF_3$, —$CHF_2$, —$CH_2F$, ethyl, —$CF_2$—$CH_3$, —$CH_2$—$CF_3$, —$C_2F_5$, n-propyl, isopropyl, n-butyl, sec-butyl, isobutyl, tert-butyl, n-pentyl, 3-pentyl, n-heptyl, 4-heptyl, n-octyl, n-nonyl, 5-nonyl, (2,6)-dimethylhept-4-yl, 3-methylbutyl, n-hexyl, (3,3)-dimethylbutyl, and ethenyl;

$R^{40}$ and $R^{41}$ each independently stand for a radical selected from the group consisting of methyl, —$CH_2$—O—$CH_3$, ethyl, n-propyl, n-butyl, sec-butyl, isobutyl, tert-butyl, n-pentyl, 3-pentyl, n-hexyl, (3,3)-dimethylbutyl, —$CH_2$—$CH_2$—O—$CH_3$, —$CH_2$—$CH_2$—O—$C_2H_5$, and —$CH_2$—$CH_2$—$CH_2$—O—$CH_3$;

or for a radical selected from the group consisting of 2,3-dihydro-1H-indenyl, cyclopropyl, oxetanyl, cyclobutyl, cyclopentyl, cyclohexyl, imidazolidinyl, tetrahydrofuranyl, tetrahydrothiophenyl, pyrrolidinyl, piperidinyl, morpholinyl, piperazinyl, azepanyl, diazepanyl, azocanyl, and thiomorpholinyl, each of which can be optionally substituted by 1, 2, 3, 4, or 5 substituents independently selected from the group consisting of methyl, ethyl, n-propyl, isopropyl, n-butyl, sec-butyl, isobutyl, tert-butyl, and n-pentyl;

or $R^{40}$ and $R^{41}$ form, together with the interconnecting nitrogen atom as ring member, a radical selected from the group consisting of 3-azabicyclo[3.1.1]heptyl, 6-azaspiro[2.5]octyl, 3-acabicyclo[3.2.1]octyl, 6-azabicyclo[3.3.1]heptyl, 8-acabicyclo[3.2.1]octyl, 1-oxa-2,8-diazaspiro[4.5]dec-2-enyl, azocanyl, isoindolyl, indolyl, (1,2,3,6)-tetrahydropyridinyl, (4,5,6,7)-tetrahydroisoxazolo[5.4-c]pyridinyl, pyrrolidinyl, piperidinyl, piperazinyl, morpholinyl, azepanyl, diazepanyl, and thiomorpholinyl, of which the heterocycloaliphatic moiety can in each case be unsubstituted or substituted by 1, 2, 3, 4, or 5 radicals $R^{57}$;

$R^{57}$ stands for —$NHR^{53}$, —$NR^{59}R^{60}$, or for an alkyl radical selected from the group consisting of —$CF_3$, —$CH_2$—$CF_3$, methyl, ethyl, n-propyl, isopropyl, tert-butyl, n-butyl, sec-butyl, and isobutyl;

$R^{58}$, $R^{59}$, and $R^{60}$ each independently stand for —C(=O)—$R^{61}$;

for an alkyl radical selected from the group consisting of —$CF_3$, —$CH_2$—$CF_3$, methyl, ethyl, n-propyl, isopropyl, tert-butyl, n-butyl, sec-butyl, and isobutyl;

or for a radical selected from the group consisting of phenyl and naphthyl, and each radical can be bonded via a —$(CH_2)$—, —$(CH_2)_2$— or —$(CH_2)_3$ group and/or can each be unsubstituted or optionally substituted by 1, 2, 3, 4, or 5 substituents independently selected from the group consisting of F, Cl, Br, I, —CN, —$CF_3$, —O—$CH_3$, —O—$C_2H_5$, —O—$CH(CH_3)_2$, —O—$C(CH_3)_3$, methyl, ethyl, n-propyl, isopropyl, n-butyl, sec-butyl, isobutyl, tert-butyl, and n-pentyl;

and $R^{61}$ stands for an alkyl radical selected from the group consisting of —$CF_3$, —$CH_2$—$CF_3$, methyl, ethyl, n-propyl, isopropyl, tert-butyl, n-butyl, sec-butyl, and isobutyl;

in each case optionally in the form of one of the pure stereoisomers thereof, particularly enantiomers or diastereoisomers, or the racemates thereof or in the form of a mixture of stereoisomers, particularly the enantiomers and/or diastereoisomers, in an arbitrary mixing ratio, or in each case in the form of corresponding salts, or in each case in the form of corresponding solvates.

Special preference is given to compounds of the general formula Ic,

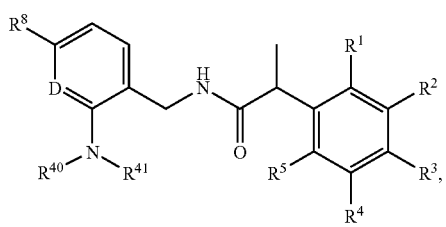

Ic in which

D stands for N or CH;

$R^1$ stands for H; F; Cl; Br; I; methyl, ethyl, —$NO_2$; —OH; —$NH_2$; —NH—C(=O)—$R^{13}$; —$OR^{16}$; —$SR^{17}$, —S(=O)$_2$—$NR^{22}R^{23}$ or —(S=O)—$R^{27}$, $R^2$ stands for H; F; Cl; Br; I; methyl, ethyl, —$NO_2$; —OH; —$NH_2$; —NH—C(=O)—$R^{13}$; —$OR^{16}$; —$SR^{17}$—S(=O)$_2$—$NR^{22}R^{23}$ or —(S=O)—$R^{27}$;

$R^3$ stands for H; F; Cl; Br; I; methyl, ethyl, —$NO_2$; —OH; —$NH_2$; —NH—C(=O)—$R^{13}$; —$OR^{16}$; —$SR^{17}$, —S(=O)$_2$—$NR^{22}R^{23}$ or —(S=O)—$R^{27}$;

$R^4$ stands for H; F; Cl; Br; I; methyl, ethyl, —$NO_2$; —OH; —$NH_2$; —NH—C(=O)—$R^{13}$; —$OR^{16}$; —$SR^{17}$, —S(=O)$_2$—$NR^{22}R^{23}$ or —(S=O)—$R^{27}$;

$R^5$ stands for H; F; Cl; Br; I; methyl, ethyl, —$NO_2$; —OH; —$NH_2$; —NH—C(=O)—$R^{13}$; —$OR^{16}$; —$SR^{17}$, —S(=O)$_2$—$NR^{22}R^{23}$ or —(S=O)—$R^{27}$;

$R^8$ stands for —$SF_5$; —O—$CF_3$; —$CF_3$; tert-butyl; or —$C(CH_3)_2(CH_2OH)$;

$R^{13}$, $R^{16}$, $R^{17}$, $R^{22}$, $R^{23}$ and $R^{27}$ each independently stand for a radical selected from the group consisting of methyl, ethyl, n-propyl, isopropyl, n-butyl, sec-butyl, isobutyl, tert-butyl, n-pentyl, and ethenyl;

$R^{40}$ and $R^{41}$ form, together with the interconnecting nitrogen atom as ring member, a radical selected from the group consisting of pyrrolidinyl, piperidinyl, piperazinyl, morpholinyl, and azepanyl, of which the heterocycloaliphatic moiety can in each case be unsubstituted or substituted by 1, 2, 3, 4, or 5 radicals $R^{57}$;

and $R^{57}$ stands for an alkyl radical selected from the group consisting of methyl, ethyl, n-propyl, isopropyl, tert-butyl, n-butyl, sec-butyl, and isobutyl;

in each case optionally in the form of one of the pure stereoisomers thereof, particularly enantiomers or diastereoisomers, or the racemates thereof or in the form of a mixture of stereoisomers, particularly the enantiomers and/or diastereoisomers, in an arbitrary mixing ratio, or in each case in the form of corresponding salts, or in each case in the form of corresponding solvates.

Very special preference is given to compounds of the general formula Ic,

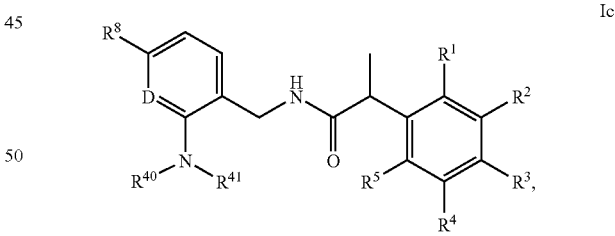

Ic in which

D stands for N or CH; $R^1$ stands for H; F; Cl; Br; or I;

$R^1$ stands for H; F; Cl; Br or I;

$R^2$ stands for H; F; Cl; Br; I; methyl; —OH; —$NH_2$ or —$OR^{16}$;

$R^3$ stands for H; F; Cl; Br; I; —$NO_2$; —OH; —$NH_2$; —NH—C(=O)—$R^{13}$, —$OR^{16}$; $SR^{17}$; —S(=O)—$NR^{22}R^{23}$ or —S(=O)—$R^{27}$;

$R^4$ stands for H; F; Cl; Br; I; methyl, —OH; —$NH_2$ or —$OR^{16}$;

$R^5$ stands for H; F; Cl; Br; or I;

$R^8$ stands for —$SF_5$; —O—$CF_3$; —$CF_3$; tert-butyl; or —$C(CH_3)_2(CH_2OH)$;

R$^{13}$, R$^{16}$, R$^{17}$, R$^{22}$, R$^{23}$ and R$^{27}$ each independently stand for a radical selected from the group consisting of methyl, ethyl, n-propyl, isopropyl, n-butyl, sec-butyl, isobutyl, tert-butyl, n-pentyl and ethenyl;

R$^{40}$ and R$^{41}$ form, together with the interconnecting nitrogen atom as ring member, a radical selected from the group consisting of pyrrolidinyl, piperidinyl, piperazinyl, morpholinyl, and azepanyl, of which the heterocycloaliphatic moiety can in each case be unsubstituted or substituted by 1, 2, 3, 4, or 5 radicals R$^{57}$;

and

R$^{57}$ stands for an alkyl radical selected from the group consisting of methyl, ethyl, n-propyl, isopropyl, tert-butyl, n-butyl, sec-butyl, and isobutyl;

in each case optionally in the form of one of the pure stereoisomers thereof, particularly enantiomers or diastereoisomers, or the racemates thereof or in the form of a mixture of stereoisomers, particularly the enantiomers and/or diastereoisomers, in an arbitrary mixing ratio, or in each case in the form of corresponding salts, or in each case in the form of corresponding solvates.

Even more preference is given to compounds of the general formulas I, Ia, Ib, and Ic selected from the group consisting of

[1] 2-(4-Amino-3-fluorophenyl)-N-((2-(4-methylpiperidin-1-yl)-6-(trifluoromethyl)pyridin-3-yl)methyl)propanamide;

[2] 2-(3,5-Dibromophenyl)-N-((2-(4-methylpiperidin-1-yl)-6-(trifluoromethyl)pyridin-3-yl)methyl)acetamide;

[3] 2-(4-Amino-3-bromo-5-methoxyphenyl)-N-((2-(4-methylpiperidin-1-yl)-6-(trifluoromethyl)pyridin-3-yl)methyl)acetamide;

[4] 2-(3-Fluorophenyl)-N-((2-(4-methylpiperidin-1-yl)-6-(trifluoromethyl)pyridin-3-yl)methyl)acetamide;

[5] 2-(2,4-Difluorophenyl)-N-((2-(4-methylpiperidin-1-yl)-6-(trifluoromethyl)pyridin-3-yl)methyl)acetamide;

[6] 2-(2,6-Difluorophenyl)-N-((2-(4-methylpiperidin-1-yl)-6-(trifluoromethyl)pyridin-3-yl)methyl)acetamide;

[7] 2-(2,5-Difluorophenyl)-N-((2-(4-methylpiperidin-1-yl)-6-(trifluoromethyl)pyridin-3-yl)methyl)acetamide;

[8] 2-(4-Fluorophenyl)-N-((2-(4-methylpiperidin-1-yl)-6-(trifluoromethyl)pyridin-3-yl)methyl)acetamide;

[9] 2-(4-Hydroxy-3-methoxyphenyl)-N-((2-(4-methylpiperidin-1-yl)-6-(trifluoromethyl)pyridin-3-yl)methyl)propanamide;

[10] 2-(3,5-Difluorophenyl)-N-((2-(4-methylpiperidin-1-yl)-6-(trifluoromethyl)pyridin-3-yl)methyl)propanamide;

[1,1] 2-(3,4-Difluorophenyl)-N-((2-(4-methylpiperidin-1-yl)-6-(trifluoromethyl)pyridin-3-yl)methyl)propanamide;

[12] 2-(4-Fluorophenyl)-N-((2-(4-methylpiperidin-1-yl)-6-(trifluoromethyl)pyridin-3-yl)methyl)propanamide;

[13] 2-(3-Fluorophenyl)-N-((2-(4-methylpiperidin-1-yl)-6-(trifluoromethyl)pyridin-3-yl)methyl)propanamide;

[14] 2-(3,4-Diaminophenyl)-N-((2-(4-methylpiperidin-1-yl)-6-(trifluoromethyl)pyridin-3-yl)methyl)propanamide;

[15] N-(2-Butoxy-6-tert-butylpyridin-3-ylmethyl)-2-(3,4-diamino-phenyl)-propionamide;

[16] N-((6-tert-Butyl-2-(4-methylpiperidin-1-yl)pyridin-3-yl)methyl)-2-(3,4-diaminophenyl)propanamide;

[17] N-((6-tert-Butyl-2-(cyclohexylthio)pyridin-3-yl)methyl)-2-(3,4-diaminophenyl)propanamide;

[18] 2-(4-Acetamido-3-fluorophenyl)-N-((2-(4-methylpiperidin-1-yl)-6-(trifluoromethyl)pyridin-3-yl)methyl)propanamide;

[19] 2-(3,5-Dibromo-4-hydroxyphenyl)-N-((2-(4-methylpiperidin-1-yl)-6-(trifluoromethyl)pyridin-3-yl)methyl)propanamide;

[20] 2-(4-Amino-3,5-dibromophenyl)-N-((2-(4-methylpiperidin-1-yl)-6-(trifluoromethyl)pyridin-3-yl)methyl)propanamide;

[21] 2-(3-Brom-4-hydroxy-5-methoxyphenyl)-N-((2-(4-methylpiperidin-1-yl)-6-(trifluoromethyl)pyridin-3-yl)methyl)acetamide;

[22] 2-(4-Amino-3,5-dibromophenyl)-N-((2-(4-methylpiperidin-1-yl)-6-(trifluoromethyl)pyridin-3-yl)methyl)acetamide;

[23] 2-(3,5-Dibromo-4-hydroxyphenyl)-N-((2-(4-methylpiperidin-1-yl)-6-(trifluoromethyl)pyridin-3-yl)methyl)acetamide;

[24] 2-(3-Amino-4-hydroxyphenyl)-N-((2-(4-methylpiperidin-1-yl)-6-(trifluoromethyl)pyridin-3-yl)methyl)propanamide; and

[25] 2-(3,5-Dibromophenyl)-N-(4-methyl-6'-trifluoromethyl-3,4,5,6-tetrahydro-2H-[1,2']bipyridinyl-3'-ylmethyl)acetamide;

[26] 2-(4-Amino-3,5-difluorophenyl)-N-((2-(4-methylpiperidin-1-yl)-6-(trifluoromethyl)pyridin-3-yl)methyl)propanamide,

[27] 2-(3-Fluoro-5-hydroxy-4-nitrophenyl)-N-((2-(4-methylpiperidin-1-yl)-6-(trifluoromethyl)pyridin-3-yl)methyl)propanamide,

[28] 2-(3-Chloro-4-(methylthio)phenyl)-N-((2-(4-methylpiperidin-1-yl)-6-(trifluoromethyl)pyridin-3-yl)methyl)propanamide,

[29] 2-(3-Chloro-4-(methylsulfonyl)phenyl)-N-((2-(4-methylpiperidin-1-yl)-6-(trifluoromethyl)pyridin-3-yl)methyl)propanamide,

[30] 2-(3-Fluoro-4-(methylthio)phenyl)-N-((2-(4-methylpiperidin-1-yl)-6-(trifluoromethyl)pyridin-3-yl)methyl)propanamide,

[31] 2-(3-Fluoro-4-(methylsulfonyl)phenyl)-N-((2-(4-methylpiperidin-1-yl)-6-(trifluoromethyl)pyridin-3-yl)methyl)propanamide,

[32] 2-(4-(N,N-Dimethylsulfamoyl)-3-fluorophenyl)-N-((2-(4-methylpiperidin-1-yl)-6-(trifluoromethyl)pyridin-3-yl)methyl)propanamide,

[33] N-(2-Fluoro-4-(1-((2-(4-methylpiperidin-1-yl)-6-(trifluoromethyl)pyridin-3-yl)methylamino)-1-oxopropan-2-yl)phenyl)acrylamide,

[34] N-(2-Fluoro-6-iodo-4-(1-((2-(4-methylpiperidin-1-yl)-6-(trifluoromethyl)pyridin-3-yl)methylamino)-1-oxopropan-2-yl)phenyl)acrylamide,

[35] 2-(4-Methoxy-3,5-dimethylphenyl)-N-((2-(4-methylpiperidin-1-yl)-6-(trifluoromethyl)pyridin-3-yl)methyl)propanamide,

[36] 2-(3,5-Difluoro-4-methoxyphenyl)-N-((2-(4-methylpiperidin-1-yl)-6-(trifluoromethyl)pyridin-3-yl)methyl)propanamide,

[37] 2-(4-Hydroxy-3,5-dimethylphenyl)-N-((2-(4-methylpiperidin-1-yl)-6-(trifluoromethyl)pyridin-3-yl)methyl)propanamide,

[38] 2-(3,5-Difluoro-4-hydroxyphenyl)-N-((2-(4-methylpiperidin-1-yl)-6-(trifluoromethyl)pyridin-3-yl)methyl)propanamide, each optionally in the form of one of the pure stereoisomers thereof, particularly enantiomers or diastereoisomers thereof, the racemates thereof or in the form of a mixture of stereoisomers, particularly the enantiomers and/or diastereoisomers, in an arbitrary mixing ratio, or each in the form of corresponding salts, or each in the form of corresponding solvates;

Furthermore, preference may be given to compounds of the invention of the general formulas I, Ia, Ib and Ic, which in the FLIPR assay using CHO-K1 cells, which have been transfected with the human VR1 gene in a concentration below 2000 nM, preferably below 1000 nM, more preferably below 300 nM, even more preferably below 100 nM, still more preferably below 75 nM, very preferably below 50 nM and most preferably below 10 nM, cause a 50 percent displacement of capsaicin present in a concentration of 100 nM. In the FLIPR assay, the $Ca^{2+}$ influx is quantified with the aid of a $Ca^{2+}$-sensitive dye (type Fluo-4, Molecular Probes Europe BV, Leiden, Netherlands) in a fluorescent imaging plate reader (FLIPR, Molecular Devices, Sunnyvale, USA), as described below.

The invention further relates to a process for the production of compounds of the above general formula I, according to which at least one compound of the general formula II,

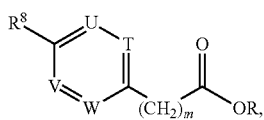

in which
$R^8$, U, T, V, and W have the aforementioned meanings, m stands for 0, 1, 2, or 3, and R stands for hydrogen or for a linear or branched $C_{1-6}$ alkyl radical, in a reaction medium, in the presence of at least one reducing agent, preferably in the presence of at least one reducing agent selected from the group consisting of sodium hydride, sodium, potassium hydride, lithium aluminum hydride, sodium tetrahydridoborate, and di(isobutyl)aluminum hydride
is converted to at least one compound of the general formula III,

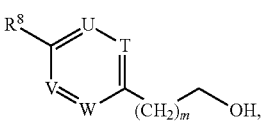

in which
$R^8$, U, T, V, and W have the meanings stated above and m stands for 0, 1, 2, or 3, and this is optionally purified and/or isolated,
and at least one compound of the general formula III is converted, in a reaction medium in the presence of diphenylphosphorylazide or in the presence of $HN_3$, to at least one compound of the general formula IV,

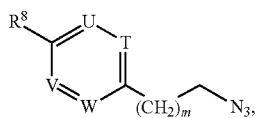

in which
$R^8$, U, T, V, and W have the meanings stated above and m stands for 0, 1, 2, or 3, and this is optionally purified and/or isolated,
and at least one compound of the general formula IV is converted, in a reaction medium in the presence of at least one reducing agent, preferably in the presence of at least one reducing agent selected from the group consisting of sodium hydride, potassium hydride, lithium aluminum hydride, sodium tetrahydridoborate, and di(isobutyl)aluminum hydride,
or in a reaction medium in the presence of a catalyst, preferably in the presence of a catalyst based on platinum or palladium, more preferably in the presence of palladium-on-charcoal, and in the presence of hydrogen or in the presence of hydrazine,
or in a reaction medium in the presence of triphenylphosphine to at least one compound of the general formula V,

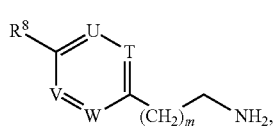

in which
$R^8$, U, T, V, and W have the meanings stated above and m stands for 0, 1, 2, or 3, and this is optionally purified and/or isolated,
or at least one compound of the general formula VI

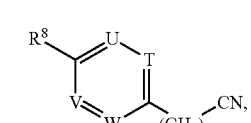

in which
$R^8$, U, T, V, and W have the meanings stated above and m stands for 0, 1, 2, or 3, in a reaction medium is converted, in the presence of at least one catalyst, preferably in the presence of at least one catalyst based on palladium or platinum, more preferably in the presence of palladium-on-charcoal, under a blanket of hydrogen, optionally in the presence of at least one acid, preferably in the presence of hydrochloric acid, or in the presence of at least one reducing agent selected from the group consisting of $BH_3$ bullet $S(CH_3)_2$, lithium aluminum hydride, and sodium tetrahydridoborate, optionally in the presence of $NiCl_2$,
to form at least one compound of the general formula V, optionally in the form of a corresponding salt, preferably in the form of a corresponding hydrochloride, and this is optionally purified and/or isolated,
and at least one compound of the general formula V is caused to react with at least one compound of the general formula VII,

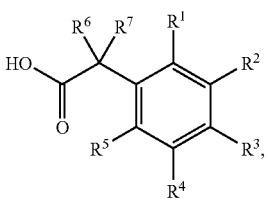

in which
$R^1, R^2, R^3, R^4, R^5, R^6,$ and $R^7$ have the meanings stated above, in a reaction medium, optionally in the presence of at least one suitable coupling agent, optionally in the presence of at least one base, or with at least one compound of the general formula VIII,

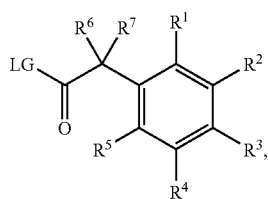
VIII in which
$R^1, R^2, R^3, R^4, R^5, R^6$, and $R^7$ have the meanings stated above and LG stands for a leaving group, preferably for a chlorine radical or bromine atom, in a reaction medium, optionally in the presence of at least one base, to form at least one compound of the general formula I,

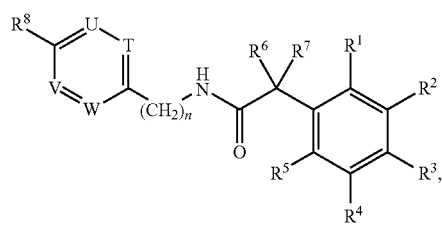
I in which
T, U, V, W, $R^1$, $R^2$, $R^3$, $R^4$, $R^5$, $R^6$, $R^7$, and $R^8$, have the meanings stated above and n stands for 1, 2, 3, or 4, and this is optionally purified and/or isolated.

The invention further relates to a process for the production of compounds of the above general formula I, according to which at least one compound of the general formula X,

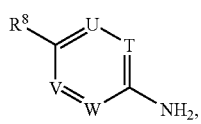
X in which
$R^8$, U, T, V, and W have the meanings stated above, is caused to react with at least one compound of the general formula VIII,

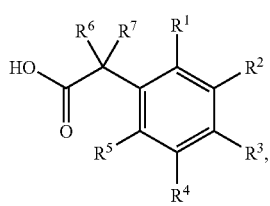
VII in which
$R^1$, $R^2$, $R^3$, $R^4$, $R^5$, $R^6$, and $R^7$, have the meanings stated above, in a reaction medium, optionally in the presence of at least one suitable coupling agent, optionally in the presence of at least one base, or with at least one compound of the general formula VIII,

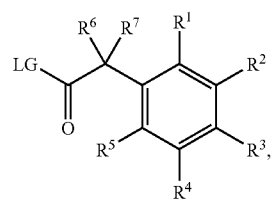
VIII in which
$R^1, R^2, R^3, R^4, R^5, R^6$, and $R^7$ have the meanings stated above and LG stands for a leaving group, preferably for a chlorine radical or bromine atom, in a reaction medium, optionally in the presence of at least one base,
to form at least one compound of the general formula Im,

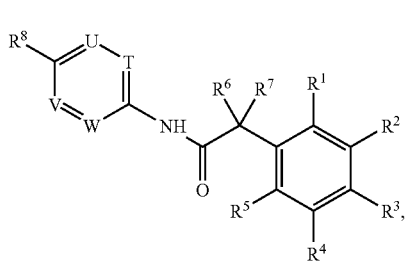
Im in which
T, U, V, W, $R^1$, $R^2$, $R^3$, $R^4$, $R^5$, $R^6$, $R^7$, and $R^8$ have the meanings stated above, and this is optionally purified and/or isolated.

The reaction of compounds of the above general formulas V or X with carboxylic acids of the above general formula VII to form compounds of the above general formulas I or Im is carried out preferably in a reaction medium selected from the group consisting of diethyl ether, tetrahydrofuran, acetonitrile, methanol, ethanol, (1,2)-dichloroethane, dimethylformamide, dichloromethane and appropriate mixtures thereof, optionally in the presence of at least one coupling agent, preferably selected from the group consisting of 1-benzotriazolyloxy-tris(dimethylamino)phosphonium hexafluorophosphate (BOP), dicyclohexylcarbodiimide (DCC), N'-(3-dimethylaminopropyl)-N-ethylcarbodiimide (EDCI), diisoproylcarbodiimide, 1,1'-carbonyldiimidazole (CDI), N-[(dimethylamino)-1H-1,2,3-triazolo[4.5-b]pyridino-1-yl-methylene]-N-methylmethanaminium hexafluorophosphate N-oxide (HATU), O-(benzotriazol-1-yl)-N,N,N',N'-tetramethyluronium hexafluorophosphate (HBTU), O(benzotriazol-1-yl)-N,N,N',N'-tetramethyluronium tetrafluoroborate (TBTU), N-hydroxybenzotriazole (HOBT), and 1-hydroxy-7-azabenzotriazole (HOAt), optionally in the presence of at least one organic base, preferably selected from the group consisting of triethylamine, pyridine, dimethylaminopyridine, N-methylmorpholine, and diisopropylethylamine, preferably at temperatures ranging from −70° C. to 100° C. Alternatively, the reaction of compounds of the above general formulas V or X with carboxylic derivatives of the above general formula VIII, in which LG stands for a leaving group, preferably for a chlorine radical or bromine atom, to form compounds of the above general formulas Im is carried out in a reaction medium preferably selected from the group consisting of diethyl ether, tetrahydrofuran, acetonitrile, methanol, ethanol, dimethylformamide, dichloromethane and appropriate mixtures thereof, optionally in the presence of an organic or inorganic base, preferably selected from the group consisting of triethylamine, dimethylaminopyridine, pyridine, and diisopropylamine, at temperatures ranging from −70° C. to 100° C.

The compounds of the above formulas II, III, IV, V, VI, VII, X and VIII are all commercially available and can be obtained by methods known to the person skilled in the art.

The synthesis of compounds of the general formula VII is described in the paper "4-(Methylsulfonylamino)phenyl analogues as vanilloid antagonist showing excellent analgesic activity and the pharmaceutical compositions comprising the same" by J. W. Lee et al. [WO 2005/003084-A1].

The appropriate sections of this reference are included herein by reference and are to be regarded as part of the disclosure.

The conversions described above can each be carried out under usual conditions well-known to the person skilled in the art, for example, in respect of pressure or order of addition of the components. Optionally, the optimal procedure under the respective conditions can be determined by the person skilled in the art using simple preliminary tests. The intermediates and end products obtained by the aforementioned reactions can in each case be isolated and/or purified by conventional methods known to the person skilled in the art, if desired and/or necessary. Suitable clean-up techniques are, for example, extraction processes and chromatographic processes such as column chromatography or preparative chromatography. All of the process steps described above and the purification and/or isolation of intermediate or end products can be carried out partially or completely under a blanket of inert gas, preferably under a blanket of nitrogen.

The substituted compounds of the invention of the aforementioned general formulas I, Ia, Ib and Ic, designated below simply as compounds of the general formula I, and corresponding stereoisomers can be isolated either in the form of the free bases thereof, the free acids thereof or in the form of corresponding salts, particularly physiologically acceptable salts.

The free bases of the respective substituted compounds of the invention of the aforementioned general formula I and corresponding stereoisomers can, for example by reaction with an inorganic or organic acid, preferably with hydrochloric acid, hydrobromic acid, sulfuric acid, phosphoric acid, methanesulfonic acid, p-toluenesulfonic acid, carbonic acid, formic acid, acetic acid, oxalic acid, succinic acid, tartaric acid, mandelic acid, fumaric acid, lactic acid, citric acid, glutamic acid, or aspartic acid, be converted to the corresponding salts, preferably physiologically acceptable salts. The free bases of the respective substituted compounds of the aforementioned general formula I and corresponding stereoisomers can be likewise caused to react with the free acid or a salt of a sugar substitute, such as saccharin, cyclamate, or acesulfam, to form the corresponding physiologically acceptable salts. Similarly, the free acids of the substituted compounds of the aforementioned general formula I and corresponding stereoisomers can be caused to react with of a suitable base to form the corresponding physiologically acceptable salts. Mention may be made, for example, of the alkali-metal salts, alkaline earth metal salts, or ammonium salts $[NH_xR_{4-x}]^+$ in which x is equal to 0, 1, 2, 3, or 4, and R stands for a linear or branched $C_{1-4}$ alkyl radical.

The substituted compounds of the invention designated by the aforementioned general formula I and corresponding stereoisomers can optionally, like the corresponding acids, the corresponding bases or salts of these compounds, be obtained in the form of the solvates thereof, preferably in the form of the hydrates thereof, by conventional methods known to the person skilled in the art.

If the substituted compounds of the invention designated by the aforementioned general formula I are obtained, following production thereof, in the form of a mixture of the stereoisomers thereof, preferably in the form of the racemates thereof or other mixtures of the various enantiomers and/or diastereoisomers thereof, these compounds can be separated and, if desired, isolated by methods known to the person skilled in the art.

Examples of suitable isolation methods include chromatographic separation methods, particularly liquid-chromatographic methods carried out under standard pressure or at elevated pressure, preferably MPLC and HPLC methods, and also methods of fractional crystallization. In particular, individual enantiomers can be separated from each other, e.g., diastereoisomeric salts formed by means of HPLC on chiral stationary phase or by means of crystallization with chiral acids, say, (+)-tartaric acid, (−)-tartaric acid, or (+)-10-camphorsulfonic acid.

The substituted compounds of the invention designated by the aforementioned general formula I and corresponding stereoisomers and in each case the corresponding acids, bases, salts, and solvates are toxicologically safe and are therefore suitable for use as pharmaceutically active substances in medicinal drugs.

The invention therefore further relates to a medicinal drug containing at least one compound of the invention of the above general formula I, each optionally in the form of one of the pure stereoisomers thereof, particularly enantiomers or diastereoisomers thereof, the racemates thereof or in the form of a mixture of stereoisomers, particularly the enantiomers and/or diastereoisomers, in an arbitrary mixing ratio, or each in the form of a corresponding salt, or each in the form of a corresponding solvate, and optionally one or more pharmaceutically compatible adjuvants.

These medicinal drugs of the inventions are particularly suitable for vanilloid receptor 1-(VR1/TRPV1) regulation, preferably vanilloid receptor 1-(VR1/TRPV1) inhibition and/or vanilloid receptor 1-(VR1/TRPV1) stimulation.

In another preferred embodiment, the medicinal drugs of the invention are suitable for prophylaxis and/or treatment of disorders or diseases that are at least partially mediated by vanilloid receptors 1.

Preferably, the medicinal drug of the invention is suitable for treatment and/or prophylaxis of one or more disorders selected from the group consisting of pain selected from the group consisting of acute pain, chronic pain, neuropathic pain and visceral pain; arthralgia; hyperalgesia; allodynia; causalgia; migraine; states of depression; nervous disorders; neurotraumas; neurodegenerative disorders, preferably selected from the group consisting of multiple sclerosis, Morbus Alzheimer, Morbus Parkinson, and Morbus Huntington; cognitive dysfunctions, preferably cognitive deficiency states, more preferably memory defects; epilepsy; respiratory tract diseases, preferably selected from the group consisting of asthma, bronchitis, and pneumonia; coughing; urinary incontinence; an overactive bladder (OAB); disorders and/or injuries of the gastrointestinal tract; duodenal ulcers; gastric ulcers; colitis syndrome; apoplectic strokes; eye irritations; cutaneous irritations; neurotic skin conditions; allergic skin diseases; psiorasis; vitiligo; Herpes simplex; inflammations, preferably inflammation of the intestine, the eyes, the bladder, the skin, or the nasal mucosa; diarrhea; pruritus; osteoporosis; arthritis; osteo-arthritis; rheumatic disorders; food intake disorders, preferably selected from the group consisting of bulimia, cachexia, anorexia, and obesity; medicine addiction; medicine abuse; withdrawal phenomena following medicine addiction; tolerance development to pharmaceuticals, particularly to natural or synthetic opioids; drug addiction; drug abuse; withdrawal phenomena following drug addiction; alcohol addiction; alcohol abuse and withdrawal phenomena following alcohol addiction; for diuresis; for antinatriuresis; for affection of the cardiovascular system; for vigilance enhancement; for treatment of wounds and/or burning; for treatment of severed nerves; for libido enhancement; for modulation of movement activity; for anxiolysis; for local anesthesia and/or for inhibition of undesirable side effects, preferably selected from the group consisting of hyperthermia, hypertension, and bronchial constriction, as caused by administration of vanilloid receptor 1 (VR1/TRPV1 receptor) agonists, preferably selected from the group consisting of capsaicin, resiniferatoxin, olvanil, arvanil, SDZ-249665, SDZ-249482, nuvanil, and capsavanil.

The medicinal drug of the invention is more preferably suitable for treatment and/or prophylaxis of one or more disorders selected from the group consisting of pain, preferably pain selected from the group consisting of acute pain, chronic pain, neuropathic pain, and visceral pain; arthralgia; migraine; states of depression; neurodegenerative disorders, preferably selected from the group consisting of multiple sclerosis, Morbus Alzheimer, Morbus Parkinson, and Morbus Huntington; cognitive dysfunctions, preferably cognitive deficiency states, more preferably memory defects; inflammation, preferably inflammation of the intestine, the eyes, the bladder, the skin or the nasal mucosa; urinary incontinence; an overactive bladder (OAB); medicine addiction; medicine abuse; withdrawal phenomena following medicine addiction; tolerance development to pharmaceuticals, preferably tolerance development to natural or synthetic opioids; drug addiction; drug abuse; withdrawal phenomena following drug addiction; alcohol addiction; alcohol abuse and withdrawal phenomena following alcohol addiction.

The medicinal drug of the invention is most preferably suitable for treatment and/or prophylaxis of pain, preferably pain selected from the group consisting of acute pain, chronic pain, neuropathic pain, and visceral pain, and/or urinary incontinence.

The invention further relates to the use of at least one compound of the invention and optionally one or more pharmaceutically compatible adjuvants for the production of a medicinal drug for vanilloid receptor 1-(VR1/TRPV1) regulation, preferably vanilloid receptor 1-(VR1/TRPV1) inhibition and/or vanilloid receptor 1-(VR1/TRPV1) stimulation.

Preference is given to the use of at least one substituted compound of the invention and optionally one or more pharmaceutically compatible adjuvants for the production of a medicinal drug for the prophylaxis and/or treatment of disorders or diseases which are at least partially mediated by vanilloid receptors 1.

Particular preference is given to the use of at least one compound of the invention and optionally one or more pharmaceutically compatible adjuvants for the production of a medicinal drug for treatment and/or prophylaxis of one or more disorders selected from the group consisting of pain, preferably of pain selected from the group consisting of acute pain, chronic pain, neuropathic pain, visceral pain, and arthralgia. Particular preference is given to the use at least one compound of the invention and optionally one or more pharmaceutically compatible adjuvants for the production of a medicinal drug for treatment and/or prophylaxis of one or more disorders selected from the group consisting of hyperalgesia; allodynia; causalgia; migraine; states of depression; nervous disorders; neurotraumas; neurodegenerative disorders, preferably selected from the group consisting of multiple sclerosis, Morbus Alzheimer, Morbus Parkinson, and Morbus Huntington; cognitive dysfunctions, preferably cognitive deficiency states, more preferably memory defects; epilepsy; respiratory tract diseases, preferably selected from the group consisting of asthma, bronchitis, and pneumonia; coughing; urinary incontinence; an overactive bladder (OAB); disorders and/or injuries of the gastrointestinal tract; duodenal ulcers; gastric ulcers; colitis syndrome; apoplectic strokes; eye irritations; cutaneous irritations; neurotic skin conditions; allergic skin diseases; psoriasis; vitiligo; Herpes simplex; inflammation, preferably inflammation of the intestine, the eyes, the bladder, the skin, or the nasal mucosa; diarrhea; pruritus; osteoporosis; arthritis; osteo-arthritis; rheumatic disorders; food intake disorders, preferably selected from the group consisting of bulimia, cachexia, anorexia, and obesity; medicine addiction; medicine abuse; withdrawal phenomena following medicine addiction; tolerance development to pharmaceuticals, preferably to natural or synthetic opioids; drug addiction; drug abuse; withdrawal phenomena following drug addiction; alcohol addiction; alcohol abuse and withdrawal phenomena following alcohol addiction; for diuresis; for antinatriuresis; for affection of the cardiovascular system; for vigilance enhancement; for treatment of wounds and/or burning; for treatment of severed nerves; for libido enhancement; for modulation of movement activity; for anxiolysis; for local anesthesia and/or for inhibition of undesirable side effects, preferably selected from the group consisting of hyperthermia, hypertension, and bronchial constriction, as caused by administration of vanilloid receptor 1 (VR1/TRPV1 receptor) agonists, preferably selected from the group consisting of capsaicin, resiniferatoxin, olvanil, arvanil, SDZ-249665, SDZ-249482, nuvanil, and capsavanil.

Very high preference is given to the use of at least one substituted compound of the invention and optionally one or more pharmaceutically compatible adjuvants for the production of a medicinal drug for treatment and/or prophylaxis of one or more disorders selected from the group consisting of pain, preferably pain selected from the group consisting of acute pain, chronic pain, neuropathic pain, and visceral pain; arthralgia; migraine; states of depression; neurodegenerative disorders, preferably selected from the group consisting of multiple sclerosis, Morbus Alzheimer, Morbus Parkinson, and Morbus Huntington; cognitive dysfunctions, preferably cognitive deficiency states, more preferably memory defects; inflammation, preferably inflammation of the intestine, the eyes, the bladder, the skin, or the nasal mucosa; urinary incontinence; an overactive bladder (OAB); medicine addiction; medicine abuse; withdrawal phenomena following medicine addiction; tolerance development to pharmaceuticals, preferably tolerance development to natural or synthetic opioids; drug addiction; drug abuse; withdrawal phenomena following drug addiction; alcohol addiction; alcohol abuse and withdrawal phenomena following alcohol addiction. Even more preference is given to the use of at least one substituted compound of the invention and optionally one or more pharmaceutically compatible adjuvants for the production of a medicinal drug for treatment and/or prophylaxis of pain, preferably selected from the group consisting of acute pain, chronic pain, neuropathic pain, and visceral pain, and/or urinary incontinence.

The medicinal drug of the invention is suitable for administration to adults and children including infants and babies.

The medicinal drug of the invention can exist as a liquid, semisolid, or solid pharmaceutical dosage form, for example, in the form of injection fluids, drops, juices, syrups, sprays, suspensions, tablets, patches, capsules, plasters, suppositories, ointments, creams, lotions, gels, emulsions, or aerosols, or in a multiparticular form, for example, in the form of pellets or granules, optionally compressed to tablets, filled into in capsules, or suspended in a liquid, and can be administered as such.

In addition to at least one substituted compound of the above general formula I, optionally in the form of a pure stereoisomer thereof, particularly an enantiomer or diastereoisomer, the racemate thereof or in the form of mixtures of the stereoisomers, particularly the enantiomers or diastereoisomers, in an arbitrary mixing ratio, or optionally in the form of a corresponding salt or each in the form of a corresponding solvate, the medicinal drug of the invention usually contains further physiologically acceptable pharmaceutical adjuvants, which, for example, can be selected from the group consisting of vehicles, fillers, solvents, diluents, surfactants, dyes, preservatives, blasting agents, slip agents, lubricants, flavors, and binding agents.

The selection of the physiologically acceptable adjuvants and the amount thereof to be used depends on whether the medicinal drug is to be applied orally, subcutaneously, parenterally, intravenously, intraperitoneally, intradermally, intramuscularly, intranasally, buccally, rectally or locally, e.g., to infected parts of the skin, the mucous membrane, or the eyes. Preparations suitable for oral administration are preferably in the form of tablets, dragees, capsules, granules, pellets, drops, juices, and syrups, and preparations suitable for parenteral, topical and inhalative administration are solutions, suspensions, readily reconstitutable dry preparations, and sprays. The substituted compounds of the invention used in the medicinal drug of the invention in a depot in dissolved form or in a plaster, optionally with the addition of skin penetration enhancing agents, are suitable percutane administration forms. Formulations for oral or percutane application may be such as to effect delayed release of the respective substituted compound of the invention. The production of the medicinal drug of the invention is effected by conventional means, devices, methods, and processes, as are known in the prior art, such as are described, for example, in "Remington's Pharmaceutical Sciences", Editor A. R. Gennaro, 17th Edition, Mack Publishing Company, Easton, Pa., 1985, particularly in Section 8, Chapters 76 to 93. The corresponding description is incorporated herein by reference and is to be regarded as part of the disclosure. The amount of the respective substituted compounds of the invention of the above general formula I to be administered to the patients can vary and is dependent, for example, on the weight or age of the patient and also on the method of administration, the indication, and the severity of the disorder. Usually from 0.001 to 100 mg/kg, preferably from 0.05 to 75 mg/kg and more preferably from 0.05 to 50 mg/kg, of body weight of the patient of at least one such compound of the invention are administered.

Pharmacological Methods:

I. Functional Investigation on the Vanilloid Receptor 1 (VR1/TRPV1 Receptor)

The agonistic or antagonistic action of the substances to be investigated on the vanilloid receptor 1 (VR1/TRPV1) of the species rat can be determined using the following assay. According to this assay, the $Ca^{2+}$ influx through the receptor channel is quantified with the aid of a $Ca^{2+}$-sensitive dye (Type Fluo-4, Molecular Probes Europe BV, Leiden Netherlands) in a fluorescent imaging plate reader (FLIPR, Molecular Devices, Sunnyvale, USA).

Method:

Complete medium: 50 mL of HAMS F12 Nutrient Mixture (Gibco Invitrogen GmbH, Karlsruhe, Germany) with 10% by volume of FCS (fetal calf serum, Gibco Invitrogen GmbH, Karlsruhe, Germany, heat-inactivated);

2 mM of L-glutamine (Sigma, Munich, Germany);

1% by weight of AA solution (antibiotics/antimycotics solution, PAA, Pasching, Austria)

and 25 ng/mL of Medium NGF (2.5 S, Gibco Invitrogen GmbH, Karlsruhe, Germany) Cell culture plate: Poly-D-lysine-coated, black 96-well plates with a clear bottom (96-well black/clear plate, BD Biosciences, Heidelberg, Germany) are additionally coated with laminin (Gibco Invitrogen GmbH, Karlsruhe, Germany) by diluting laminin to a concentration of 100 μg/mL with PBS (Ca—Mg-free PBS, Gibco Invitrogen GmbH, Karlsruhe, Germany). Aliquots having a concentration of 100 μg/mL of laminin are taken and stored at −20° C. The aliquots are diluted with PBS in the ratio 1:10 to 10 μg/mL of laminin and in each case 50 μL of the solution is pipeted into a well of the cell culture plate. The cell culture plates are incubated at 37° C. for at least two hours, the supernatant solution is aspirated and the wells are in each case washed twice with PBS. The coated cell culture plates are stored with supernatant PBS and this is removed only directly before the addition of the cells.

Preparation of the Cells:

The vertebral column is removed from decapitated rats and this is laid directly in a cold, i.e. ice bath-surrounded, HBSS buffer (Hank's buffered saline solution, Gibco Invitrogen GmbH, Karlsruhe, Germany) and 1% by volume of an M solution (antibiotics/antimycotics solution, PAA, Pasching, Austria) is added. The vertebral column is cut in two, longitudinally, and the vertebral canal is removed together with fascias. Subsequently, the dorsal root ganglia (DRGs) are removed and in turn stored in cold HBSS buffer to which 1% by volume of an AA solution has been added. The DRGs completely freed from blood residues and spinal nerves are in each case transferred to 500 μL of cold collagenase Type 2 (PAA, Pasching, Austria) and incubated at 37° C. for 35 minutes. After the addition of 2.5% by volume of trypsin (PAA, Pasching, Austria), the preparation is incubated at 37° C. for a further 10 minutes. On completion of incubation, the enzyme solution is carefully pipeted off and 500 μL of complete medium are added to the DRGs in each case. The DRGs are in each case repeatedly suspended, drawn through No. 1, No. 12, and No. 16 needles by means of a syringe and transferred to 50 mL Falcon tubes and these are filled to 15 mL with complete medium. The contents of each Falcon tube are in each case filtered through a 70 μm Falcon filter insert and centrifuged at 1200 rpm and RT for 10 minutes. The resulting pellet is in each case taken up in 250 μL of complete medium and the cell count is determined.

The number of cells in the suspension is adjusted to $3\times10^5$ per mL and in each case 150 μL of this suspension are added to a well of the cell culture plates coated as described above. The plates are allowed to stand at 37° C., 5% by volume of $CO_2$ and 95% relative humidity for two to three days in an incubator.

Subsequently, the cells are loaded with 2 μM of Fluo-4 and 0.01% by volume of Pluronic F127 (Molecular Probes Europe BV, Leiden Netherlands) in HBSS buffer (Hank's buffered saline solution, Gibco Invitrogen GmbH, Karlsruhe, Germany) at 37° C. for 30 min, washed 3 times with HBSS buffer and, after a further incubation of 15 minutes at RT, employed in the FLIPR assay for $Ca^{2+}$ measurement. The $Ca^{2+}$— dependent fluorescence is measured before and after addition of substances ($\lambda ex=488$ nm, $\lambda em=540$ nm). Quantification is carried out by measuring the highest fluorescence intensity (FC, fluorescence counts) over time.

FLIPR Assay:

The FLIPR protocol consists of two substance additions. Initially, the compounds to be tested (10 μM) are pipeted onto the cells and the $Ca^{2+}$ influx is compared with the control (capsaicin 10 μM). Information is gained therefrom in percentage activation relative to the $Ca^{2+}$ signal after addition of 10 μM of capsaicin (CP). After incubation for 5 minutes, 100 nM of capsaicin are applied and the influx of $Ca^{2+}$ is likewise determined.

Desensitizing agonists and antagonists lead to suppression of the $Ca^{2+}$ influx. The percentage inhibition is calculated in comparison with the maximum inhibition achieved with 10 μM of capsaicin. Conversion using the Cheng Prusoff equation gave $K_i$ values for the test substances (Cheng, Prusoff; Bioch. Pharmacol. 22, 3099-3108, 1973).

II. Functional Investigations on the Vanilloid Receptor (VR1)

The agonistic or antagonistic action of the substances to be examined on the vanilloid receptor (VR1) can alternatively be determined by the following assay. According to this assay the $Ca^{2+}$ influx through the canal is quantified with the aid of a $Ca^{2+}$-sensitive dye (type Fluo-4, Molecular Probes, Europe BV, Leiden, Netherlands) in a fluorescent imaging plate reader (FLIPR, Molecular Devices, Sunnyvale, USA).

Method:

Chinese hamster ovary cells (CHO-K1 cells, European Collection of Cell Cultures (ECACC) UK) are stably transfected with the VR1 gene. For carrying out functional investigations, these cells are plated on poly-D-lysine-coated, black 96-well plates with a clear bottom (BD Biosciences, Heidelberg, Germany) in a density of 25,000 cells/well. The cells are incubated overnight at 37° C. and 5% $CO_2$ in a culture medium (Nutrient Mixture 'am's F12, 10% by volume of FCS (fetal calf serum), 18 μg/mL of L-proline). On the following day the cells are incubated with Fluo-4 (Fluo-4 2 μM, Pluronic F127 0.01 by volume, Molecular Probes in HBSS (Hank's buffered saline solution), Gibco Invitrogen GmbH, Karlsruhe, Germany) for 30 minutes at 37° C. The plates are then washed 3 times with HBSS buffer and, after another incubation over a period of 15 minutes at RT, are used in the FLIPR for $Ca^{2+}$ measurement. The $Ca^{2+}$-dependent fluorescence is measured prior to and following the addition of the substances being examined (wavelength λex=488 nm, λem=540 nm). Quantification is carried out by measuring the highest fluorescence intensity (PC, fluorescence counts) over time.

FLIPR Assay:

The FLIPR protocol consists of two substance additions. First of all, the substances to be tested (10 μM) are pipeted onto the cells and the $Ca^{2+}$ influx is compared with the control (capsaicin 10 μM) (percentage activation based on the $Ca^{2+}$ signal following addition of 10 μM of capsaicin). Following incubation over a period of 5 minutes 100 nM of capsaicin are applied and the influx of $Ca^{2+}$ is likewise determined.

Desensitizing agonists and antagonists lead to a suppression of the $Ca^{2+}$ influx. The percentage inhibition compared with the maximum inhibition achieved with 10 μM of capsaicin is calculated.

Based on the percentage displacement effected by different concentrations of the compounds of the general formula I to be tested, $IC_{50}$ inhibition concentrations that cause 50 percent displacement of capsaicin are calculated. Conversion using the Cheng Prusoff equation gave $K_i$ values for the test substances (Cheng, Prusoff; Bioch. Pharmacol. 22, 3099-3108, 1973).

III. Formalin Test on Mice

The investigation for the determination of the antinociceptive action of the compounds of the invention is carried out in the formalin test on male mice (NMRI, of 20 to 30 g body weight, Iffa, Credo, Belgium).

In the formalin test, the first (early) phase (0 to 15 minutes after the formalin injection) and the second (late) phase (15 to 60 minutes after the formalin injection) are distinguished according to D. Dubuisson et al., Pain 1977, 4, 161-174. The early phase, as a direct reaction to the formalin injection, is a model of acute pain, whereas the late phase is regarded as a model of persistent (chronic) pain (T. J. Coderre et al., Pain 1993, 52, 259-285). The appropriate literature references are incorporated herein by reference and are to be regarded as part of the disclosure.

The compounds of the invention are examined in the second phase of the formalin test, in order to obtain information concerning a substance's action on chronic/inflammatory pain.

The point in time of administration of the compounds of the invention before the formalin injection is selected according to the method of administration of the compounds of the invention. Intravenous administration of 10 mg/kg of body weight of the test substance is carried out 5 minutes before the formalin injection. This is carried out by a single subcutaneous formalin injection (20 μL, 1% strength aqueous solution) into the dorsal side of the right hind paw so that in the case of free-moving experimental animals a nociceptive reaction is induced which is manifested by marked licking and biting of the relevant paw.

The nociceptive behavior is then continuously registered during an investigation period of three minutes in the second (late) phase of the formalin test (21 to 24 minutes after the formalin injection) by observation of the animals. Quantification of the pain behavior is carried out by summating the seconds during which the animals show licking and biting of the relevant paw during the investigation period. In each case, comparison is carried out with control animals, which receive, instead of the compounds of the invention, a vehicle (0.9% strength aqueous sodium chloride solution) prior to formalin administration. Based on the quantification of the pain behavior, the substance's action in the formalin test is determined as the degree of change compared with the corresponding control.

Following injection of the substances having an antinociceptive action in the formalin test, the aforementioned behavioral patterns of the animals, i.e. licking and biting, decrease or cease.

IV. Test for Analgesic Effectiveness in the Writhing Test

Investigation of the compounds of the general formula I of the invention for analgetic effectiveness was carried out based on phenylquinone-induced writhing in mice, modified after I. C. Hendershot and J. Forsaith (1959) J. Pharmacol. Exp. Ther. 125, 237-240. The corresponding literature reference is incorporated herein by reference and is to be regarded as part of the disclosure.

For this purpose, male NMRI mice having a weight of from 25 to 30 g were used. Groups of 10 animals per dose of the test compound received by intraperitoneal administration, 10 minutes after intravenous administration of the compound under test, 0.3 mL/mouse of a 0.02% strength aqueous solution of phenylquinone (phenylbenzoquinone, marketed by Sigma, Deisenhofen, Germany and produced by adding to the solution 5% by weight of ethanol and storing it in a water bath at 45° C.). The animals were placed individually in observation cages. With the aid of a pushbutton counter, the number of pain-induced stretching movements (so-called writhing reactions—straightening of the body with stretching of the rear extremities) was counted over a period of from 5 to 20 minutes following the administration of the phenylquinone.

The control was provided by animals receiving only physiological saline. All of the compounds were tested using the standard dosage of 10 mg/kg.

V. Hypothermia Assay in Mice

Description of the Method:

The hypothermia assay was carried out on male NMRI mice (weight 25-35 gram, Zuechter IFFA CREDO, Brussels, Belgium). The animals were kept under standardized conditions: light/dark rhythm (from 6:00 to 18:00 hours light phase; from 18:00 to 6:00 hours dark phase), RT 19-22° C., relative air humidity 35-70%, 15 air changes per hour, air movement <0.2 m/sec. The animals received standard feed (ssniff R/M−Haltung, ssniff Spezialdiaeten GmbH, Soest, Germany) and tap water. Water and feed were withdrawn during the experiment. All animals were used only once during the experiment. The animals had an acclimatization period of at least 5 days.

Acute administration of capsaicin (VR-1 agonist) leads to a drop in the core temperature of the body in rats and mice due to stimulation of heat sensors. Only specifically effective VR-1 receptor antagonists can antagonize the capsaicin-induced hypothermia. By contrast, hypothermia induced by morphine is not antagonized by VR-1 antagonists. This model is therefore suitable for identifying substances with VR-1 antagonistic properties via their effect on body temperature.

Measurement of the core temperature is carried out using a digital thermometer (Thermalert TH-5, physitemp, Clifton N.J., USA). The sensing element is inserted into the rectum of the animals.

To give an individual basic value for each animal, the body temperature is measured twice at an interval of approximately half an hour. One group of animals (n=6 to 10) then receives an intraperitoneal (i.p.) application of capsaicin 3 mg/kg and vehicle (control group). Another group of animals receives the substance to be tested (i.v. or p.o.) and additionally capsaicin (3 mg/kg) i.p. The administration of the test substance is carried out i.v. 10 min, or p.o 15 minutes, prior to capsaicin. The body temperature is then measured 7.5/15 and 30 min following capsaicin (i.v.+i.p.) or 15/30/60/90/120 min (p.o.+ i.p.) following capsaicin. In addition, one group of animals is treated with the test substance only and one group with vehicle only. The evaluation or representation of the measured values as mean+/−SEM of the absolute values is presented as a graphical representation. The antagonistic action is calculated as the percentage reduction of the capsaicin-induced hypothermia.

VI. Neuropathic Pain in Mice

The investigation on effectiveness on neuropathic pain was examined using the Bennett Model (chronic constriction injury; Bennett und Xie, 1988, Pain 33:87-107). Three loose ligatures are tied around the right ischiadic nerve of Ketavet/Rompun-anesthetized NMRI mice weighing 16-18 g. The animals develop hypersensitivity of the nervate paw caused by the damaged nerve, which hypersensitivity is quantified, following a recovery phase of one week, over a period of approximately three weeks by means of a cold metal plate (temperature 4° C.) (cold allodynia). The animals are observed on this plate over a period of 2 min, and the withdrawal reactions of the damaged paw are counted. Based on the pre-value prior to administration of substance, the substance's action over a certain period of time is determined at various points in time (e.g., 15, 30, 45, or 60 min following administration) and the resultant area under the curve (AUC) and/or the inhibition of cold allodynia at the individual measuring points was/were expressed as percentage action relative to the vehicle control (AUC) or to the starting value (individual measuring points). The group size is n=10, the significance of an anti-allodynic action (*=p<0.05) is determined with the aid of an analysis of variance with repeated measures and Bonferroni post hoc analysis.

The invention is described below with reference to some examples. These explanations are by way of example only and do not restrict the general inventive concept.

EXAMPLES

The yields of the compounds produced were not optimized. All temperatures are uncorrected. The statement "equivalents" denotes mol equivalents, "RT" room temperature, "M" and "N" are concentrations in mol/L, "aq." aqueous, "sat." saturated, "soln. solution, and other abbreviations are:

| | |
|---|---|
| AvOH | acetic acid |
| DCM | dichloromethane |
| DMF | N,N-dimethylformamide |
| EDCl | N-ethyl-N'-(3-dimethylaminopropyl)carbodiimide hydrochloride |
| EA | ethyl acetate |
| H$_2$O | water |
| HOBt | N-hydroxybenzotriazole |
| MeOH | methanol |
| THF | tetrahydrofuran |

The chemicals and solvents used were obtained commercially from the usual suppliers (Acros, Avocado, Aldrich, Bachem, Fluka, Lancaster, Maybridge, Merck, Sigma, TCI, Oakwood etc.) or synthesized by usual methods known to the person skilled in the art.

The stationary phase used for column chromatography was silica gel 60 (0.0-0-0.063 mm) supplied by E. Merck, Darmstadt.

The thin-layer chromatographic analyses were carried out using preformed HPTLC plates, Silica Gel 60 F 254, supplied by E. Merck, Darmstadt.

The mixing ratios of solvents, mobile solvents, or for chromatographic analyses are always stated in vol/vol.

Chemical analysis was carried out by mass spectroscopy and NMR.

1. General Instructions for Preparing Amines of the General Formula V-A

Preparation of Amines of the General Formula V-A is Carried Out as Illustrated by the following scheme 1.

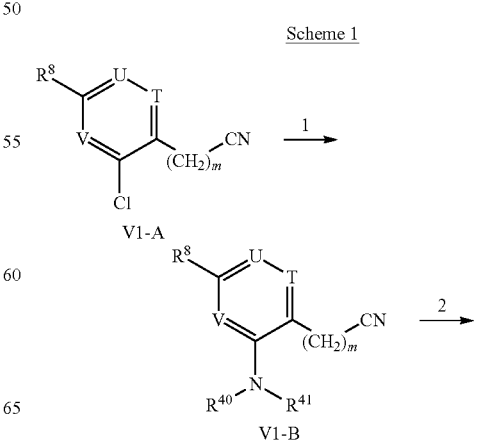

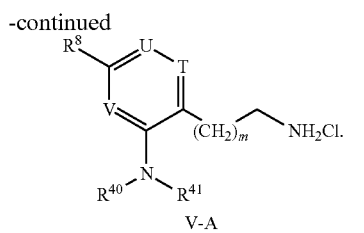

Stage 1: Preparation of Nitrites of the General Formula VI-B

Method A:

Compounds of the general formula VI-A (1 equivalent), in which $R^8$, U, T, and V have the meanings stated above and m stands for 0, 1, 2, or 3, are stirred with an amine of the general formula $HNR^{40}R^{41}$ (6 equivalents) over a period of 48 hours at RT. To the reaction mixture there is added 1N hydrochloric acid, and the mixture is extracted with EA a number of times. The aqueous phase is saturated with NaCl and then again extracted with EA. The combined organic phases are washed with 1N hydrochloric acid and with sat. aq. NaCl soln., dried over $MgSO_4$, and the solvent is removed in vacuo. The following compound was obtained by method A:

6'-tert-Butyl-4-methyl-3,4,5,6-tetrahydro-2H-[1,2']bipyridinyl-3'-carbonitrile

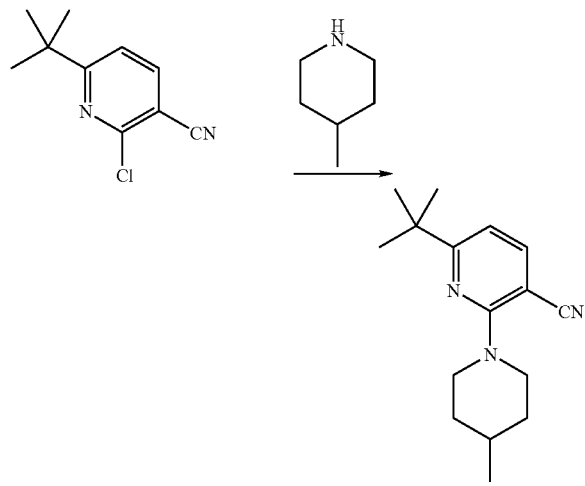

$^1$H-NMR ($CDCl_3$) δ 7.65 (d, 1H, J=7.9 Hz, Ar), 6.70 (d, 1H, J=8.0 Hz, Ar), 4.45 (m, 2H, piperidine), 2.98 (m, 2H, piperidine), 1.75-1.24 (m, 5H, piperidine), 1.29 (s, 9H, $C(CH_3)_3$), 0.98 (d, 3H, J=5.9 Hz, $CHCH_3$)

IR 2956, 2213, 1583, 1550, 1452, 1230, 965 $cm^{-1}$

Method B:

Compounds of the general formula VI-A (1 equivalent), in which $R^8$, U, T, and V have the meanings stated above and m stands for 0, 1, 2, or 3, are stirred with an amine of the general formula $HNR^{40}R^{41}$ (2 equivalents) and DBU [1.8-diaza-bicyclo[5.4.0]undec-7-ene] (2 equivalents) in acetonitrile (7 mL per mmol of the compound of formula VI-A) over a period of 12 hours at RT. The reaction mixture is extracted with EA a number of times. The combined organic phases are washed with sat. aq. NaCl solution, dried over $MgSO_4$, and the solvent is removed in vacuo. The residue is purified in each case by column chromatography ($SiO_2$, various mixtures of hexane/EA). The following compound was produced by method B.

6-(Trifluoromethyl)-2-(4-methylpiperidin-1-yl)pyridine-3-carbonitrile

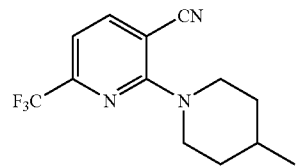 [SMILES: CC1CCN(c2nc(C(F)(F)F)ccc2C#N)CC1]

$^1$H NMR (300 M Hz, $CDCl_3$) δ 7.87 (d, 1 h, J=7.8 Hz), 6.95 (d, 1 h, J=7.8 Hz), 4.53 (m, 2H), 3.05 (m, 2H), 1.78 (m, 2H), 1.64 (m, 1H), 1.29 (m, 2H), 1.00 (d, 3H, J=6.6 Hz); IR (PUR) 2926, 2852, 2218, 1590, 1497, 1456, 1324, 1237, 1186, 1147, 1082, of 963 $cm^{-1}$; MS (FAB) m/z 270 (M+H)

Step 2:

Method 1

Compounds of the general formula VI-B (5 mmol), in which $R^8$, $R^{40}$, $R^{41}$, U, T, and V have the meanings stated above and m stands for 0, 1, 2, or 3, palladium-on-charcoal (10%, 500 mg) and conc. hydrochloric acid (3 mL) are dissolved in MeOH (30 mL) and exposed to a hydrogen atmosphere over a period of 6 hours at RT. The reaction mixture is filtered over Celite and the filtrate is concentrated in vacuo. The residue is purified by means of flash chromatography ($SiO_2$, EA).

Method 2:

Compounds of the general formula VI-B (2 mmol), in which $R^8$, $R^{40}$, $R^{41}$, U, T, and V have the meanings stated above and m stands for 0, 1, 2, or 3, are dissolved in THF (10 mL, 10 mL), and $BH_3.S(CH_3)_2$ [2.0 M in THF, 3 mL, 3 equivalents] is added. The reaction mixture is heated under reflux over a period of 8 hours, aq. HCl (2N) is added and the reaction mixture is again heated under reflux for 30 minutes. Aq. sodium hydroxide solution (2N) is added to the reaction mixture, and the mixture is washed with EA. The combined organic phases are washed with sat. aq. NaCl solution and dried over magnesium sulfate. The solvent is removed in vacuo and the residue purified by column chromatography ($SiO_2$, various mixtures of dichloromethane and MeOH as mobile solvent). The following compounds were obtained by method 2.

(6-(Trifluoromethyl)-2-(4-methylpiperidin-1-yl)pyridin-3-yl)methanamine

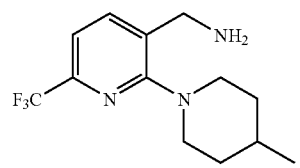 [SMILES: CC1CCN(c2nc(C(F)(F)F)ccc2CN)CC1]

$^1$H NMR (300 M Hz, $CDCl_3$) δ 7.89 (d, 1H, J=7.8 Hz), 7.33 (d, 1H, J=7.8 Hz), 3.88 (s, 2H), 3.39 (m, 2H), 2.83 (m, 2H), 1.75 (m, 2H), 1.55 (m, 1H), 1.38 (m, 2H), 1.00 (d, 3H, J=6.6 Hz); MS (FAB) m/z 274 (M+H)

C-(6'-tert-Butyl-4-methyl-3,4,5,6-tetrahydro-2H-[1,2']bipyridinyl-3'-yl)-methylamine

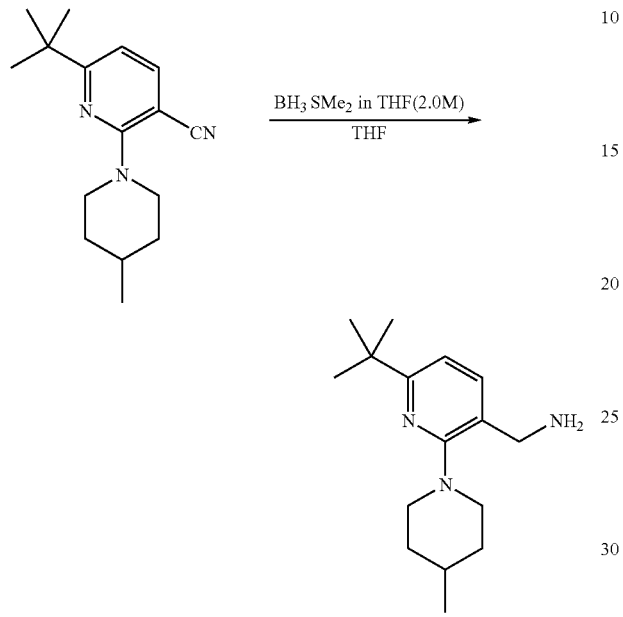

$^1$H-NMR (CDCl$_3$) δ 7.48 (d, 1H, J=7.7 Hz, Ar), 6.90 (d, 1H, J=7.7 Hz, Ar), 3.82 (s, 2H, CH$_2$NH$_2$), 3.38 (m, 2H, piperidine), 2.81 (m, 2H, piperidine), 1.73-1.28 (m, 5H, piperidine), 1.31 (s, 9H, C(CH$_3$)$_3$), 0.98 (d, 3H, J=6.4 Hz, CHCH$_3$)

IR 3363, 2954, 1571, 1451, 1400, 1372, 1234, 960 cm$^{-1}$

2. General Instructions for the Preparation of Amines of the General Formula V-E The preparation of amines of the general formula V-E is carried out as illustrated in the following scheme 2.

Scheme 2

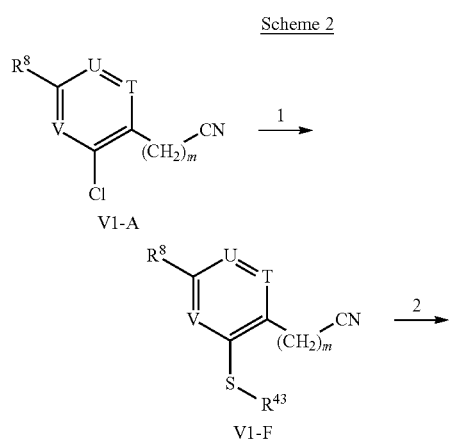

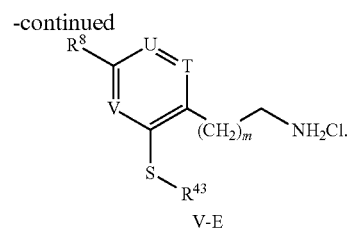

Step 1

Synthesis of 2-(cyclohexylthio)-6-(trifluoromethyl) nicotinonitrile

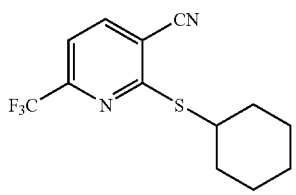 [SMILES: N#Cc1ccc(C(F)(F)F)nc1SC1CCCCC1]

1.3 Equivalents of NaH (4.9 g, 0.124 mol) were dissolved in 50 mL of DMF under a blanket of nitrogen. Following the addition of 1.2 equivalents of cyclohexanethiol (14.2 mL, 0.116 mol), the mixture was stirred at RT over a period of 1.5 h. The resulting suspension was cooled to 10° C. and added dropwise to 1 equivalent of 2-chloro-6-(trifluoromethyl) nicotinonitrile (20 g, 0.096 mol) in 50 mL of DMF and stirred over a period of 2 h at RT. To the reaction mixture there was added sat. aq. NH$_4$Cl soln. and the mixture was diluted with 1 L of water and extracted with EA (3×200 mL). The combined organic phases were washed with sat. aq. NaCl solution, dried over MgSO$_4$ and concentrated in vacuo. Column chromatographic purification (silica gel 100-200 mesh, eluant: 2% EA in hexane) yielded 26 g (93.8%) of product.

$^1$H NMR (300 M Hz, CDCl$_3$) δ 7.94 (d, 1H, J=7.9 Hz), 7.34 (d, 1H, J=7.9 Hz), 4.00 (m, 1H), 1.90-2.14 (m, 2H), 1.42-1.88 (m, 8H)

IR (neat) 2930, 2854, 2232, 1643, 1573, 1447, 1334, 1245, 1186, 1149, 1107, 851 cm$^{-1}$ MS (FAB) m/z 287 (M+H)

Step 2

Synthesis of (2-(cyclohexylthio)-6-(trifluoromethyl)-pyridin-3-yl)methanamine dihydrochloride The nitrile (26 g, 0.091 mol) was dissolved in 600 mL of THF under a blanket of nitrogen and cooled to 5° C. BH$_3$-dimethyl sulfide (13.78 g, 0.182 mol) was added dropwise and the mixture was boiled under reflux over a period of 20 h. After cooling to 5° C., 100 mL of MeOH were added to the reaction batch and the mixture was stirred at RT over a period of 15 minutes. Di-tert-butyldicarbonate (29.7 g, 0.136 mol) was then added and the mixture was stirred at RT for 30 min. Following the removal of the solvent in vacuo, the crude product was purified by column chromatography (silica gel 100-200 mesh, eluant: 10% EA in hexane) and 23.4 g (66%) of product were obtained. The crude product was dissolved in 120 mL of sat. HCl/dioxane soln., and the solution was stirred at RT over a period of 6 h. Following the removal of the solvent in vacuo, the solid matter was washed with 10% of EA in hexane (2×100 mL) and isolated by filtration. Yield: 17 g (88.8%)

$^1$H NMR (DMSO-d$_6$, 400 M Hz): δ 8.8 (s, 2H), 8.05 (d, 1H), 7.76 (d, 1H), 4.01 (s, 1H), 3.86-3.93 (m, 1H), 2.02-2.08 (m, 2H), 1.71-1.74 (m, 2H), 1.40-1.60 (m, 6H).

3. General Instructions for the Preparation of Amines of the General Formula V-B The preparation of amines of the general formula V-B is carried out as illustrated in the following scheme 3.

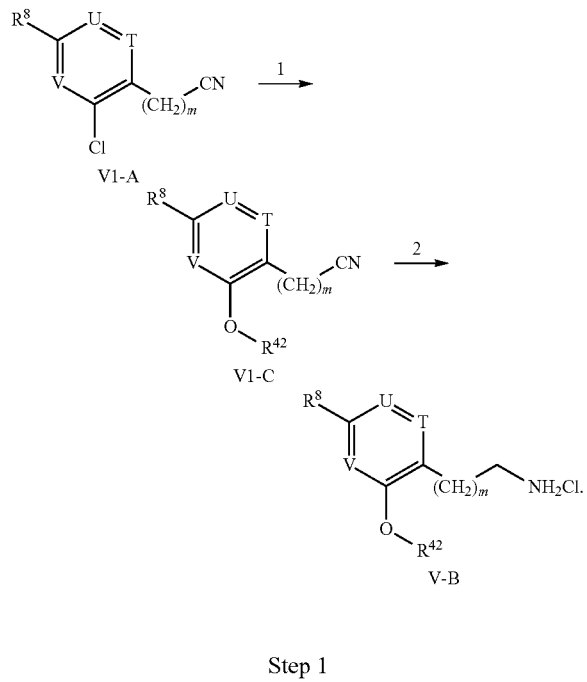

Scheme 3

Step 1

Preparation of Nitriles of the General Formula VI—C

Compounds of the general formula VI-A (1 equivalent), in which R$^8$, U, T, and V have the meanings stated above and m stands for 0, 1, 2, or 3, are stirred with an alcohol of the general formula HO—R$^{42}$ (3.5 equivalents) and DBU [1,8-diaza-bicyclo[5.4.0]undec-7-ene] (3.5 equivalents) in acetonitrile (7 mL per mmol of the compound of formula VI-A) over a period of 12 hours at RT. The reaction mixture is extracted with EA a number of times. The combined organic phases are washed with sat. aq. NaCl soln. and dried over MgSO$_4$, and the solvent is removed in vacuo. The residue is purified in each case by column chromatography (SiO$_2$, various mixtures of hexane/EA).

Method 2:

Compounds of the general formula VI—C (2 mmol), in which R$^8$, R$^{42}$, U, T, and V have the meanings stated above and m stands for 0, 1, 2, or 3, are dissolved in THF (10 mL, 10 mL) and BH$_3$·S(CH$_3$)$_2$ [2.0 M in THF, 3 mL, 3 equivalent] is added. The reaction mixture is heated under reflux over a period of 8 hours, aq. HCl (2N) is added and the reaction mixture is again heated under reflux for 30 minutes. Aq. sodium hydroxide solution (2N) is added to the reaction mixture, and the mixture is washed with EA. The combined organic phases are washed with sat. aq. NaCl solution and dried over magnesium sulfate. The solvent is removed in vacuo and the residue is purified by column chromatography (SiO$_2$, various mixtures of dichloromethane and methanol as mobile solvent).

Method 3:

Compounds of the general formula VI—C (1.5 mmol), in which R$^8$, R$^{42}$, U, T, and V have the meanings stated above and m stands for 0, 1, 2, or 3, are dissolved in diethyl ether (3 mL) and a suspension of lithium aluminum hydride (3 mmol) in ether (5 mL) is slowly added dropwise at 0° C. The reaction mixture is heated under reflux over a period of 4 hours and methanol followed by 1N aq. NaOH solution are slowly added dropwise at 0° C. The reaction mixture is diluted with methanol and filtered over Celite. The solvent is removed in vacuo and the residue is purified by column chromatography (SiO$_2$, various mixtures of dichloromethane and methanol as mobile solvent).

4. General Instructions for the Preparation of Amines of the General Formula V—C The preparation of amines of the general formula V—C is carried out as illustrated in the following scheme 4.

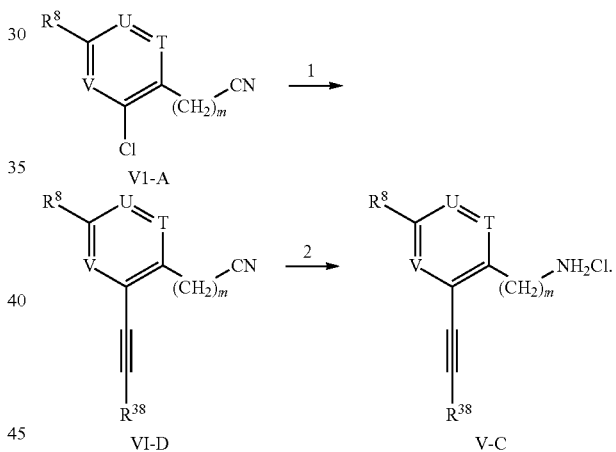

Scheme 4

Step 1

Preparation of Nitrites of the General Formula VI-D

Compounds of the general formula VI-A (1 equivalent), in which R$^8$, U, T, and V have the meanings stated above and m stands for 0, 1, 2, or 3, are dissolved together with bis(triphenylphosphine)palladium dichloride (7 mol %) and copper(I) iodide (14 mol %) in 1-methyl-2-pyrrolidinone (7 mL per mmol of the compound of the general formula VI-A). Following a period of 10 minutes the alkyne of the general formula HC≡R$^{38}$ (3.5 equivalents) and N,N-diisopropylethylamine (2 equivalents) are added, and the reaction mixture is stirred over a period of 12 h at a temperature between 90 and 110° C. The reaction mixture is filtered over Celite and extracted with EA a number of times. The combined organic phases are washed with sat. aq. NaCl solution, dried over MgSO$_4$, and the solvent is removed in vacuo. The residue is purified in each case by column chromatography (SiO$_2$, various mixtures of hexane/EA).

5. General Instructions for the Preparation of Amines of the General Formula V-D The preparation of amines of the general formula V-D is carried out as illustrated in the following scheme 5.

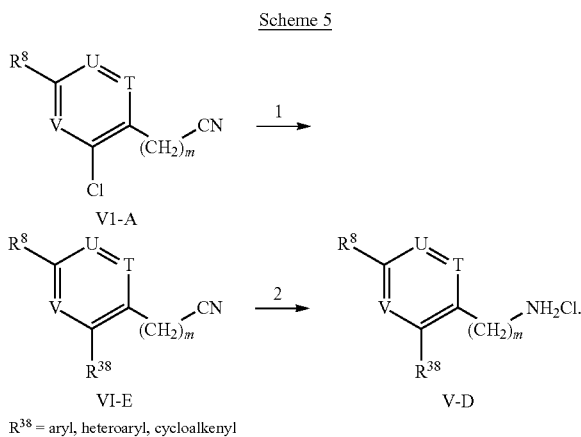

Scheme 5

$R^{38}$ = aryl, heteroaryl, cycloalkenyl

Step 1

Preparation of Nitrites of the General Formula VI-E

Compounds of the general formula VI-A (1 equivalent), in which $R^8$, U, T, and V have the aforementioned meanings and m stands for 0, 1, 2, or 3, are stirred with palladium dichloride (5 mol %) and a compound of the general formula $R^{38}$—B$(OH)_2$ (2 equivalents), in which $R^{38}$ stands for aryl, heteroaryl, or cycloalkenyl, in a solvent mixture of toluene/dioxane/2N aq. sodium carbonate solution (20 mL per 1 mmol of compounds of the general formula VI-A). The reaction mixture is heated under reflux over a period of 12 h and filtered over Celite. The combined organic phases are dried over magnesium sulfate, and the solvent is removed in vacuo. The residue is purified by column chromatography ($SiO_2$, various solvent mixtures of hexane and EA).

Step 2

Method 1:
Compounds of the general formula VI-E (5 mmol), in which $R^8$, $R^{38}$, U, T, and V have the meanings stated above and m stands for 0, 1, 2, or 3, palladium-on-charcoal (10%, 500 mg) and conc. hydrochloric acid (3 mL) are dissolved in MeOH (30 mL) and exposed to a hydrogen atmosphere over a period of 6 hours at RT. The reaction mixture is filtered over Celite and the filtrate is concentrated in vacuo. The residue is purified by means of flash chromatography ($SiO_2$, EA).
Method 2:
Compounds of the general formula VI-E (2 mmol), in which $R^8$, $R^{38}$, U, T, and V have the meanings stated above and m stands for 0, 1, 2, or 3, are dissolved in THF (10 mL, 10 mL), and $BH_3 \cdot S(CH_3)_2$ [2.0 M in THF, 3 mL, 3 equivalent] is added. The reaction mixture is heated under reflux over a period of 8 hours, aq. HCl (2N) is added and the reaction mixture is again heated under reflux for 30 minutes. Aq. sodium hydroxide solution (2N) is added to the reaction mixture, and the mixture is washed with EA. The combined organic phases are washed with sat. aq. NaCl solution and dried over magnesium sulfate. The solvent is removed in vacuo and the residue is purified by column chromatography ($SiO_2$, various mixtures of dichloromethane and methanol as mobile solvent).

6. Preparation of Certain Acids

Synthesis of
2-(3-halogenated-4-(methylthio)phenyl)propanoic acids (cf. Examples 28, 29)

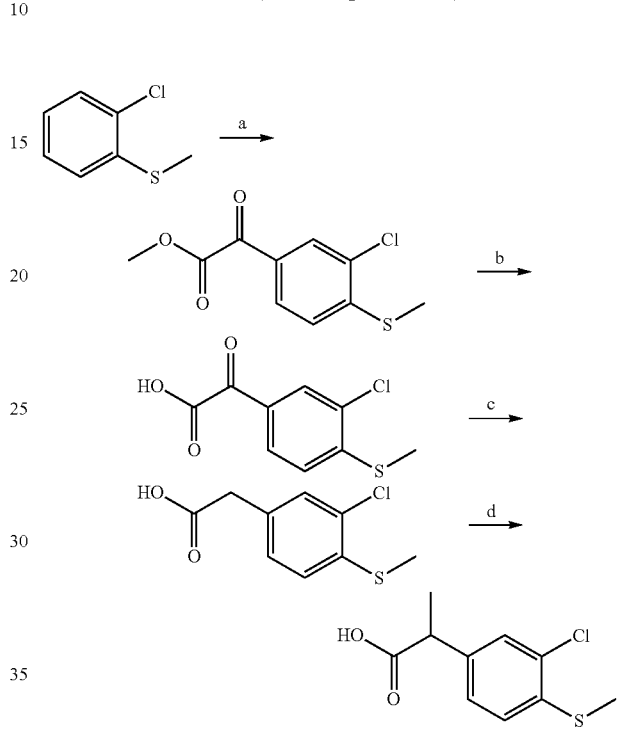

a. Methyl 2-chloro-2-oxoacetate, $AlCl_3$, $CHCl_3$, 0-25° C.;
b. aq. NaOH, toluene, 60° C., 1.5 h;
c. hydrazine hydrate, KOH, -50-100° C.;
d. $CH_3I$, hexane, LDA, TMEDA, -78° C., 3 h The preparation of substituted methylthiophenylpropanoic acids is performed as described in US2003/225283. A solution of $AlCl_3$ (54.9 g, 412 mmol) in chloroform (180 mL) is cooled to 0° C. under argon atmosphere. A solution of methyl-2-chloro-2-oxoacetate (24.3 mL, 264 mmol) in chloroform (180 mL) is added dropwise and the mixture is stirred for 30 min at 0° C. after addition. A solution of 2-chlorothioanisol (39.4 g, 247 mmol) in chloroform (180 mL) is added dropwise. The red colored reaction mixture is then slowly allowed to come to room temperature and stirred for another 4 h. The reaction mixture is slowly poured under stirring into ice water (700 mL) and the resulting yellow mixture is stirred for another 15 min. The aluminium salts are filtered off and the filtrate is extracted with dichloromethane (3×50 mL). The combined organic layers are washed with a saturated aqueous solution of sodium bicarbonate (50 mL) and dried over $MgSO_4$. The organic solvents are removed under vacuo and methyl 2-(3-chloro-4-(methylthio)phenyl)-2-oxoacetate can be obtained as an oil (36.4 g, 60%) (a).

A solution of this ester (61.7 g, 252 mmol) in toluene (120 mL) is heated to 50° C. Aqueous NaOH (3M, 105 mL, 313 mmol) is added dropwise in the manner that the temperature does not exceed 60° C. After complete addition, the mixture is stirred for another 1.5 h at 50° C. The source of heating is removed and HCl (10.6 mL, 290 mmol) is added dropwise to the warm reaction mixture. The mixture is stirred for another 16 h at room temperature. The formed precipitate is filtered off, washed with water (50 mL) and toluene (50 mL) and dried. The desired (2-(3-chloro-4-(methylthio)phenyl)-2-oxoacetic acid is obtained in this manner as a white solid (57.2 g, 98%) (b).

Hydrazine hydrate (8.5 mL, 273 mmol) is cooled to −50° C. The oxoacetic acid (12.6 g, 54.6 mmol) obtained from (b) is added in one portion resulting in a rise of the temperature. The resulting milky mixture is heated to 80° C. and after removal of the source of heating KOH (2.09 g, 31.7 mmol) is added in one portion which results in an exothermic reaction. The mixture is allowed to cool to 80° C. and then a second portion of KOH (2.09 g, 31.7 mmol) is added, followed by cooling to 80° C. This procedure is repeated twice. Once KOH has been added the fourth time, the reaction mixture is heated for 16 h at 100° C. The homogeneous reaction mixture is then cooled to room temperature, diluted with water (12 mL) and transferred to a separatory funnel. Water (12 mL) and diethyl ether (40 mL) are added and the layers are separated. The organic layer is extracted with water (2×15 mL). Heptane is added to the combined aqueous layers and the mixture is stirred vigorously. At a constant temperature below 50° C. using an ice bath, HCl (conc., 26 mL) is added within 30 min and the resulting suspension is stirred for 3 h at room temperature. The formed precipitate is filtered out and washed with aqueous HCl (2×6 mL), heptane (1×12 mL) and heptane/diethyl ether (15 mL, 4:1) and dried. 2-(3-chloro-4-(methylthio)phenyl)acetic acid (10.48 g, 89%) can be obtained as a creamy colored solid (c).

2-(3-chloro-4-(methylthio)phenyl)acetic acid is then alkylated in alpha-position analogous to Vazquez et al. (*Eur. J. Med. Chem. Chim. Ther.* (1997), 32, 6, 529-53). A solution of the acid (1.05 mmol) in dry THF (3 mL) is cooled to −78° C. under an argon atmosphere and stirred. Within 15 min, a solution of LDA in hexane (2 M, 1.6 mL, 3.2 mmol) and TMEDA (0.3 mL, 1.9 mmol) is added dropwise and the resulting mixture is slowly stirred for 3 h at −78° C. Methyl iodide (0.17 mL, 2.7 mmol) is added slowly under stirring and the mixture is stirred for another 16 h at room temperature. The reaction mixture is then neutralized applying a saturated aqueous solution of NH₄Cl (10 mL). The organic layer is separated and the aqueous alkaline one is acidified with HCl (5 N) and then extracted with diethyl ether (3×20 mL). The combined organic layers are dried over Na₂SO₄ and then concentrated in vacuo. Purification of the crude product by column chromatography (hexane/ethyl acetate 4:1) yields the desired 2-(3-chloro-4-(methylthio)phenyl)propanoic acid (d).

Synthesis of 2-(3-halogenated-4-(methylsulfonyl) phenyl)propanoic Acids (cf. Examples 29, 31)

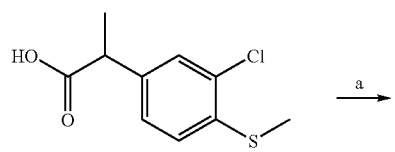

a

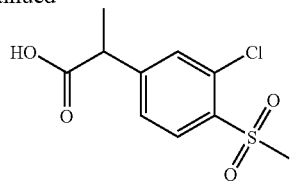

a. HCOOH, H₂O₂, 0-25° C., 15 h

In analogy to a described method in US2003/225283 the methylthiophenylpropanoic acids are transformed to the corresponding methylsulfonylphenylpropanoic acids. A solution of a methylthiophenyl propanoic acid (0.16 mmol) in formic acid (0.19 mL, 4.8 mmol) is cooled to 0° C. Aqueous H₂O₂ (30%, 0.10 mL, 0.8 mmol) is added at 0° C. and the mixture is stirred for 30 min. The reaction mixture is then quenched applying an aqueous solution of NaHSO₃ (10%), diluted with water (5 mL) and extracted with ethyl acetate (2×5 mL). The combined organic layers are dried over Mg₂SO₄ and the organic solvents are removed under vacuo. The residue is dissolved in methanol (1 mL). A solution of KMnO₄ (0.028 g, 0.176 mmol) in water (0.5 mL) is added dropwise and the resulting dark brown colored reaction mixture is stirred at room temperature for 30 min and then diluted with methanol (10 mL). The mixture is filtered and the filtrate is concentrated in vacuo and the crude product is purified by column chromatography (hexane/ethyl acetate 1:4). (a).

Synthesis of 2-(4-(N-substituted sulfamoyl)-3-fluorophenyl)propanoic Acids (cf. Example 32)

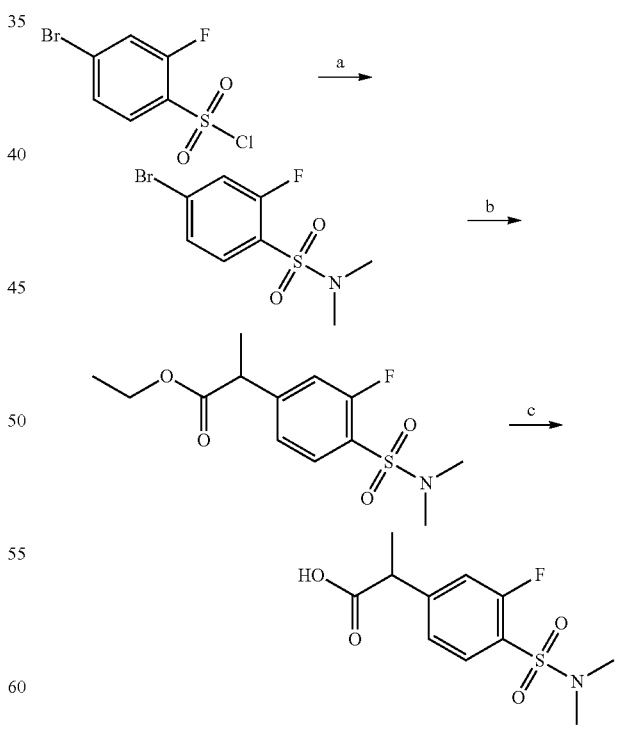

a. HN(CH₃)₂, pyridine, CH₂Cl₂, 2 h, rt;
b. Ethyl chloro propionate, NBu₄BF₄, NiBr₂bipy, DMF, rt;
c. LiOH, MeOH, 65° C., 4 h In analogy to Greig, I R et al. (*J. Med. Chem.* (2006), 49, 4787-7492) the corresponding bromo-fluorobenzene-sulfonyl chloride (5 mmol) and dimethylamine are dissolved in dichloromethane (15 mL). Pyridine (5 mmol) is added and the resulting mixture is stirred for 2 h at room temperature. After addition of water (15 mL), the organic layer is separated and extracted with ethyl acetate (15 mL). The combined organic layers are dried over Na$_2$SO$_4$ and then concentrated in vacuo. The crude product is purified by column chromatography (a).

In analogy to Durandetti, M. et al. (*Tetrahedron* (2007), 63, 1146-1153) the corresponding sulfamoyl-arylbromide is transformed into a sulfamoyl-arylpropanoic acid ester by applying ethyl chloropropionate.

A sulfamoyl-arylbromide (10 mmol) and ethyl 2-chloropropionate (1.6 mL, 13 mmol) are stirred in DMF (15 mL) under a nitrogen atmosphere at room temperature. Mn (1.1 g, 20 mmol), (2,2'-bipyridine)nickel(II)-dibromide (0.26 g, 0.7 mmol) and TFA (20 mL) are added and the reaction mixture is stirred for 1.5 h at 50° C. The reaction mixture is cooled and hydrolyzed by HCl (1 N, 25 mL). The resulting mixture is extracted with diethyl ether (3×25 mL) and the combined organic layers are washed with water (25 mL), saturated aqueous NaCl (25 mL), dried over MgSO$_4$ and reduced in vacuo. The precipitated solid is filtered off and washed with diethyl ether. The crude product is purified by column chromatography (b).

The propionate from (b) is dissolved in a mixture of THF (1.6 mL, 20 mmol) and water (0.8 mL, 45 mmol). LiOH (0.058 g, 2.43 mmol) is added and the reaction mixture is refluxed over night. Water (25 mL) and diethyl ether (25 mL) are added and the layers are separated. The aqueous one is acidified with HCl and extracted with dichloromethane (3×25 mL). The combined organic layers are dried over MgSO$_4$ and concentrated in vacuo to yield the N-substituted sulfamoyl-fluorophenyl propanoic acid (c).

Synthesis of 2-(4-methoxy and hydroxy-3,5-dimethylphenyl)propanoic Acids (cf. Examples 35-38)

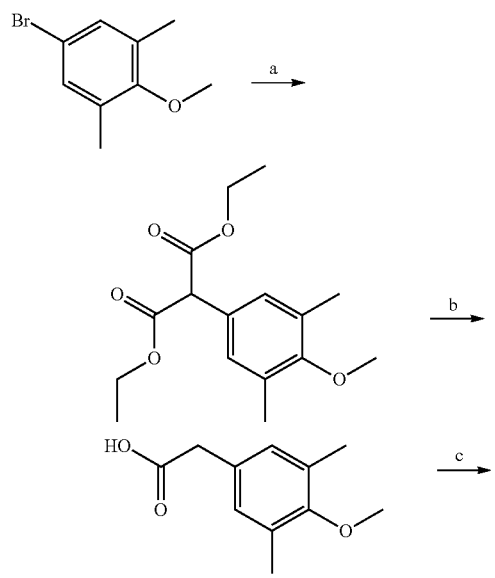

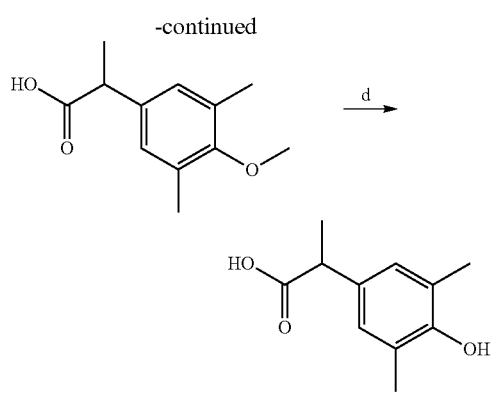

a. Diethyl malonate, NaH, CuBr, dioxane, 100° C., 16 h;
b. Naoh/THF:H$_2$O, reflux, 3 h;
c. CH$_3$I, hexane, LDA, TMEDA, -78° C., 3 h;
d. HBr, AcOH In analogy to a method described in WO2006/078834, phenylpropanoic acids can be obtained starting from aryl bromides and diethyl malonate.

In the first step NaH (60%, 1.45 g, 36.2 mmol) is added to a slowly stirred solution of an aryl bromide (16.5 mmol), CuBr (4.72 g, 32.9 mmol) and diethyl malonate (5 mL, 32.9 mmol) in 1,4-dioxane (20 mL) at room temperature. The reaction mixture is stirred for 16 h at 100° C. The mixture is filtered, the filtrate is concentrated in vacuo and the residue is purified by column chromatography (hexane/ethyl acetate 4:1) (a). Phenylmalonic acid diethylester (21 mmol) is dissolved in a mixture of aqueous NaOH (2N) and a mixture of THF and water (1:1) (20 mL). The resulting mixture is refluxed for 3 h, acidified with HCl (conc.) up to pH 1 and stirred for another hour. Aqueous NaOH (1N) is used to alkalize up to a pH of 13. The mixture is extracted with diethyl ether. The aqueous layer is acidified with HCl up to pH 5 and then extracted with ethyl acetate (3×). The combined organic layers are washed with a saturated aqueous solution of NaCl and dried over Na$_2$SO$_4$. The organic solvent was removed under reduced pressure (b).

Phenylacetic acid is then alkylated in alpha-position analogous to Vazquez et al. (*Eur. J. Med. Chem. Chim. Ther.* (1997), 32, 6, 529-53).

A solution of the acid (1.05 mmol) in dry THF (3 mL) is cooled to -78° C. under an argon atmosphere and stirred. Within 15 min, a solution of LDA in hexane (2 M, 1.6 mL, 3.2 mmol) and TMEDA (0.3 mL, 1.9 mmol) is added dropwise and the resulting mixture is slowly stirred for 3 h at -78° C. Methyl iodide (0.17 mL, 2.7 mmol) is added slowly under stirring and the mixture is stirred for another 16 h at room temperature. The reaction mixture is then neutralized utilizing a saturated aqueous solution of NH$_4$Cl (10 mL). The organic layer is separated and the aqueous alkaline one is acidified with HCl (5 N) and then extracted with diethyl ether (3×20 mL). The combined organic layers are dried over Na$_2$SO$_4$ and then concentrated in vacuo. Purification of the crude product by column chromatography (hexane/ethyl acetate 4:1) yields the desired substituted phenylmethoxypropanoic acid (c).

According to a procedure known to a person skilled in the art, the methoxyether group can be cleaved by HBr in acetic acid and the corresponding phenylhydroxy-propanoic acid can be obtained.

Synthesis of 2-(4-amino-3,5-difluorophenyl)propanoic Acid (cf. Example 26)

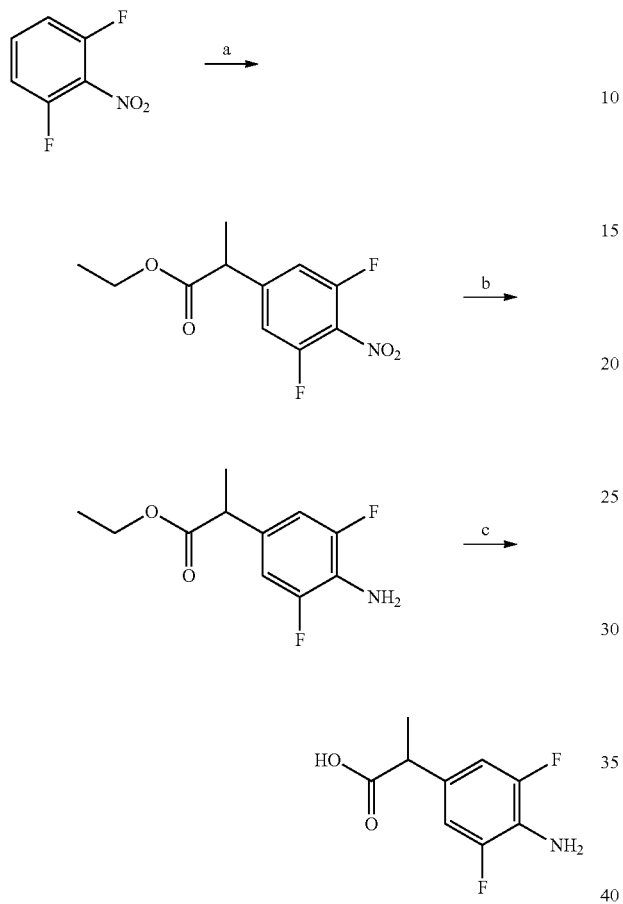

a. Ethyl chloropropionate, KOtBu, DMF, -40° C., 1 h;
b. H₂, Pd(C);
c. LiOH, THF/H₂O, reflux, 16 h KOtBu (3.57 g, 31.85 mmol) was dissolved in DMF (30 mL) and cooled to −45° C. To this solution a mixture of ethyl 2-chloropropionate (2 mL, 15.9 mmol) and 2,6-difluoronitrobenzene (2.5 g, 15.7 mmol) was added slowly dropwise at −40° C. The resulting solution was stirred for 1 h. The reaction mixture was then acidified with HCl (16%) up to pH 4 and diluted with water (150 mL) afterwards. The mixture was extracted with ethyl acetate (3×50 mL) and the combined organic layers were washed with water (50 mL) and a saturated aqueous solution of NaCl (2×50 mL) and dried over MgSO₄. The organic solvents were removed in vacuo and the product could be obtained as an oil (4.12 g, 99%) (a).

Difluoronitropropanoate (2.59 g, 10 mmol) was dissolved in EtOH/ethyl acetate (200 mL, 1:1) and then hydrogenated in an H-cube (1 bar, 25° C., 1 mL/min, 0.25 mol/L). The solvents were removed in vacuo and the difluoroaminopropanoate could be obtained as an oil (2.27 g, 99%) (b).

The crude product obtained from (b) (1 g, 4.36 mmol) was dissolved in a mixture of THF and water (10 mL, 2:1). LiOH (0.312 g, 13.1 mmol) was added and the reaction mixture was refluxed for 16 h. Water (50 mL) and diethyl ether (25 mL) were added and the layers were separated. The aqueous one was acidified with HCl (pH 2) and extracted with dichloromethane (3×50 mL). The combined organic layers were dried over MgSO₄ and concentrated in vacuo. The product was obtained as a white solid (0.72 g, 81%) (c).

7. General Instructions for the Reaction of Amines of the General Formulas V or X with Carboxylic Acids of the General Formula VII Method A:

The acid of the general formula VII (1 equivalent), the amine of the general formulas V or X (1.2 equivalents) and EDCI (1.2 equivalents) are stirred in DMF (10 mmol of acid in 20 mL) over a period of 12 hours at RT, and water is then added. The reaction mixture is extracted with EA a number of times, the aqueous phase is saturated with NaCl and then again extracted with EA. The combined organic phases are washed with 1N hydrochloric acid and sat. aq. NaCl soln., dried over MgSO₄, and the solvent is removed in vacuo. The residue is purified by means of flash chromatography (SiO₂, EA/hexane 1:2).

Method B:

The acid of the general formula VII (1 equivalent) and the amine of the general formula V or X (1.1 equivalents) are dissolved in DCM (1 mmol acid in 6 mL), and to the solution EDCI (1.5 equivalents), HOBt (1.4 equivalents) and Triethylamine (3 equivalents) are added at 0° C. The reaction mixture is stirred at RT for a period of 20 h and purified by column chromatography (2:1 mixture of n-hexane/AE).

The following example compounds were obtained in accordance with method B above.

Example Compound 3

2-(4-Amino-3-bromo-5-methoxyphenyl)-N-(4-methyl-6'-trifluoromethyl-3,4,5,6-tetrahydro-2H-[1,2']bipyridinyl-3'-ylmethyl)acetamide

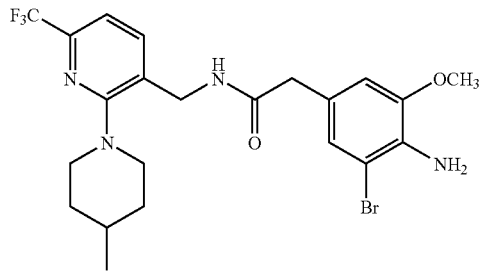 [SMILES: COc1cc(CC(=O)NCc2ccc(C(F)(F)F)nc2N2CCC(C)CC2)cc(Br)c1N]

¹H-NMR (CDCl₃) δ 7.52 (d, 1H, J=7.5 Hz), 7.21 (d, 1H, J=7.5 Hz), 6.93 (d, 1H, J=1.4 Hz), 6.57 (d, 1H), 6.24 (bt, NH), 4.47 (d, 2H), 4.22 (s, 2H), 3.80 (s, 3H), 3.51 (s, 2H), 3.30-3.26 (m, 2H), 1.70-1.48 (m, 3H), 1.21-1.09 (m, 2H), 0.95 (d, 3H, J=6.4 Hz)

IR 3298, 2924, 1649, 1575, 1500, 1460, 1420, 1338, 1135, 1047 cm⁻¹

Mass (FAB) m/z 515 and 517 [M+H]⁺ (Base), 537 and 539 [M+Na]⁺

Example Compound 4

2-(3-Fluorophenyl)-N-(4-methyl-6'-trifluoromethyl-3,4,5,6-tetrahydro-2H-[1,2']bipyridinyl-3'-ylmethyl)acetamide

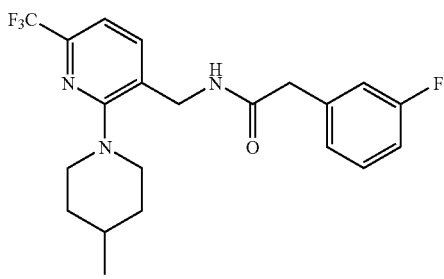 [SMILES: CC1CCN(c2nc(C(F)(F)F)ccc2CNC(=O)Cc2cccc(F)c2)CC1]

IR (KBr) 3272, 2923, 1648, 1592, 1552, 1455, 1421, 1374, 1337, 1246, 1138, 958, 835, 774 cm$^{-1}$
MS (FAB) m/z 410 (M+H)

Example Compound 5

2-(2,4-Difluorophenyl)-N-(4-methyl-6'-trifluoromethyl-3,4,5,6-tetrahydro-2H-[1,2']bipyridinyl-3'-ylmethyl)acetamide

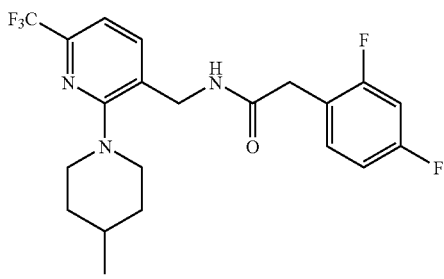 [SMILES: CC1CCN(c2nc(C(F)(F)F)ccc2CNC(=O)Cc2ccc(F)cc2F)CC1]

IR (KBr) 3270, 2921, 1647, 1558, 1507, 1424, 1330, 1242, 1134, 966, 851 cm$^{-1}$
MS (FAB) m/z 428 (M+H)

Example Compound 6

2-(2,6-Difluorophenyl)-N-(4-methyl-6'-trifluoromethyl-3,4,5,6-tetrahydro-2H-[1,2']bipyridinyl-3'-ylmethyl)acetamide

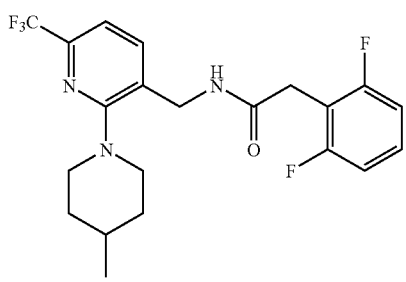 [SMILES: CC1CCN(c2nc(C(F)(F)F)ccc2CNC(=O)Cc2c(F)cccc2F)CC1]

IR (KBr) 3292, 2924, 1656, 1593, 1553, 1468, 1419, 1337, 1238, 1178, 1135, 1017, 945, 834, 784 cm$^{-1}$
MS (FAB) m/z 428 (M+H)

Example Compound 7

2-(2,5-Difluorophenyl)-N-(4-methyl-6'-trifluoromethyl-3,4,5,6-tetrahydro-2H-[1,2']bipyridinyl-3'-ylmethyl)acetamide

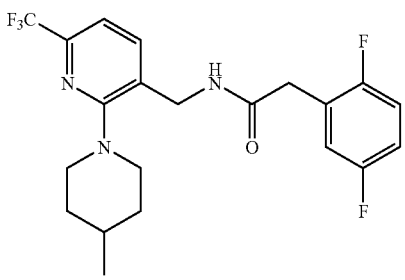 [SMILES: CC1CCN(c2nc(C(F)(F)F)ccc2CNC(=O)Cc2cc(F)ccc2F)CC1]

IR (KBr) 3271, 2922, 1644, 1593, 1555, 1497, 1424, 1329, 1137, 960, 833, 756 cm$^{-1}$
MS (FAB) m/z 428 (M+H)

Example Compound 8

2-(4-Fluorophenyl)-N-(4-methyl-6'-trifluoromethyl-3,4,5,6-tetrahydro-2H-[1,2']bipyridinyl-3'-ylmethyl)acetamide

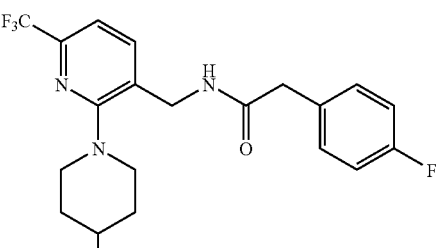

IR (KBr) 3255, 2920, 1646, 1595, 1558, 1509, 1424, 1330, 1229, 1132, 1043, 960, 828, 755 cm$^{-1}$
MS (FAB) m/z 410 (M+H)

Example Compound 9

2-(4-Hydroxy-3-methoxyphenyl)-N-(4-methyl-6'-trifluoromethyl-3,4,5,6-tetrahydro-2H-[1,2']bipyridinyl-3'-ylmethyl)propionamide

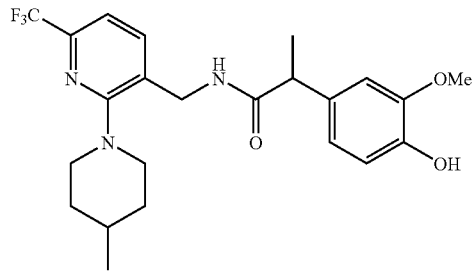 [SMILES: COc1cc(C(C)C(=O)NCc2ccc(C(F)(F)F)nc2N2CCC(C)CC2)ccc1O]

$^1$H NMR (300 M Hz, CDCl$_3$) δ7.44 (d, 1H, J=7.7 Hz), 7.17 (d, 1H, J=7.5 Hz), 6.88 (d, 1H, J=7.9 Hz), 6.80-6.70 (m, 2H), 6.11 (bt, 1H), 5.60 (s, 1H), 4.46-4.42 (m, 2H), 3.84 (s, 3H), 3.55 (q, 1H, J=7.1 Hz), 3.32-3.23 (m, 2H), 2.83-2.73 (m, 2H), 1.71-1.66 (m, 2H), 1.53 (d, 3H, J=7.1 Hz), 1.26-1.1 (m, 2H), 0.96 (d, 3H, J=6.6 Hz)

IR (KBr) 3301, 2925, 1650, 1516, 1458, 1421, 1373 cm$^{-1}$
MS (FAB) m/z 452 (M+H)

Example Compound 12

2-(4-Fluorophenyl)-N-(4-methyl-6'-trifluoromethyl-3,4,5,6-tetrahydro-2H-[1,2']bipyridinyl-3'-ylmethyl)propionamide

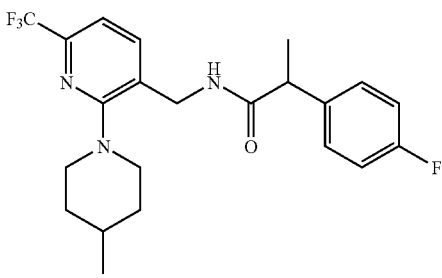

$^1$H-NMR (CDCl$_3$) δ 7.43 (d, 1H, J=7.5 Hz), 7.28-7.24 (m, 2H), 7.18 (d, 1H, J=7.7 Hz), 7.06-7.00 (m, 2H), 6.16 (bs, NH), 4.45 (d, 2H), 3.59 (q, 1H, J=7.0 Hz), 3.29 (m, 2H), 2.79 (m, 2H0, 1.75-1.50 (m, 3H), 1.53 (d, 3H, J=7.1 Hz), 1.26-1.10 (m, 2H), 0.96 (d, 3H, J=6.4 Hz)

IR 3291, 2925, 1650, 1510, 1458, 1419, 1336, 1231, 1177, 1138 cm$^{-1}$

Mass (FAB) m/z 424 [M+H]$^+$ (Base), 446 [M+Na]$^+$

Example Compound 10

2-(3,5-Difluorophenyl)-N-(4-methyl-6'-trifluoromethyl-3,4,5,6-tetrahydro-2H-[1,2']bipyridinyl-3'-ylmethyl)propionamide

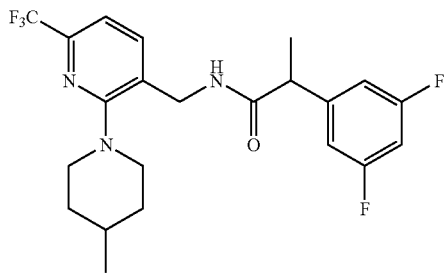 [SMILES: CC1CCN(c2nc(C(F)(F)F)ccc2CNC(=O)C(C)c2cc(F)cc(F)c2)CC1]

$^1$H NMR (300 M Hz, CDCl$_3$) δ 7.47 (d, 1H, J=7.5 Hz), 7.21 (d, 1H, J=7.7 Hz), 6.85-6.82 (m, 2H), 6.80-6.70 (m, 2H), 6.11 (bt, 1H), 5.60 (s, 1H), 4.46-4.42 (m, 2H), 3.84 (s, 3H), 3.55 (q, 1H, J=7.1 Hz), 3.32-3.23 (m, 2H), 2.83-2.73 (m, 2H), 1.71-1.66 (m, 2H), 1.53 (d, 3H, J=7.1 Hz), 1.26-1.1 (m, 2H), 0.96 (d, 3H, J=6.6 Hz)

IR (KBr) 3293, 2925, 1651, 1596, 1542, 1460, 1335 cm$^{-1}$
MS (FAB) m/z 442 (M+H)

Example Compound 13

2-(3-Fluorophenyl)N-(4-methyl-6'-trifluoromethyl-3,4,5,6-tetrahydro-2H-[1,2']bipyridinyl-3'-ylmethyl)propionamide

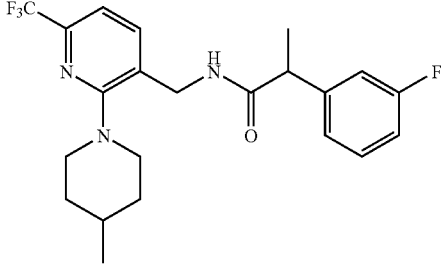 [SMILES: CC1CCN(c2nc(C(F)(F)F)ccc2CNC(=O)C(C)c2cccc(F)c2)CC1]

$^1$H-NMR (CDCl$_3$) δ 7.43 (d, 1H, J=7.7 Hz), 7.31 (m, 1H), 7.18 (d, 1H, J=7.7 Hz), 7.07-6.95 (m, 3H), 6.23 (bs, NH), 4.45 (d, 2H), 3.60 (q, 1H, J=7.0 Hz), 3.29 (m, 2H), 2.79 (m, 2H), 1.65-1.50 (m, 3H), 1.54 (d, 2H, J=7.0 Hz), 1.24-1.12 (m, 2H), 0.96 (d, 3H, J=6.4 Hz)

IR 3292, 2925, 1651, 1592, 1542, 1456, 1419, 1177, 1140 cm$^{-1}$

Mass (FAB) m/z 424 [M+H]$^+$ (Base), 446 [M+Na]$^+$

Example Compound 14

2-(3,4-Diaminophenyl)-N-(4-methyl-6'-trifluoromethyl-3,4,5,6-tetrahydro-2H-[1,2']bipyridinyl-3'-ylmethyl)propionamide

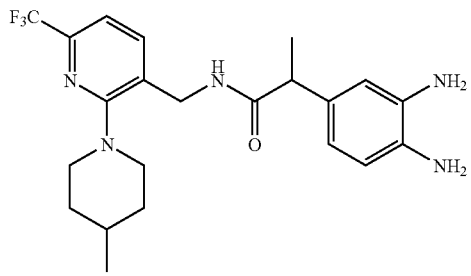 [SMILES: CC1CCN(c2nc(C(F)(F)F)ccc2CNC(=O)C(C)c2ccc(N)c(N)c2)CC1]

$^1$H-NMR (CDCl$_3$) δ7.42 (d, 1H, J=7.5 Hz), 7.17 (d, 1H, J=7.7 Hz), 6.67-6.57 (m, 3H), 6.03 (bt, NH), 4.41 (d, 2H), 3.49 (q, 1H, J=7.3 Hz), 3.40 (br, NH$_2$), 3.33-3.27 (m, 2H), 2.84-2.74 (m, 2H), 1.73-1.55 (m, 3H), 1.51 (d, 3H, J=7.1 Hz), 1.30-1.18 (m, 2H), 0.96 (d, 3H, J=6.6 Hz)

IR 3334, 2925, 1651, 1518, 1419, 1176, 1135, 733 cm$^{-1}$

Mass (FAB) m/z 436 [M+H]$^+$

Example Compound 15

N-(2-Butoxy-6-tert-butylpyridin-3-ylmethyl)-2-(3,4-diaminophenyl)propionamide

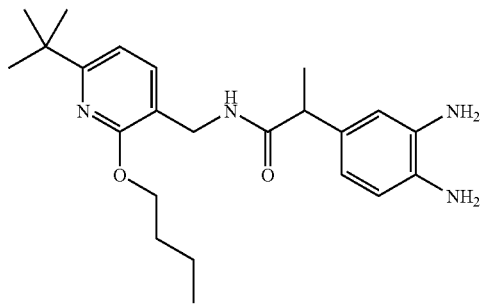 [SMILES: CCCCOc1nc(C(C)(C)C)ccc1CNC(=O)C(C)c1ccc(N)c(N)c1]

$^1$H-NMR (CDCl$_3$) δ 7.32 (d, 1H, J=7.5 Hz, Ar), 6.76 (d, 1H, J=7.3 Hz, Ar), 6.66-6.57 (m, 3H, Ar), 6.00 (bt, NH), 4.27 (m, 4H, OCH$_2$ & CH$_2$NH), 3.41 (q, 1H, J=7.1 Hz, CHCH$_3$), 1.64 (m, 2H, OCH$_2$CH$_2$), 1.45 (d, 3H, J=7.1 Hz, CHCH$_3$), 1.39 (m, 2H, CH$_2$CH$_3$), 1.29 (s, 9H, C(CH$_3$)$_3$), 0.95 (t, 3H, J=7.3 Hz, CH$_2$CH$_3$)

IR 3303, 2960, 1649, 1517, 1456, 1254 cm$^{-1}$

Mass (FAB) 399 m/z [M+H]$^+$

Example Compound 16

N-(6'-tert-Butyl-4-methyl-3,4,5,6-tetrahydro-2H-[1,2']bipyridinyl-3'-ylmethyl)-2-(3,4-diaminophenyl)propionamide

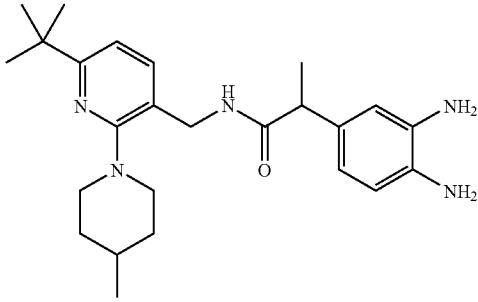 [SMILES: CC1CCN(c2nc(C(C)(C)C)ccc2CNC(=O)C(C)c2ccc(N)c(N)c2)CC1]

$^1$H-NMR (CDCl$_3$) δ 7.26 (d, 1H, J=7.9 Hz, Ar), 6.85 (d, 1H, J=7.7 Hz, Ar), 6.66-6.58 (m, 3H, Ar), 6.39 (bt, NH), 4.37 (m, 2H, CH$_2$NH), 3.45 (q, 1H, J=7.1 Hz, CHCH$_3$), 3.37 (bs, NH$_2$*2), 3.23 (m, 2H, piperidine), 2.74 (m, 2H, piperidine), 1.65-1.45 (m, 3H, piperidine), 1.49 (d, 3H, J=7.1 Hz, CHCH$_3$), 1.29 (s, 9H, C(CH$_3$)$_3$), 1.28-1.16 (m, 2H, piperidine), 0.95 (d, 3H, J=6.4 Hz, piperidine CH$_3$)

IR 3338, 2955, 1648, 1517, 1449, 1232 cm$^{-1}$

Mass (FAB) m/z 424[M+H]$^+$

Example Compound 17

N-(6-tert-Butyl-2-cyclohexylsulfanylpyridin-3-ylmethyl)-2-(3,4-diaminophenyl)-propionamide

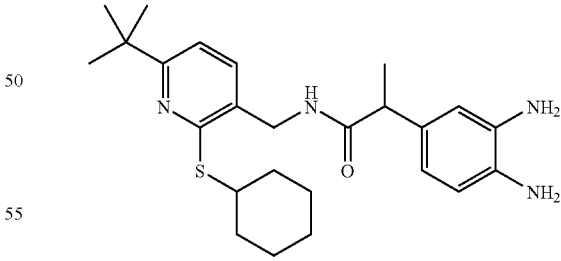

$^1$H-NMR (CDCl$_3$) δ 7.27 (d, 1H, Ar), 6.91 (d, 1H, J=7.9 Hz, Ar), 6.67-6.59 (m, 3H, Ar), 5.90 (bt, NH), 4.26 (m, 2H, CH$_2$NH), 3.96 (m, 1H, SCH), 3.46 (q, 1H, J=7.3 Hz, CHCH$_3$), 3.37 (bs, NH$_2$*2), 2.06 (m, 2H, cyclohexyl), 1.80-1.20 (m, 8H, cyclohexyl), 1.50 (d, 3H, CHCH$_3$), 1.31 (s, 9H, C(CH$_3$)$_3$)

IR 3303, 2929, 2854, 1651, 1517, 1444, 1079 cm$^{-1}$

Mass (FAB) m/z 441 [M+H]$^+$

Example Compound 19

2-(3,5-Dibromo-4-hydroxyphenyl)-N-(4-methyl-6'-trifluoromethyl-3,4,5,6-tetra-hydro-2H-[1,2']bipyridinyl-3'-ylmethyl)propionamide

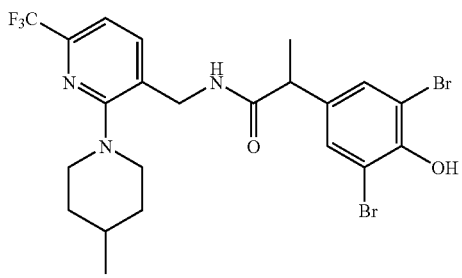 [SMILES: CC1CCN(c2nc(C(F)(F)F)ccc2CNC(=O)C(C)c2cc(Br)c(O)c(Br)c2)CC1]

$^1$H-NMR (CDCl$_3$) δ 7.48 (m, 1H, Ar), 7.39 (s, 2H, Ar), 7.22 (d, 1H, J=7.7 Hz, Ar), 6.27 (bt, NH), 4.47 (m, 2H, CH$_2$NH), 3.46 (q, 1H, J=7.1 Hz, CHCH$_3$), 3.31 (m, 2H, piperidine), 2.81 (m, 2H, piperidine), 2.40 (s, OH), 1.75-1.16 (m, 5H, piperidine), 1.50 (d, 3H, J=7.1 Hz, CHCH$_3$), 0.98 (d, 3H, J=6.4 Hz, piperidine CH$_3$)

IR 3298, 2924, 1650, 1550, 1462, 1417, 1176, 1138 cm$^{-1}$

Mass (FAB) m/z 580 [M+H]$^+$

Example Compound 21

2-(3-Bromo-4-hydroxy-5-methoxyphenyl)-N-(4-methyl-6'-trifluoromethyl-3,4,5,6-tetrahydro-2H-[1,2']bipyridinyl-3'-ylmethyl)acetamide

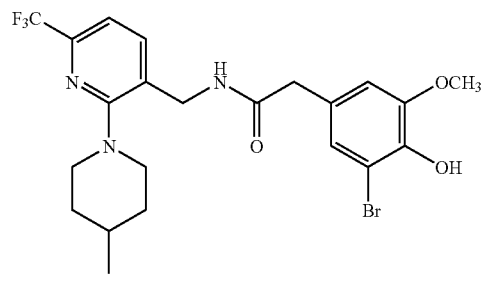

$^1$H-NMR (CDCl$_3$) δ 7.54 (d, 1H, J=7.5 Hz, Ar), 7.22 (d, 1H, J=7.7 Hz, Ar), 6.99 (d, 1H, J=1.5 Hz, Ar), 6.69 (d, 1H, J=2.0 Hz, Ar), 6.27 (bt, NH), 5.91 (bs, OH), 4.48 (m, 2H, CH$_2$NH), 3.86 (s, 3H, OCH$_3$), 3.53 (s, 2H, CH$_2$CO), 3.28 (m, 2H, piperidine), 2.80 (m, 2H, piperidine), 1.73-1.07 (m, 5H, piperidine), 0.96 (d, 3H, J=6.4 Hz, piperidine CH$_3$)

IR 3298, 2924, 1649, 1501, 1459, 1421, 1282, 1178, 1136, 1047 cm$^{-1}$

Mass (FAB) m/z 517[M+H]$^+$

Example Compound 20

2-(4-Amino-3,5-dibromophenyl)-N-(4-methyl-6'-trifluoromethyl-3,4,5,6-tetra-hydro-2H-[1,2']bipyridinyl-3'-ylmethyl)propionamide

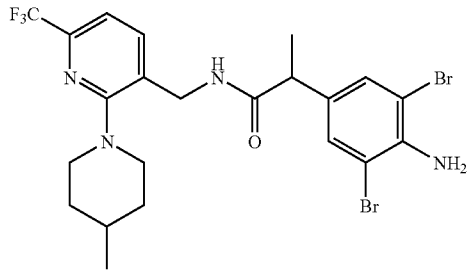 [SMILES: CC1CCN(c2nc(C(F)(F)F)ccc2CNC(=O)C(C)c2cc(Br)c(N)c(Br)c2)CC1]

$^1$H-NMR (CDCl$_3$) δ 7.47 (d, 1H, J=7.7 Hz, Ar), 7.31 (s, 2H, Ar), 7.21 (d, 1H, J=7.7 Hz, Ar), 6.18 (bt, NH), 4.55 (bs, NH$_2$), 4.46 (m, 2H, CH$_2$NH), 3.43 (q, 1H, J=7.0 Hz, CHCH$_3$), 3.30 (m, 2H, piperidine), 2.81 (m, 2H, piperidine), 1.75-1.15 (m, 5H, piperidine), 1.48 (d, 3H, J=7.1 Hz, CH$_2$CH$_3$), 0.97 (d, 3H, J=6.4 Hz, piperidine CH$_3$)

IR 3298, 2924, 1649, 1544, 1474, 1418, 1177, 1136 cm$^{-1}$

Mass (FAB) m/z 579[M+H]$^+$

Example Compound 22

2-(4-Amino-3,5-dibromophenyl)-N-(4-methyl-6'-trifluoromethyl-3,4,5,6-tetra-hydro-2H-[1,2']bipyridinyl-3'-ylmethyl)acetamide

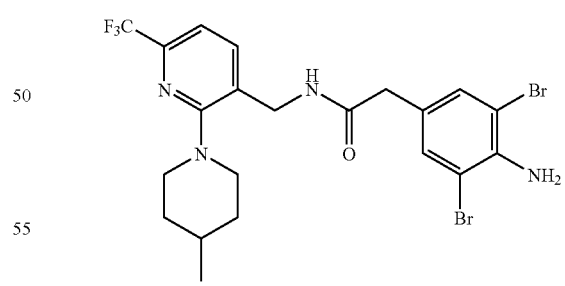

$^1$H-NMR (CDCl$_3$) δ 7.53 (d, 1H, J=7.3 Hz, Ar), 7.29 (s, 2H, Ar), 7.23 (d, 1H, J=7.7 Hz, Ar), 6.26 (bt, NH), 4.57 (bs, NH$_2$), 4.48 (m, 2H, CH$_2$NH), 3.46 (s, 2H, CH$_2$CO), 3.30 (m, 2H, piperidine), 2.81 (m, 2H, piperidine), 1.75-1.10 (m, 5H, piperidine), 0.97 (d, 3H, J=6.4 Hz, piperidine CH$_3$)

IR 3288, 2923, 1649, 1544, 1478, 1418, 1337, 1177, 1135 cm$^{-1}$

Mass (FAB) m/z 565 [M+H]$^+$

Example Compound 23

2-(3,5-Dibromo-4-hydroxyphenyl)-N-(4-methyl-6'-trifluoromethyl-3,4,5,6-tetra-hydro-2H-[1,2']bipyridinyl-3'-ylmethyl)acetamide

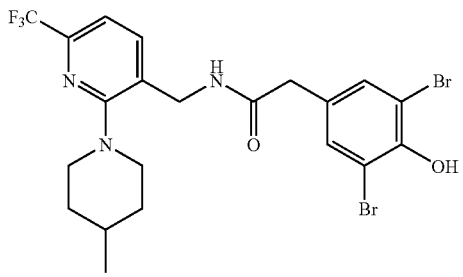 [SMILES: CC1CCN(c2nc(C(F)(F)F)ccc2CNC(=O)Cc2cc(Br)c(O)c(Br)c2)CC1]

$^1$H-NMR (CDCl$_3$) δ 7.55 (d, 1H, J=7.7 Hz, Ar), 7.38 (s, 2H, Ar), 7.24 (d, 1H, J=7.7 Hz, Ar), 6.31 (bt, NH), 4.50 (m, 2H, CH$_2$NH), 3.50 (s, 2H, CH$_2$CO), 3.31 (m, 2H, piperidine), 2.82 (m, 2H, piperidine), 2.40 (s, OH), 1.77-1.10 (m, 5H, piperidine), 0.97 (d, 3H, J=6.6 Hz, piperidine CH$_3$)

IR 3297, 2924, 1650, 1546, 1473, 1419, 1337, 1177, 1137 cm$^{-1}$

Mass (FAB) m/z 566 [M+H]$^+$

Example Compound 24

2-(3-Amino-4-hydroxyphenyl)-N-(4-methyl-6'-trifluoromethyl-3,4,5,6-tetrahydro-2H-[1,2']bipyridinyl-3'-ylmethyl)propionamide

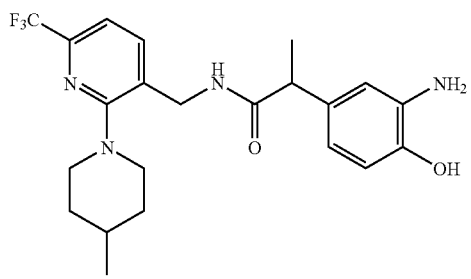 [SMILES: CC1CCN(c2nc(C(F)(F)F)ccc2CNC(=O)C(C)c2ccc(O)c(N)c2)CC1]

$^1$H-NMR (CDCl$_3$) δ 7.42 (d, 1H, J=7.7 Hz, Ar), 7.17 (d, 1H, J=7.7 Hz, Ar), 6.69-6.64 (m, 2H, Ar), 6.53 (dd, 1H, J=8.0, 1.8 Hz, Ar), 6.07 (bt, NH), 4.42 (d, 2H, J=5.7 Hz, CH$_2$NH), 3.69 (bs, NH$_2$), 3.59 (q, 1H, J=7.1 Hz, CHCH$_3$), 3.30 (m, 2H, piperidine), 2.79 (m, 2H, piperidine), 1.71-1.50 (m, 6H, piperidine & CHCH$_3$), 1.22 (m, 2H, piperidine), 0.96 (d, 3H, J=6.6 Hz, CHCH$_3$)

IR 3298, 2924, 1649, 1519, 1458, 1420, 1177, 1136 cm$^{-1}$

Mass (FAB) m/z 437 [M+H]$^+$, 459 [M+Na]$^+$

Example Compound 25

2-(3,5-Dibromophenyl)-N-(4-methyl-6'-trifluoromethyl-3,4,5,6-tetrahydro-2H-[1,2']bipyridinyl-3'-ylmethyl)acetamide

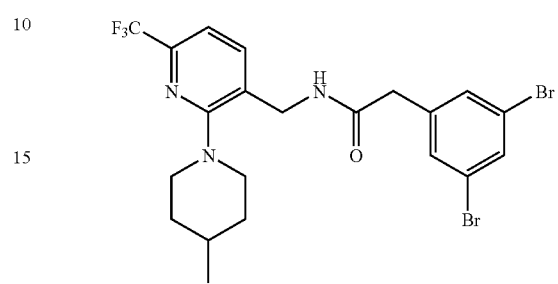

$^1$H-NMR (CDCl$_3$) δ 7.61 (t, 1H, J=1.7 Hz), 7.54 (d, 1H, J=7.7 Hz), 7.38 (d, 1H, J=1.7 Hz), 7.24 (d, 1H, J=7.7 Hz), 6.34 (bt, NH), 4.50 (d, 2H), 3.54 (s, 3H), 3.32 (m, 2H), 2.83 (m, 2H), 1.75-1.50 (m, 3H), 1.33-1.13 (m, 2H), 0.98 (d, 3H, J=6.4 Hz)

IR 3291, 2924, 1649, 1554, 1458, 1421, 1337, 1176, 1138 cm$^{-1}$

Mass (FAB) m/z 550[M+H]$^+$

The following example compounds were obtained according to the methods described above:

| | |
|---|---|
| [1] | 2-(4-Amino-3-fluorophenyl)-N-((2-(4-methylpiperidin-1-yl)-6-(trifluoromethyl)pyridin-3-yl)methyl)propanamide |
| [2] | 2-(3,5-Dibromophenyl)-N-((2-(4-methylpiperidin-1-yl)-6-(trifluoromethyl)pyridin-3-yl)methyl)acetamide |
| [11] | 2-(3,4-Difluorophenyl)-N-((2-(4-methylpiperidin-1-yl)-6-(trifluoromethyl)pyridin-3-yl)methyl)propanamide |
| [18] | 2-(4-Acetamido-3-fluorophenyl)-N-((2-(4-methylpiperidin-1-yl)-6-(trifluoromethyl)pyridin-3-yl)methyl)propanamide |
| [19] | 2-(3,5-Dibromo-4-hydroxyphenyl)-N-((2-(4-methylpiperidin-1-yl)-6-(trifluoromethyl)pyridin-3-yl)methyl)propanamide |
| [26] | 2-(4-Amino-3,5-difluorophenyl)-N-((2-(4-methylpiperidin-1-yl)-6-(trifluoromethyl)pyridin-3-yl)methyl)propanamide |
| [27] | 2-(3-Fluoro-5-hydroxy-4-nitrophenyl)-N-((2-(4-methylpiperidin-1-yl)-6-(trifluoromethyl)pyridin-3-yl)methyl)propanamide |
| [33] | N-(2-Fluoro-4-(1-((2-(4-methylpiperidin-1-yl)-6-(trifluormethyl)pyridin-3-yl)methylamino)-1-oxopropane-2-yl)phenyl)acrylamide |
| [34] | N-(2-Fluoro-6-iodo-4-(1-((2-(4-methylpiperidin-1-yl)-6-(trifluoromethyl)-pyridin-3-yl)methylamino)-1-oxopropane-2-yl)phenyl)acrylamide |

Example compounds 28-32 and 35-38 may also be obtained according to the methods described above.

Pharmacological Data

The affinity of the compounds of the invention for the vanilloid receptor 1 (VR1/TRPV1-Receptor) was detected as described above (Pharmacological Methods I and II respectively).

The compounds of the invention of the above formula I show excellent affinity to the VR1/TRPV1 receptor (Table 1).

TABLE 1

| Compound of Example | $K_i$ (Rat) Capsaicin [nM] | $K_i$ (Human) Capsaicin [nM] | $IC_{50}$ (Human) [nM] following pH-stimulus |
|---|---|---|---|
| 2 | 60.1 | 40.6 | ne |
| 3 | 16.7 | 4.4 | 253 |
| 4 | 80 | 34 | ne |
| 6 | 118 | 38 | ne |
| 7 | 63 | 30 | ne |
| 10 | | 24.7 | ne |
| 18 | | 25 | ne |
| 19 | | 1.1 | 31% @ 10 µM; 20% @ 5 µM; 0% @ 1 µM |
| 20 | | 0.9 | 27% @ 10 µM; 10% @ 5 µM; 0% @ 1 µM |
| 21 | | 0.1 | 38% @ 10 µM; 4% @ 5 µM |
| 22 | | 0.7 | 158 |
| 23 | | 0.3 | 35% @ 10 µM; 8% @ 5 µM |
| 26 | 3.4 | 9.6 | ne |
| 27 | 7.7 | 7.9 | 49% @ 10 µM; 35% @ 5 µM; 7% @ 1 µM |
| 34 | | 4.8 | ne |

Ne denotes "no effect", i.e. no reaction was observed.
The value following the symbol "@" indicates the concentration at which the inhibition (in percent) was determined.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A compound corresponding to formula I:

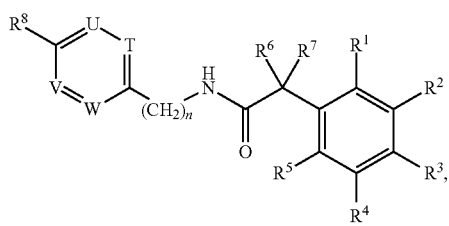

wherein
n is 0, 1, 2, 3, or 4;
$R^1$ represents H; F; Cl; Br; I; —CN; —NH$_2$; —OH; —SH; —C(=O)—NH$_2$; —S(=O)$_2$—NH$_2$; —C(=O)—NH—OH; —C(=O)—OH; —C(=O)—H; —S(=O)$_2$—OH; —C(=NH)—NH$_2$; —C(=NH)—NH—R$^9$; —O—P(=O)$_2$—O—R$^{12}$; —NHR$^{13}$; —NR$^{14}$R$^{15}$; —NH—C(=O)—R$^{13}$; —OR$^{16}$; —SR$^{17}$; —C(=O)—NHR$^{18}$; —C(=O)—NR$^{19}$R$^{20}$; —S(=O)$_2$—NHR$^{21}$; —S(=O)$_2$—NR$^{22}$R$^{23}$; —C(=O)—OR$^{24}$; —C(=O)—R$^{25}$; —S(=O)—R$^{26}$; —S(=O)$_2$—R$^{27}$ or a linear or branched, saturated or unsaturated, unsubstituted, monosubstituted or polysubstituted aliphatic $C_{1-10}$ group;
$R^2$ represents H; F; Cl; Br; I; —CN; —NH$_2$; —OH; —SH; —C(=O)—NH$_2$; —S(=O)$_2$—NH$_2$; —C(=O)—NH—OH; —C(=O)—OH; —C(=O)—H; —S(=O)$_2$—OH; —C(=NH)—NH$_2$; —C(=NH)—NH—R$^9$; —O—P(=O)$_2$—O—R$^{12}$; —NHR$^{13}$; —NR$^{14}$R$^{15}$; —NH—C(=O)—R$^{13}$; —OR$^{16}$; —SR$^{17}$; —C(=O)—NHR$^{18}$; —C(=O)—NR$^{19}$R$^{20}$; —S(=O)$_2$—NHR$^{21}$; —S(=O)$_2$—NR$^{22}$R$^{23}$; —C(=O)—OR$^{24}$; —C(=O)—R$^{25}$; —S(=O)—R$^{26}$; —S(=O)$_2$—R$^{27}$ or a linear or branched, saturated or unsaturated, unsubstituted, monosubstituted or polysubstituted aliphatic $C_{1-10}$ group;
$R^3$ represents H; F; Cl; Br; I; —CN; —NH$_2$; —OH; —SH; —C(=O)—NH$_2$; —C(=O)—NH—OH; —C(=O)—OH; —C(=O)—H; —S(=O)$_2$—OH; —C(=NH)—NH$_2$; —C(=NH)—NH—R$^9$; —O—P(=O)$_2$—O—R$^{12}$; —NHR$^{13}$; —NR$^{14}$R$^{15}$; —NH—C(=O)—R$^{13}$; —OR$^{16}$; —SR$^{17}$; —C(=O)—NHR$^{18}$; —C(=O)—NR$^{19}$R$^{20}$; —C(=O)—OR$^{24}$; —C(=O)—R$^{25}$; —S(=O)—R$^{26}$; —S(=O)$_2$—R$^{27}$ or a linear or branched, saturated or unsaturated, unsubstituted, monosubstituted or polysubstituted aliphatic $C_{1-10}$ group;
$R^4$ represents H; F; Cl; Br; I; —CN; —NH$_2$; —OH; —SH; —C(=O)—NH$_2$; —S(=O)$_2$—NH$_2$; —C(=O)—NH—OH; —C(=O)—OH; —C(=O)—H; —S(=O)$_2$—OH; —C(=NH)—NH$_2$; —C(=NH)—NH—R$^9$; —O—P(=O)$_2$—O—R$^{12}$; —NHR$^{13}$; —NR$^{14}$R$^{15}$; —NH—C(=O)—R$^{13}$; —OR$^{16}$; —SR$^{17}$; —C(=O)—NHR$^{18}$; —C(=O)—NR$^{19}$R$^{20}$; —S(=O)$_2$—NHR$^{21}$; —S(=O)$_2$—NR$^{22}$R$^{23}$; —C(=O)—OR$^{24}$; —C(=O)—R$^{25}$; —S(=O)—R$^{26}$; —S(=O)$_2$—R$^{27}$ or a linear or branched, saturated or unsaturated, unsubstituted, monosubstituted or polysubstituted aliphatic $C_{1-10}$ group;
$R^5$ represents H; F; Cl; Br; I; —CN; —NH$_2$; —OH; —SH; —C(=O)—NH$_2$; —S(=O)$_2$—NH$_2$; —C(=O)—NH—OH; —C(=O)—OH; —C(=O)—H; —S(=O)$_2$—OH; —C(=NH)—NH$_2$; —C(=NH)—NH—R$^9$; —O—P(=O)$_2$—O—R$^{12}$; —NHR$^{13}$; —NR$^{14}$R$^{15}$; —NH—C(=O)—R$^{13}$; —OR$^{16}$; —SR$^{17}$; —C(=O)—NHR$^{18}$; —C(=O)—NR$^{19}$R$^{20}$; —S(=O)$_2$—NHR$^{21}$; —S(=O)$_2$—NR$^{22}$R$^{23}$; —C(=O)—OR$^{24}$; —C(=O)—R$^{25}$; —S(=O)—R$^{26}$; —S(=O)$_2$—R$^{27}$ or a linear or branched, saturated or unsaturated, unsubstituted, monosubstituted or polysubstituted aliphatic $C_{1-10}$ group;
$R^6$ represents hydrogen or a linear or branched, saturated or unsaturated, unsubstituted, monosubstituted or polysubstituted aliphatic $C_{1-10}$ group;
$R^7$ represents hydrogen or —OH; or
$R^6$ and $R^7$ together with the carbon atom to which they are attached form a saturated or unsaturated, unsubstituted, monosubstituted or polysubstituted three-membered, four-membered, five-membered, or six-membered cycloaliphatic group;
$R^8$ represents —CF$_3$; or an unsubstituted tert-butyl group;
T stands for C—R$^{35}$; U stands for C—R$^{36}$; V stands for N, and W represents C—R$^{38}$; or
T stands for C—R$^{35}$; U stands for N, V stands for C—R$^{37}$, and W stands for C—R$^{38}$;
$R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$ and $R^{27}$, each independently represent a linear or branched, saturated or unsaturated, unsubstituted, monosubstituted or polysubstituted aliphatic $C_{1-10}$ group; or
an unsaturated or saturated, unsubstituted, monosubstituted or polysubstituted, three-membered, four-membered, five-membered, six-membered, seven-membered, eight-membered, or nine-membered cycloaliphatic group optionally containing at least one heteroatom as a ring member, wherein said cycloaliphatic group optionally may be condensed with a saturated or unsaturated, unsubstituted, monosubstituted or polysubstituted monocyclic or polycyclic ring system, or said cycloaliphatic group optionally may be bonded via a linear or branched, unsubstituted, monosubstituted or polysubstituted $C_{1-6}$ alkylene group or two to six-membered heteroalkylene group, or both; or an unsubstituted, monosubstituted or polysubstituted five-membered to fourteen-membered aryl group or heteroaryl group, which optionally may be condensed with a saturated or unsaturated, unsubstituted, monosubstituted or polysubstituted monocyclic or polycyclic ring system, or which optionally may be bonded via a linear or branched, unsubstituted, monosubstituted or polysubstituted $C_{1-6}$ alkylene group or two to six-membered heteroalkylene group, or both;

$R^{35}$, $R^{36}$, and $R^{37}$ each independently represent H; —$SF_5$; —$NO_2$; —$CF_3$; —CN; —$NH_2$; —OH; —SH; —C(=O)—$NH_2$; —S(=O)$_2$—$NH_2$; —C(=O)—NH—OH; —C(=O)—OH; —C(=O)—H; —S(=O)$_2$—OH; —$NHR^{13}$; —$NR^{14}R^{15}$; —NH—C(=O)—$R^{13}$; —$OR^{16}$; —$SR^{17}$; —C(=O)—$NHR^{18}$; —C(=O)—$NR^{19}R^{20}$; —S(=O)$_2$—$NHR^{21}$; —S(=O)$_2$—$NR^{22}R^{23}$; —C(=O)—$OR^{24}$; —C(=O)—$R^{25}$; —S(=O)—$R^{26}$; or —S(=O)$^2R^{27}$; or a linear or branched, saturated or unsaturated, unsubstituted, monosubstituted or polysubstituted aliphatic $C_{1-10}$ group; or an unsubstituted, monosubstituted or polysubstituted five-membered to fourteen-membered aryl group or heteroaryl group, which optionally may be condensed with a saturated or unsaturated, unsubstituted, monosubstituted or polysubstituted monocyclic or polycyclic ring system, or optionally may be bonded via a linear or branched, unsubstituted, monosubstituted or polysubstituted $C_{1-6}$ alkylene group or $C_{2-6}$ alkenylene group or $C_{2-6}$-alkynylene group, or both;

$R^{38}$ represents —$SF_5$; —$NO_2$; —$CF_3$; —$CF_2$Cl; —CN; —$NH_2$; —OH; —SH; —C(=O)—$NH_2$; —S(=O)$_2$—$NH_2$; —C(=O)—NH—OH; and —C(=O)—OH; —C(=O)—H; —S(=O)$_2$—OH; —$NHR^{39}$; —$NR^{40}R^{41}$; —$OR^{42}$; —$SR^{43}$; —C(=O)—$NHR^{44}$; —C(=O)—$NR^{45}R^{46}$; and —S(=O)$_2$—$NHR^{47}$; —S(=O)$_2$—$NR^{48}R^{49}$; —C(=O)—$OR^{50}$; —C(=P)—$R^{51}$; —S(=O)—$R^{52}$; —S(=O)$_2$—$R^{53}$; —C(=NH)—$NH_2$; —C(=NH)—NH—$R^{54}$; —N=C($NH_2$)$_2$; or —N=C($NHR^{55}$)—($NHR^{56}$); or a linear or branched, saturated or unsaturated, unsubstituted, monosubstituted or polysubstituted aliphatic $C_{1-10}$ group; or an unsaturated or saturated, unsubstituted, monosubstituted or polysubstituted three-membered, four-membered, five-membered, six-membered, seven-membered, eight-membered, or nine-membered cycloaliphatic group optionally containing at least one heteroatom as ring member, wherein said cycloaliphatic group is bonded to the parent structure via a carbon atom in the ring thereof, and optionally may be condensed with a saturated or unsaturated, unsubstituted, monosubstituted or polysubstituted monocyclic or polycyclic ring system, or optionally may be bonded via a linear or branched, unsubstituted, monosubstituted or polysubstituted $C_{1-6}$ alkylene group or $C_{2-6}$ alkenylene group or $C_{2-6}$ alkynylene group, or both; or an unsubstituted, monosubstituted or polysubstituted five-membered to fourteen-membered aryl or heteroaryl group, which optionally may be condensed with a saturated or unsaturated, unsubstituted, monosubstituted or polysubstituted monocyclic or polycyclic ring system, or optionally may be bonded via a linear or branched, unsubstituted, monosubstituted or polysubstituted $C_{1-6}$ alkylene group or $C_{2-6}$ alkenylene group or $C_{2-6}$-alkynylene group, or both;

$R^{39}$, $R^{40}$, $R^{41}$, $R^{42}$, $R^{43}$, $R^{44}$, $R^{45}$, $R^{46}$, $R^{47}$, $R^{48}$, $R^{49}$, $R^{50}$, $R^{51}$, $R^{52}$, $R^{53}$, $R^{54}$, $R^{55}$, and $R^{56}$ each independently represent a linear or branched, saturated or unsaturated, unsubstituted, monosubstituted or polysubstituted aliphatic $C_{1-10}$ group; or an unsaturated or saturated, unsubstituted, monosubstituted or polysubstituted, three-membered, four-membered, five-membered, six-membered, seven-membered, eight-membered, or nine-membered cycloaliphatic group optionally containing at least one heteroatom as ring member, wherein said cycloaliphatic group optionally may be condensed with a saturated or unsaturated, unsubstituted, monosubstituted or polysubstituted monocyclic or polycyclic ring system, or optionally may be bonded via a linear or branched, unsubstituted, monosubstituted or polysubstituted $C_{1-6}$ alkylene group or two to six-membered heteroalkylene group; or both; or an unsubstituted, monosubstituted or polysubstituted five-membered to fourteen-membered aryl or heteroaryl group, which optionally may be condensed with a saturated or unsaturated, unsubstituted, monosubstituted or polysubstituted monocyclic or polycyclic ring system, or optionally may be bonded via a linear or branched, unsubstituted, monosubstituted or polysubstituted $C_{1-6}$ alkylene group or two to six-membered heteroalkylene group; or both; or $R^{40}$ and $R^{41}$ together with nitrogen atom to which they are attached form a saturated or unsaturated four-membered, five-membered, six-membered, seven-membered, eight-membered, or nine-membered heterocycloaliphatic group, which is unsubstituted or substituted by 1, 2, 3, 4, or 5 groups $R^{57}$; which optionally contains at least one further heteroatom as ring member, and which optionally may be condensed with a saturated or unsaturated, unsubstituted, monosubstituted or polysubstituted monocyclic or polycyclic ring system;

$R^{57}$ represents —$NHR^{58}$, —$NR^{59}R^{60}$, or a linear or branched, saturated or unsaturated, unsubstituted, monosubstituted or polysubstituted aliphatic $C_{1-10}$ group;

$R^{58}$, $R^{59}$, and $R^{60}$ each independently represent —C(=O)—$R^{61}$; or a linear or branched, saturated or unsaturated, unsubstituted, monosubstituted or polysubstituted aliphatic $C_{1-10}$ group; or an unsubstituted, monosubstituted or polysubstituted five-membered to fourteen-membered aryl group or heteroaryl group, which optionally may be condensed with a saturated or unsaturated, unsubstituted, monosubstituted or polysubstituted monocyclic or polycyclic ring system, or optionally may be bonded via a linear or branched, unsubstituted, monosubstituted or polysubstituted $C_{1-6}$ alkylene group or $C_{2-6}$ alkenylene group or $C_{2-6}$ alkynylene group; or both; and $R^{61}$ represents a linear or branched, saturated or unsaturated, unsubstituted, monosubstituted or polysubstituted aliphatic $C_{1-10}$ group;

or a salt thereof;

wherein:
said aliphatic $C_{1-10}$ groups and tert-butyl groups each optionally may be substituted by 1, 2, 3, 4, 5, 6, 7, 8, or 9 substituents independently selected from the group consisting of F, Cl, Br, I, —CN, —NO$_2$, —OH, —NH$_2$, —SH, —O($C_{1-5}$ alkyl), —S($C_{1-5}$ alkyl), —NH($C_{1-5}$ alkyl), —N($C_{1-5}$ alkyl)-($C_{1-5}$ alkyl), —C(=O)—O—($C_{1-5}$ alkyl), —O—C(=O)—($C_{1-5}$ alkyl), —O-phenyl, phenyl, —OCF$_3$, and —SCF$_3$;

said two to six-membered heteroalkylene groups, $C_{1-6}$ alkylene groups, $C_{2-6}$ alkenylene groups, and $C_{2-6}$ alkynylene groups each optionally may be substituted by 1, 2, 3, 4, 5, 6, 7, 8, or 9 substituents independently selected from the group consisting of F, Cl, Br, I, —CN, —NO$_2$, —OH, —NH$_2$, —SH, —O($C_{1-5}$ alkyl), —S($C_{1-5}$ alkyl), —NH($C_{1-5}$ alkyl), —N($C_{1-5}$ alkyl)-($C_{1-5}$ alkyl), —OCF$_3$, and —SCF$_3$;

said heteroalkylene groups each optionally contain 1, 2, or 3 heteroatom(s) independently selected from the group consisting of oxygen, sulfur, and nitrogen (NH) as link(s);

said (hetero)cycloaliphatic groups each optionally may be substituted by 1, 2, 3, 4, or 5 substituents independently selected from the group consisting of —($C_{1-6}$ alkylene)—OH, =CH$_2$, —O—($C_{1-5}$ alkylene)oxetanyl, —($C_{1-5}$ alkylene)—O—($C_{1-5}$ alkylene)oxetanyl, —CH$_2$—NH—($C_{1-5}$ alkyl), —CH$_2$—N($C_{1-5}$ alkyl)$_2$, —N[C(=O)—($C_{1-5}$ alkyl)]phenyl, —CH$_2$—O—($C_{1-5}$ alkyl), oxo (=O), thioxo (=S), F, Cl, Br, I, —CN, —CF$_3$, —SF$_5$, —OH, —O—($C_{1-5}$ alkyl), —O—C(=O)—($C_{1-5}$ alkyl), —NH$_2$, —NO$_2$, —O—CF$_3$, —S—CF$_3$, —SH, —S—($C_{1-5}$ alkyl), —($C_{1-5}$ alkyl), —C(=O)—($C_{1-5}$ alkyl), —C(=O)—OH, —C(=O)—O—($C_{1-5}$ alkyl), —NH—($C_{1-5}$ alkyl), —N($C_{1-5}$ alkyl)$_2$, —NH-phenyl, —N($C_{1-5}$ alkyl)phenyl, cyclohexyl, cyclopentyl, (4,5)-dihydroisoxazolyl, thiazolyl, (1,2,5)-thiadiazolyl, thiophenyl, phenethyl, piperidinyl, pyrrolidinyl, —(CH$_2$)pyridinyl, pyridinyl, —O-phenyl, —O-benzyl, phenyl, and benzyl; wherein the cyclic moiety of the oxetanyl, (4,5)-dihydroisoxazolyl, thiazolyl, (1,2,5)-thiadiazolyl, thiophenyl, phenethyl, —N[C(=O)—($C_{1-5}$ alkyl)]phenyl, —NH-phenyl, —N($C_{1-5}$ alkyl)phenyl, —(CH$_2$)pyridinyl, pyridinyl, —O-phenyl, —O-benzyl, phenyl, and benzyl groups optionally may be substituted by 1, 2, 3, 4, or 5 substituents independently selected from the group consisting of F, Cl, Br, —OH, —CF$_3$, —SF$_5$, —CN, —NO$_2$, —($C_{1-5}$ alkyl), —O—($C_{1-5}$ alkyl), —O—CF$_3$, —S—CF$_3$, phenyl, and —O-benzyl; and wherein, unless otherwise stated, said (hetero)cycloaliphatic groups can each optionally exhibit 1, 2, or 3 (further) heteroatom(s) independently selected from the group consisting of oxygen, nitrogen, and sulfur;

the rings of said monocyclic or polycyclic ring systems each optionally may be substituted by 1, 2, 3, 4, or 5 substituents independently selected from the group consisting of oxo (=O), thioxo (=S), F, Cl, Br, I, —CN, —CF$_3$, —SF$_5$, —OH, —O—($C_{1-5}$ alkyl), —NH$_2$, —NO$_2$, —O—CF$_3$, —S—CF$_3$, —SH, —S—($C_{1-5}$ alkyl), —($C_{1-5}$ alkyl), —C(=O)—($C_{1-5}$ alkyl), —C(=O)—OH, —C(=O)—O—($C_{1-5}$ alkyl), —NH—($C_{1-5}$ alkyl), —N($C_{1-5}$ alkyl)$_2$, —O-phenyl, —O-benzyl, phenyl, and benzyl; wherein the cyclic moiety of the —O-phenyl, —O-benzyl, phenyl, and benzyl groups each optionally may be substituted by 1, 2, 3, 4, or 5 substituents independently selected from the group consisting of F, Cl, Br, —OH, —CF$_3$, —SF$_5$, —CN, —NO$_2$, —($C_{1-5}$ alkyl), —O—($C_{1-5}$ alkyl), —O—CF$_3$, —S—CF$_3$, phenyl, and —O-benzyl;

the rings of said monocyclic or polycyclic ring systems are each five-membered, six-membered, or seven-membered and each optionally may contain 1, 2, 3, 4, or 5 heteroatom(s) as ring member(s), wherein said heteroatoms are independently selected from the group consisting of oxygen, nitrogen, and sulfur;

said aryl or heteroaryl groups each optionally may be substituted by 1, 2, 3, 4, or 5 substituents independently selected from the group consisting of F, Cl, Br, I, —CN, —CF$_3$, —SF$_5$, —OH, —O—($C_{1-5}$ alkyl), —NH$_2$, —NO$_2$, —O—CF$_3$, —S—CF$_3$, —SH, —S—($C_{1-5}$ alkyl), —($C_{1-5}$ alkyl), —C(=O)—OH, —C(=O)—O—($C_{1-5}$ alkyl), —NH—($C_{1-5}$ alkyl), —N($C_{1-5}$ alkyl)$_2$, —NH—S(=O)$_2$—($C_{1-5}$ alkyl), —NH—C(=O)—O—($C_{1-5}$ alkyl), —C(=O)—H, —C(=O)—($C_{1-5}$ alkyl), —C(=O)—NH$_2$, —C(=O)—NH—($C_{1-5}$ alkyl), —C(=O)—N—($C_{1-5}$ alkyl)$_2$, —O-phenyl, —O-benzyl, phenyl, and benzyl; wherein the cyclic moiety of the —O-phenyl, —O-benzyl, phenyl, and benzyl groups each optionally may be substituted by 1, 2, 3, 4, or 5 substituents independently selected from the group consisting of F, Cl, Br, —OH, —CF$_3$, —SF$_5$, —CN, —NO$_2$, —($C_{1-5}$ alkyl), —O—($C_{1-5}$ alkyl), —O—CF$_3$, —S—CF$_3$, phenyl, and —O-benzyl; and said heteroaryl groups each optionally may contain 1, 2, 3, 4, or 5 heteroatom(s) independently selected from the group consisting of oxygen, nitrogen, and sulfur as ring member(s).

2. A compound according to claim 1, wherein said compound is in the form of an isolated stereoisomer.

3. A compound according to claim 1, wherein said compound is in the form of a mixute of stereoisomers in any mixing ratio.

4. A compound according to claim 1, wherein said compound is in the form of a racemic mixture.

5. A compound according to claim 1, wherein:

n is 0, 1, 2, 3, or 4;

$R^1$ represents H; F; Cl; Br; I; —CN; —NH$_2$; —OH; —SH; —C(=O)—NH$_2$; —S(=O)$_2$—NH$_2$; —C(=O)—NH—OH; —C(=O)—OH; —C(=O)—H; —S(=O)$_2$—OH; —NHR$^{13}$; —NR$^{14}$R$^{15}$; —NH—C(=O)—R$^{13}$; —OR$^{16}$; —SR$^{17}$; —S(=O)—NR$^{22}$R$^{23}$; —S(=O)—R$^{26}$; —S(=O)$_2$—R$^{27}$; methyl; —CF$_3$; —CCl$_3$; —CBr$_3$; —CHF$_2$; —CH$_2$F; —CF$_2$Cl; —CCl$_2$F; ethyl; —CF$_2$—CH$_3$; —CH$_2$—CF$_3$; —C$_2$F$_5$; —CH$_2$—CCl$_3$; —CH$_2$—CBr$_3$; —CHF—CF$_2$Cl; —CF$_2$—CF$_2$Cl; —CFCl—CF$_2$Cl; n-propyl; —CF$_2$—CF$_2$—CF$_3$; —CF(CF$_3$)$_2$; isopropyl; n-butyl; sec-butyl; isobutyl or tert-butyl;

$R^2$ represents H; F; Cl; Br; I; —CN; —NH$_2$; —OH; —SH; —C(=O)—NH$_2$; —S(=O)$_2$—NH$_2$; —C(=O)—NH—OH; —C(=O)—OH; —C(=O)—H; —S(=O)$_2$—OH; —NHR$^{13}$; —NR$^{14}$R$^{15}$; —NH—C(=O)—R$^{13}$; —OR$^{16}$; —SR$^{17}$; —S(=O)—NR$^{22}$R$^{23}$; —S(=O)—R$^{26}$; —S(=O)$_2$—R$^{27}$; methyl; —CF$_3$; —CCl$_3$; —CBr$_3$; —CHF$_2$; —CH$_2$F; —CF$_2$Cl; —CCl$_2$F; ethyl; —CF$_2$—CH$_3$; —CH$_2$—CF$_3$; —C$_2$F$_5$; —CH$_2$—CCl$_3$; —CH$_2$—CBr$_3$; —CHF—CF$_2$Cl; —CF$_2$—CF$_2$Cl; —CFCl—CF$_2$Cl; n-propyl; —CF$_2$—CF$_2$—CF$_3$; —CF(CF$_3$)$_2$; isopropyl; n-butyl; sec-butyl; isobutyl or tert-butyl;

$R^3$ represents H; F; Cl; Br; I; —CN; —NH$_2$; —OH; —SH; —C(=O)—NH$_2$; —C(=O)—NH—OH; —C(=O)—OH; —C(=O)—H; —S(=O)$_2$—OH; —NHR$^{13}$; —NR$^{14}$R$^{15}$; —NH—C(=O)—R$^{13}$; —OR$^{16}$; —SR$^{17}$; —S(=O)—R$^{26}$; —S(=O)$_2$—R$^{27}$; methyl; —CF$_3$; —CCl$_3$; —CBr$_3$; —CHF$_2$; —CH$_2$F; —CF$_2$Cl; —CCl$_2$F; ethyl; —CF$_2$—CH$_3$; —CH$_2$—CF$_3$; —C$_2$F$_5$; —CH$_2$—CCl$_3$; —CH$_2$—CBr$_3$; —CHF—CF$_2$Cl; —CF$_2$—CF$_2$Cl; —CFCl—CF$_2$Cl; n-propyl; —CF$_2$—CF$_2$—CF$_3$; —CF(CF$_3$)$_2$; isopropyl; n-butyl; sec-butyl; isobutyl or tert-butyl;

$R^4$ represents H; F; Cl; Br; I; —CN; —NH$_2$; —OH; —SH; —C(=O)—NH$_2$; —S(=O)$_2$—NH$_2$; —C(=O)—NH—OH; —C(=O)—OH; —C(=O)—H; —S(=O)$_2$—OH; —NHR$^{13}$; —NR$^{14}$R$^{15}$; —NH—C(=O)—R$^{13}$; —OR$^{16}$; —SR$^{17}$; —S(=O)—NR$^{22}$R$^{23}$; —S(=O)—R$^{26}$; —S(=O)$_2$—R$^{27}$; methyl; —CF$_3$; —CCl$_3$; —CBr$_3$; —CHF$_2$; —CH$_2$F; —CF$_2$Cl; —CCl$_2$F; ethyl; —CF$_2$—CH$_3$; —CH$_2$—CF$_3$; —C$_2$F$_5$; —CH$_2$—CCl$_3$; —CH$_2$—CBr$_3$; —CHF—CF$_2$Cl; —CF$_2$—CF$_2$Cl; —CFCl—CF$_2$Cl; n-propyl; —CF$_2$—CF$_2$—CF$_3$; —CF(CF$_3$)$_2$; isopropyl; n-butyl; sec-butyl; isobutyl or tert-butyl;

$R^5$ represents H; F; Cl; Br; I; —CN; —NH$_2$; —OH; —SH; —C(=O)—NH$_2$; —S(=O)$_2$—NH$_2$; —C(=O)—NH—OH; —C(=O)—OH; —C(=O)—H; —S(=O)$_2$—OH; —NHR$^{13}$; —NR$^{14}$R$^{15}$; —NH—C(=O)—R$^{13}$; —OR$^{16}$; —SR$^{17}$; —S(=O)—NR$^{22}$R$^{23}$; —S(=O)—R$^{26}$; —S(=O)$_2$—R$^{27}$; methyl; —CF$_3$; —CCl$_3$; —CBr$_3$; —CHF$_2$; —CH$_2$F; —CF$_2$Cl; —CCl$_2$F; ethyl; —CF$_2$—CH$_3$; —CH$_2$—CF$_3$; —C$_2$F$_5$; —CH$_2$—CCl$_3$; —CH$_2$—CBr$_3$; —CHF—CF$_2$Cl; —CF$_2$—CF$_2$Cl; —CFCl—CF$_2$Cl; n-propyl; —CF$_2$—CF$_2$—CF$_3$; —CF(CF$_3$)$_2$; isopropyl; n-butyl; sec-butyl; isobutyl or tert-butyl;

$R^6$ represents hydrogen or an alkyl group selected from the group consisting of —CH$_2$—OH, —CH$_2$—CH$_2$—OH, —CH$_2$—CH$_2$—CH$_2$—OH, —CH$_2$—CH$_2$—CH$_2$—CH$_2$—OH, isopropyl, n-butyl, sec-butyl, isobutyl, methyl, ethyl, and n-propyl;

$R^7$ represents hydrogen or —OH; or $R^6$ and $R^7$ together with carbon atom to which they are attached form a cycloalkyl group selected from the group consisting of cyclopropyl, cyclobutyl, cyclopentyl, cyclohexyl, and cycloheptyl;

$R^8$ represents —CF$_3$; or an unsubstituted tert-butyl group;

T represents C—R$^{35}$; U represents C—R$^{36}$; V represents N, and W represents C—R$^{38}$; or T represents C—R$^{35}$; U represents N, V represents C—R$^{37}$, and W represents C—R$^{38}$;

$R^{13}$, $R^{14}$, $R^{15}$, $R^{16}$, $R^{17}$, $R^{22}$, $R^{23}$, $R^{25}$, $R^{26}$, and $R^{27}$ each independently represent a group selected from the group consisting of methyl, —CF$_3$, —CCl$_3$, —CBr$_3$, —CHF$_2$, —CH$_2$F, —CF$_2$Cl, —CCl$_2$F, —CH$_2$—CN, —CH$_2$—O—CH$_3$, —CH$_2$—O—CF$_3$, —CH$_2$—SF$_3$, ethyl, —CF$_2$—CH$_3$, —CH$_2$—CF$_3$, —C$_2$F$_5$, —CH$_2$—CCl$_3$, —CH$_2$—CBr$_3$, —CHF—CF$_2$Cl, —CF$_2$—CF$_2$Cl, —CFCl—CF$_2$Cl, —CH$_2$—CH$_2$—CN, n-propyl, —CF$_2$—CF$_2$—CF$_3$, —CF(CF$_3$)$_2$, isopropyl, —CH$_2$—CH$_2$—CH$_2$—CN, —CH$_2$—O—CH$_2$—CH$_3$, —CH$_2$—CH$_2$—SF$_3$, —CH$_2$—CH$_2$—OCF$_3$, —CH(CH$_3$)—(O—CH$_3$), —CH(CH$_3$)—(S—CH$_3$), n-butyl, —CF$_2$—CF$_2$—CF$_2$—CF$_3$, —CH$_2$—CH$_2$—CH$_2$—CH$_2$—CN, sec-butyl, isobutyl, tert-butyl, n-pentyl, 3-pentyl, n-heptyl, 4-heptyl, n-octyl, n-nonyl, 5-nonyl, (2,6)-dimethyl-hept-4-yl, 3-methylbutyl, n-hexyl, (3,3)-dimethylbutyl, —CH$_2$—CH$_2$—O—CH$_3$, —CH$_2$—CH$_2$—O—C$_2$H$_5$, —CH$_2$—CH$_2$—CH$_2$—O—CH$_3$, ethenyl, propenyl, 2-butenyl, 3-butenyl, 2-pentenyl, and 3-pentenyl; or a group selected from the group consisting of 2,3-dihydro-1H-indenyl, cyclopropyl, oxetanyl, cyclobutyl, cyclopentyl, cyclohexyl, imidazolidinyl, tetrahydrofuranyl, tetrahydrothiophenyl, pyrrolidinyl, piperidinyl, morpholinyl, piperazinyl, azepanyl, diazepanyl, azocanyl, and thiomorpholinyl, each of which optionally may be bonded via a —CH$_2$—O—, —CH$_2$—CH$_2$—O—, —CH$_2$—CH$_2$—O—CH$_2$—, —CH$_2$—CH(CH$_3$)—O—CH$_2$—, —(CH$_2$)—, —(CH$_2$)$_2$ bond or —(CH$_2$)$_3$ group, and each of which may be unsubstituted or optionally substituted by 1, 2, 3, 4, or 5 substituents independently selected from the group consisting of oxo (=O), thioxo (=S), —OH, —O—CH$_3$, —O—C$_2$H$_5$, —O—CH(CH$_3$)$_2$, —O—C(CH$_3$)$_3$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl, tert-butyl, n-pentyl, —C(=O)—CH$_3$, —C(=O)—C$_2$H$_5$, —C(=O)—CH(CH$_3$)$_2$, —C(=O)—C(CH$_3$)$_3$, —C(=O)—OH, —C(=O)—O—CH$_3$, —C(=O)—O—C$_2$H$_5$, —C(=O)—O—CH(CH$_3$)$_2$, and —C(=O)—O—C(CH$_3$)$_3$; or a group selected from the group consisting of phenyl, naphthyl, thiophenyl, furanyl, pyrrolyl, pyrazolyl, pyrazinyl, pyranyl, triazolyl, pyridinyl, imidazolyl, thiazolyl, oxazolyl, and isoxazolyl; each of which optionally may be bonded via a —(CH$_2$)—, —(CH$_2$)$_2$ bond or —(CH$_2$)$_3$ group, and each of which may be unsubstituted or optionally substituted by 1, 2, 3, 4, or 5 substituents independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —NH$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl, tert-butyl, n-pentyl, —C(=O)—OH, —C(=O)—O—CH$_3$, —C(=O)—O—C$_2$H$_5$, —C(=O)—O—CH(CH$_3$)$_2$, —C(=O)—O—C(CH$_3$)$_3$, —NH—CH$_3$, —NH—C$_2$H$_5$, —NH—C(CH$_3$)$_3$, —N(CH$_3$)$_2$, —N(C$_2$H$_5$)$_2$, —N(CH$_3$)—(C$_2$H$_5$), —NH—C(=O)—O—CH$_3$, —NH—C(=O)—O—C$_2$H$_5$, —NH—C(=O)—O—C(CH$_3$)$_3$, —C(=O)—H, —C(=O)—CH$_3$, —C(=O)—C$_2$H$_5$, —C(=O)—CH(CH$_3$)$_2$, —C(=O)—C(CH$_3$)$_3$, —C(=O)—NH$_2$, —C(=O)—NH—CH$_3$, —C(=O)-nH-C$_2$H$_5$, —C(=O)—N(CH$_3$)$_2$, —C(=O)—N(C$_2$H$_5$)$_2$, —O-phenyl, —O-benzyl, phenyl, and benzyl;

$R^{35}$, $R^{36}$, and $R^{37}$ each independently represent H; —SF$_5$; —NO$_2$; —CN; —NH$_2$; —OH; —SH; —C(=O)—NH$_2$; —S(=O)$_2$—NH$_2$; —C(=O)—NH—OH; and —C(=O)—OH; —C(=O)—H; —S(=O)$_2$—OH; —NHR$^{13}$; —NR$^{14}$R$^{15}$; OR$^{16}$; —SR$^{17}$; —S(=O)—R$^{25}$; —S(=O)$_2$—R$^{26}$; —CH$_2$—OH; methyl; —CF$_3$; —CCl$_3$; —CBr$_3$; —CHF$_2$; —CH$_2$F; —CF$_2$Cl; —CCl$_2$F; ethyl; —CF$_2$—CH$_3$; —CH$_2$—CF$_3$; —C$_2$F$_5$; —CH$_2$—CCl$_3$; —CH$_2$—CBr$_3$; —CHF—CF$_2$Cl; —CF$_2$—CF$_2$Cl; —CFCl—CF$_2$Cl; n-propyl; —CF$_2$—CF$_2$—CF$_3$; —CF(CF$_3$)$_2$; isopropyl; n-butyl; sec-butyl; isobutyl, or tert-butyl; or a phenyl group which may be unsubstituted or optionally substituted by 1, 2, 3, 4, or 5 substituents independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —NH$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl, tert-butyl, and n-pentyl;

R$^{38}$ represents —SF$_5$; —NO$_2$; —CN; —NH$_2$; —OH; —SH; —C(=O)—NH$_2$; —S(=O)$_2$—NH$_2$; —C(=O)—NH—OH; —C(=O)—OH; —C(=O)—H; —S(=O)$_2$—OH; —NHR$^{39}$; —NR$^{40}$R$^{41}$; —OR$^{42}$; —SR$^{43}$; —C(=O)—OR$^{50}$; and —S(=O)—R$^{52}$; —S(=O)$_2$—R$^{53}$; —C(=NH)—NH$_2$; —C(=NH)—NH—R$^{54}$; —N=C(NH$_2$)$_2$; or —N=C(NHR$^{55}$)—(NHR$^{56}$); or a cyclic group selected from the group consisting of cyclopropyl, cyclobutyl, cyclopentyl, cyclohexyl, cyclohexenyl, imidazolidinyl, tetrahydrofuranyl, tetrahydrothiophenyl, pyrrolidinyl, piperidinyl, morpholinyl, piperazinyl, azepanyl, diazepanyl, azocanyl, and thiomorpholinyl, each of which is bonded to the basic framework via a carbon atom of the rings thereof, optionally via a —(CH=CH)—, —C≡C or —C≡C—CH$_2$— group, and each of which may be unsubstituted or optionally substituted by 1, 2, 3, 4, or 5 substituents independently selected from the group consisting of —CN, —CH$_2$—N(CH$_3$)$_2$, —CH$_2$—N(C$_2$H$_5$)$_2$, —CH$_2$—NH—CH$_3$, —CH$_2$—NH—C$_2$H$_5$, —N—[C(=O)—C$_2$H$_5$]phenyl, —N—[C(=O)—CH$_3$]phenyl, oxo (=O), thioxo (=S), —OH, —O—CH$_3$, —O—C$_2$H$_5$, —O—CH(CH$_3$)$_2$, —O—C(CH$_3$)$_3$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl, tert-butyl, n-pentyl, —C(=O)—CH$_3$, —C(=O)—C$_2$H$_5$, —C(=O)—CH(CH$_3$)$_2$, —C(=O)—C(CH$_3$)$_3$, —C(=O)—OH, —C(=O)—O—CH$_3$, —C(=O)—O—C$_2$H$_5$, —C(=O)—O—CH(CH$_3$)$_2$, and —C(=O)—O—C(CH$_3$)$_3$; or a group selected from the group consisting of (1,3)-benzodioxolyl, (1,4)-benzodioxanyl, tetrazolyl, (2,3)-dihydrothieno[3.4-b][1.4]dioxinyl, benzo[b]furanyl, phenyl, naphthyl, thiophenyl, furanyl, pyrrolyl, pyrazolyl, pyrazinyl, pyranyl, triazolyl, pyridinyl, imidazolyl, indolyl, isoindolyl, thiazolyl, oxazolyl, isoxazolyl, pyridazinyl, pyrazinyl, pyrimidinyl, indazolyl, quinoxalinyl, quinolinyl, and isoquinolinyl, each of which optionally may be bonded via a —(CH=CH)—, —C≡C—, —(CH$_2$)—, —(CH$_2$)$_2$— or —(CH$_2$)$_3$— group, and each of which may be unsubstituted or optionally substituted by 1, 2, 3, 4, or 5 substituents independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —NH$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl, tert-butyl, n-pentyl, —C(=O)—OH, —C(=O)—O—CH$_3$, —C(=O)—O—C$_2$H$_5$, —C(=O)—O—CH(CH$_3$)$_2$, —C(=O)—O—C(CH$_3$)$_3$, —NH—CH$_3$, —NH—C$_2$H$_5$, —NH—C(CH$_3$)$_3$, —N(CH$_3$)$_2$, —N(C$_2$H$_5$)$_2$, —N(CH$_3$)—(C$_2$H$_5$), —NH—C(=O)—O—CH$_3$, —NH—S(=O)$_2$—CH$_3$, —NH—S(=O$_2$)—C$_2$H$_5$, —NH—S(=O)$_2$—CH(CH$_3$)$_2$, —NH—C(=O)—O—C$_2$H$_5$, —NH—C(=O)—O—C(CH$_3$)$_3$, —C(=O)—H, —C(=O)—CH$_3$, —C(=O)—C$_2$H$_5$, —C(=O)—CH(CH$_3$)$_2$, —C(=O)—C(CH$_3$)$_3$, —C(=O)—NH$_2$, —C(=O)—NH—CH$_3$, —C(=O)-nH—C$_2$H$_5$, —C(=O)—N(CH$_3$)$_2$, —C(=O)—N(C$_2$H$_5$)$_2$, —O-phenyl, —O-benzyl, phenyl, and benzyl;

R$^{39}$, R$^{40}$, and R$^{41}$, R$^{42}$, R$^{43}$, R$^{50}$, R$^{52}$, R$^{53}$, R$^{54}$, R$^{55}$, and R$^{56}$ each independently represent a group selected from the group consisting of methyl, —CF$_3$, —CCl$_3$, —CBr$_3$, —CHF$_2$, —CH$_2$F, —CF$_2$Cl, —CCl$_2$F, —CH$_2$—CN, —CH$_2$—O—CH$_3$, —CH$_2$—O—CF$_3$, —CH$_2$—SF$_3$, ethyl, —CF$_2$—CH$_3$, —CH$_2$—CF$_3$, —C$_2$F$_5$, —CH$_2$—CCl$_3$, —CH$_2$—CBr$_3$, —CHF—CF$_2$Cl, —CF$_2$—CF$_2$Cl, —CFCl—CF$_2$Cl, —CH$_2$—CH$_2$—CN, n-propyl, —CF$_2$—CF$_2$—CF$_3$, —CF(CF$_3$)$_2$, isopropyl, —CH$_2$—CH$_2$—CH$_2$—CN, —CH$_2$—O—CH$_2$—CH$_3$, —CH$_2$—CH$_2$—SF$_3$, —CH$_2$—CH$_2$—OCF$_3$, —CH(CH$_3$)—(O—CH$_3$), —CH(CH$_3$)—(S—CH$_3$), n-butyl, —CF$_2$—CF$_2$—CF$_2$—CF$_3$, —CH$_2$—CH$_2$—CH$_2$—CH$_2$—CN, sec-butyl, isobutyl, tert-butyl, n-pentyl, 3-pentyl, n-heptyl, 4-heptyl, n-octyl, n-nonyl, 5-nonyl, (2,6)-dimethyl-hept-4-yl, 3-methylbutyl, n-hexyl, (3,3)-dimethylbutyl, —CH$_2$—CH$_2$—O—CH$_3$, —CH$_2$—CH$_2$—O—C$_2$H$_5$, —CH$_2$—CH$_2$—CH$_2$—O—CH$_3$, ethenyl, propenyl, 2-butenyl, 3-butenyl, 2-pentenyl, and 3-pentenyl; or a group selected from the group consisting of 2,3-dihydro-1H-indenyl, cyclopropyl, oxetanyl, cyclobutyl, cyclopentyl, cyclohexyl, imidazolidinyl, tetrahydrofuranyl, tetrahydrothiophenyl, pyrrolidinyl, piperidinyl, morpholinyl, piperazinyl, azepanyl, diazepanyl, azocanyl, and thiomorpholinyl, each of which optionally may be bonded via a —CH$_2$—O—, —CH$_2$—CH$_2$—O—, —CH$_2$—CH$_2$—O—CH$_2$—, —CH$_2$—CH(CH$_3$)—O—CH$_2$—, —(CH$_2$)—, —(CH$_2$)$_2$bond or —(CH$_2$)$_3$ group, and each of which may be unsubstituted or optionally substituted by 1, 2, 3, 4, or 5 substituents independently selected from the group consisting of oxo (=O), thioxo (=S), —OH, —O—CH$_3$, —O—C$_2$H$_5$, —O—CH(CH$_3$)$_2$, —O—C(CH$_3$)$_3$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl, tert-butyl, n-pentyl, —C(=O)—CH$_3$, —C(=O)—C$_2$H$_5$, —C(=O)—CH(CH$_3$)$_2$, —C(=O)—C(CH$_3$)$_3$, —C(=O)—OH, —C(=O)—O—CH$_3$, —C(=O)—O—C$_2$H$_5$, —C(=O)—O—CH(CH$_3$)$_2$, and —C(=O)—O—C(CH$_3$)$_3$; or a group selected from the group consisting of phenyl, naphthyl, thiophenyl, furanyl, pyrrolyl, pyrazolyl, pyrazinyl, pyranyl, triazolyl, pyridinyl, imidazolyl, thiazolyl, oxazolyl, and isoxazolyl, each of which optionally may be bonded via a —(CH$_2$)—, —(CH$_2$)$_2$— or —(CH$_2$)$_3$-group, and each of which may be unsubstituted or optionally substituted by 1, 2, 3, 4, or 5 substituents independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —NH$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl, tert-butyl, n-pentyl, —C(=O)—OH, —C(=O)—O—CH$_3$, —C(=O)—O—C$_2$H$_5$, —C(=O)—O—CH(CH$_3$)$_2$, —C(=O)—O—C(CH$_3$)$_3$, —NH—CH$_3$, —NH—C$_2$H$_5$, —NH—C(CH$_3$)$_3$, —N(CH$_3$)$_2$, —N(C$_2$H$_5$)$_2$, —N(CH$_3$)—(C$_2$H$_5$), —NH—C(=O)—O—CH$_3$, —NH—C(=O)—O—C$_2$H$_5$, —NH—C(=O)—O—C(CH$_3$)$_3$, —C(=O)—H, —C(=O)—CH$_3$, —C(=O)—C$_2$H$_5$, —C(=O)—CH(CH$_3$)$_2$, —C(=O)—C(CH$_3$)$_3$, —C(=O)—NH$_2$, —C(=O)—NH—CH$_3$, —C(=O)-nH—C$_2$H$_5$, —C(=O)—N(CH$_3$)$_2$, —C(=O)—N(C$_2$H$_5$)$_2$, —O-phenyl, —O-benzyl, phenyl, and benzyl; or $R^{40}$ and $R^{41}$ together with the nitrogen atom to which they are attached form a group selected from the group consisting of 3-azabicyclo[3.1.1]heptyl, 6-azaspiro[2.5]octyl, 3-acabicyclo[3.2.1]octyl, 6-azabicyclo[3.3.1]heptyl, 8-acabicyclo[3.2.1]octyl, 1-oxa-2,8-diazaspiro[4.5]dec-2-enyl, azocanyl, isoindolyl, indolyl, (1,2,3,6)-tetrahydropyridinyl, (4,5,6,7)-tetrahydroisoxazolo[5.4-c]pyridinyl, pyrrolidinyl, piperidinyl, piperazinyl, morpholinyl, azepanyl, diazepanyl, and thiomorpholinyl, wherein the heterocycloaliphatic portion may be unsubstituted or optionally substituted by 1, 2, 3, 4, or 5 groups $R^{57}$;

$R^{57}$ represents —NHR$^{58}$, —NR$^{59}$R$^{60}$, or an alkyl group selected from the group consisting of —CF$_3$, —CH$_2$—CF$_3$, methyl, ethyl, n-propyl, isopropyl, tert-butyl, n-butyl, sec-butyl, and isobutyl;

$R^{58}$, $R^{59}$, and $R^{60}$ each independently represent —C(=O)—R$^{61}$; or an alkyl group selected from the group consisting of —CF$_3$, —CH$_2$—CF$_3$, methyl, ethyl, n-propyl, isopropyl, tert-butyl, n-butyl, sec-butyl, and isobutyl; or a group selected from the group consisting of phenyl, naphthyl, thiophenyl, furanyl, pyrrolyl, pyrazolyl, pyrazinyl, pyranyl, triazolyl, pyridinyl, imidazolyl, thiazolyl, oxazolyl, and isoxazolyl, each of which optionally may be bonded via a —(CH$_2$)—, —CH$_2$)$_2$— or —(CH$_2$)$_3$— group, and each of which may be unsubstituted or optionally substituted by 1, 2, 3, 4, or 5 substituents independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —NH$_2$, —NO$_2$, —O—CF$_3$, —S—CF$_3$, —SH, —S—CH$_3$, —S—C$_2$H$_5$, —S—CH(CH$_3$)$_2$, —S—C(CH$_3$)$_3$, methyl, ethyl, n-propyl, isopropyl, n-butyl, sec-butyl, isobutyl, tert-butyl, n-pentyl, —C(=O)—OH, —C(=O)—O—CH$_3$, —C(=O)—O—C$_2$H$_5$, —C(=O)—O—CH(CH$_3$)$_2$, —C(=O)—O—C(CH$_3$)$_3$, —NH—CH$_3$, —NH—C$_2$H$_5$, —NH—C(CH$_3$)$_3$, —N(CH$_3$)$_2$, —N(C$_2$H$_5$)$_2$, —N(CH$_3$)—(C$_2$H$_5$), —NH—C(=O)—O—CH$_3$, —NH—C(=O)—O—C$_2$H$_5$, —NH—C(=O)—O—C(CH$_3$)$_3$, —C(=O)—H, —C(=O)—CH$_3$, —C(=O)—C$_2$H$_5$, —C(=O)—CH(CH$_3$)$_2$, —C(=O)—C(CH$_3$)$_3$, —C(=O)—NH$_2$, —C(=O)—NH—CH$_3$, —C(=O)-nH—C$_2$H$_5$, —C(=O)—N(CH$_3$)$_2$, —C(=O)—N(C$_2$H$_5$)$_2$, —O-phenyl, —O-benzyl, phenyl, and benzyl; and $R^{61}$ represents an alkyl group selected from the group consisting of —CF$_3$, —CH$_2$—CF$_3$, methyl, ethyl, n-propyl, isopropyl, tert-butyl, n-butyl, sec-butyl, and isobutyl;

or a salt thereof.

6. A compound according to claim 1, wherein:

n is 0, 1, or 2;

$R^1$ represents H; F; Cl; Br; I; —CF$_3$; —CN; —NH$_2$; —OH; —NH—C(=O)—R$^{13}$; —OR$^{16}$; —SR$^{17}$; —S(=O)—NR$^{22}$R$^{23}$; —S(=O)$_2$—R$^{27}$; methyl; —CF$_3$; —CHF$_2$; —CH$_2$F; ethyl; n-propyl; isopropyl; n-butyl; sec-butyl; isobutyl or tert-butyl;

$R^2$ represents H; F; Cl; Br; I; —CF$_3$; —CN; —NH$_2$; —OH; —NH—C(=O)—R$^{13}$; —OR$^{16}$; —SR$^{17}$; —S(=O)—NR$^{22}$R$^{23}$; —S(=O)$_2$—R$^{27}$; methyl; —CF$_3$; —CHF$_2$; —CH$_2$F; ethyl; n-propyl; isopropyl; n-butyl; sec-butyl; isobutyl or tert-butyl;

$R^3$ represents H; F; Cl; Br; I; —CF$_3$; —CN; —NH$_2$; —OH; —NH—C(=O)—R$^{13}$; —OR$^{16}$; —SR$^{17}$; —S(=O)$_2$—R$^{27}$; methyl; —CF$_3$; —CHF$_2$; —CH$_2$F; ethyl; n-propyl; isopropyl; n-butyl; sec-butyl; isobutyl or tert-butyl;

$R^4$ represents H; F; Cl; Br; I; —CF$_3$; —CN; —NH$_2$; —OH; —NH—C(=O)—R$^{13}$; —OR$^{16}$; —SR$^{17}$; —S(=O)—NR$^{22}$R$^{23}$; —S(=O)$_2$—R$^{27}$; methyl; —CF$_3$; —CHF$_2$; —CH$_2$F; ethyl; n-propyl; isopropyl; n-butyl; sec-butyl; isobutyl or tert-butyl;

$R^5$ represents H; F; Cl; Br; I; —CF$_3$; —CN; —NH$_2$; —OH; —NH—C(=O)—R$^{13}$; —OR$^{16}$; —SR$^{17}$; —S(=O)—NR$^{22}$R$^{23}$; —S(=O)$_2$—R$^{27}$; methyl; —CF$_3$; —CHF$_2$; —CH$_2$F; ethyl; n-propyl; isopropyl; n-butyl; sec-butyl; isobutyl or tert-butyl;

$R^6$ represents hydrogen or an alkyl group selected from the group consisting of isopropyl, n-butyl, sec-butyl, isobutyl, methyl, ethyl, and n-propyl;

$R^7$ represents hydrogen or —OH; or $R^6$ and $R^7$ together with the carbon atom to which they are attached form a cycloalkyl group selected from the group consisting of cyclopropyl, cyclobutyl, cyclopentyl, cyclohexyl, and cycloheptyl;

$R^8$ represents —CF$_3$; or tert-butyl;

T represents C—R$^{35}$; U represents C—R$^{36}$; V represents N, and W represents C—R$^{38}$;

$R^{13}$, $R^{16}$, $R^{17}$, $R^{22}$, $R^{23}$ and $R^{27}$ each independently represent a group selected from the group consisting of methyl, —CF$_3$, —CHF$_2$, —CH$_2$F, ethyl, —CF$_2$—CH$_3$, —CH$_2$—CF$_3$, —C$_2$F$_5$, n-propyl, isopropyl, n-butyl, sec-butyl, isobutyl, tert-butyl, n-pentyl, 3-pentyl, n-heptyl, 4-heptyl, n-octyl, n-nonyl, 5-nonyl, (2,6)-dimethylhept-4-yl, 3-methylbutyl, n-hexyl, (3,3)-dimethylbutyl, and ethenyl;

$R^{35}$, $R^{36}$, and $R^{37}$ each independently represent H; —SF$_5$; —NO$_2$; —CN; —NH$_2$; —OH; —SH; —OR$^{16}$; —SR$^{17}$; —CH$_2$—OH; methyl; —CF$_3$; —CHF$_2$; —CH$_2$F; ethyl; n-propyl; isopropyl; n-butyl; sec-butyl; isobutyl or tert-butyl;

$R^{38}$ represents —SF$_5$; —NO$_2$; —CN; —NH$_2$; —OH; —SH; —NHR$^{39}$; —NR$^{40}$R$^{41}$; —OR$^{42}$; —SR$^{43}$; or a group selected from the group consisting of cyclopropyl, cyclobutyl, cyclopentyl, cyclohexyl, cyclohexenyl, imidazolidinyl, tetrahydrofuranyl, tetrahydrothiophenyl, pyrrolidinyl, piperidinyl, morpholinyl, piperazinyl, azepanyl, diazepanyl, azocanyl, and thiomorpholinyl, each of which is bonded to the basic framework via a carbon atom of the rings thereof, and each of which may be unsubstituted or optionally substituted by 1, 2, 3, 4, or 5 substituents independently selected from the group consisting of —CH$_2$—N(CH$_3$)$_2$, —CH$_2$—N(C$_2$H$_5$)$_2$, —CH$_2$—NH—CH$_3$, —CH$_2$—NH—C$_2$H$_5$, —N—[C(=O)—C$_2$H$_5$]phenyl, —N—[C(=O)—CH$_3$]phenyl, methyl, ethyl, n-propyl, isopropyl, n-butyl, sec-butyl, isobutyl, and tert-butyl; or a group selected from the group consisting of phenyl, thiophenyl, furanyl, pyrrolyl, pyrazolyl, pyrazinyl, pyranyl, triazolyl, pyridinyl, imidazolyl, thiazolyl, oxazolyl, isoxazolyl, pyridazinyl, pyrazinyl, and pyrimidinyl, each of which optionally may be substituted by 1, 2, 3, 4, or 5 substituents independently selected from the group consisting of F, Cl, Br, I, —CN, —CF$_3$, —SF$_5$, —OH, —O—CH$_3$, —O—C$_2$H$_5$, —O—CH(CH$_3$)$_2$, —O—C(CH$_3$)$_3$, —O—CF$_3$, methyl, ethyl, n-propyl, isopropyl, n-butyl, sec-butyl, isobutyl, tert-butyl, and n-pentyl;

$R^{41}$, $R^{42}$, $R^{43}$, $R^{42}$, and $R^{43}$, each independently represent a group selected from the group consisting of methyl, —CH$_2$—O—CH$_3$, ethyl, n-propyl, n-butyl, sec-butyl, isobutyl, tert-butyl, n-pentyl, 3-pentyl, n-hexyl, (3,3)- dimethylbutyl, —CH$_2$—CH$_2$—O—CH$_3$, —CH$_2$—CH$_2$—O—C$_2$H$_5$, and —CH$_2$—CH$_2$—CH$_2$—O—CH$_3$; or a group selected from the group consisting of 2,3-dihydro-1H-indenyl, cyclopropyl, oxetanyl, cyclobutyl, cyclopentyl, cyclohexyl, imidazolidinyl, tetrahydrofuranyl, tetrahydrothiophenyl, pyrrolidinyl, piperidinyl, morpholinyl, piperazinyl, azepanyl, diazepanyl, azocanyl, and thiomorpholinyl, each of which optionally may be substituted by 1, 2, 3, 4, or 5 substituents independently selected from the group consisting of methyl, ethyl, n-propyl, isopropyl, n-butyl, sec-butyl, isobutyl, tert-butyl, and n-pentyl; or $R^{40}$ and $R^{41}$ together with the nitrogen atom to which they are attached form a group selected from the group consisting of 3-azabicyclo[3.1.1]heptyl, 6-azaspiro[2.5]octyl, 3-acabicyclo[3.2.1]octyl, 6-azabicyclo[3.3.1]heptyl, 8-acabicyclo[3.2.1]octyl, 1-oxa-2,8-diazaspiro[4.5]dec-2-enyl, azocanyl, isoindolyl, indolyl, (1,2,3,6)-tetrahydropyridinyl, (4,5,6,7)-tetrahydroisoxazolo[5.4-c]pyridinyl, pyrrolidinyl, piperidinyl, piperazinyl, morpholinyl, azepanyl, diazepanyl, and thiomorpholinyl, wherein the heterocycloaliphatic moiety may be unsubstituted or optionally substituted by 1, 2, 3, 4, or 5 groups $R^{57}$;

$R^{57}$ represents —NHR$^{58}$, —NR$^{59}$R$^{60}$, or an alkyl group selected from the group consisting of —CF$_3$, —CH$_2$—CF$_3$, methyl, ethyl, n-propyl, isopropyl, tert-butyl, n-butyl, sec-butyl, and isobutyl;

$R^{58}$, $R^{59}$, and $R^{60}$ each independently represent —C(=O)—R$^{61}$; or an alkyl group selected from the group consisting of —CF$_3$, —CH$_2$—CF$_3$, methyl, ethyl, n-propyl, isopropyl, tert-butyl, n-butyl, sec-butyl, and isobutyl; or an aromatic group selected from the group consisting of phenyl and naphthyl, wherein said aromatic group optionally may be bonded via a —(CH$_2$)—, —(CH$_2$)$_2$— or —(CH$_2$)$_3$— group, and may be unsubstituted or optionally substituted by 1, 2, 3, 4, or 5 substituents independently selected from the group consisting of F, Cl, Br, I, —CN, —CF$_3$, —O—CH$_3$, —O—C$_2$H$_5$, —O—CH(CH$_3$)$_2$, —O—C(CH$_3$)$_3$, methyl, ethyl, n-propyl, isopropyl, n-butyl, sec-butyl, isobutyl, tert-butyl, and n-pentyl; and $R^{61}$ represents an alkyl group selected from the group consisting of —CF$_3$, —CH$_2$—CF$_3$, methyl, ethyl, n-propyl, isopropyl, tert-butyl, n-butyl, sec-butyl, and isobutyl;

or a salt thereof.

7. A compound according to claim 1, wherein:

n is 0, 1, or 2;

$R^1$ represents H; F; Cl; Br; I; methyl, ethyl, —OH; —NH$_2$; —NH—C(=O)—R$^{13}$; —OR$^{16}$; —SR$^{17}$, —S(=O)$_2$—NR$^{22}$R$^{23}$, or —(S=O)—R$^{27}$;

$R^2$ represents H; F; Cl; Br; I; methyl, ethyl, —OH; —NH$_2$; —NH—C(=O)—R$^{13}$; —OR$^{16}$; —SR$^{17}$, —S(=O)$_2$—NR$^{22}$R$^{23}$, or —(S=O)—R$^{27}$;

$R^3$ represents H; F; Cl; Br; I; methyl, ethyl, —OH; —NH$_2$; —NH—C(=O)—R$^{13}$; —OR$^{16}$; —SR$^{17}$, -or —(S=O)—R$^{27}$;

$R^4$ represents H; F; Cl; Br; I; methyl, ethyl, —OH; —NH$_2$; —NH—C(=O)—R$^{13}$; —OR$^{16}$; —SR$^{17}$, —S(=O)$_2$—NR$^{22}$R$^{23}$, or —(S=O)—R$^{27}$;

$R^5$ represents H; F; Cl; Br; I; methyl, ethyl, —OH; —NH$_2$; —NH—C(=O)—R$^{13}$; —OR$^{16}$; —SR$^{17}$, —S(=O)$_2$—NR$^{22}$R$^{23}$, or —(S=O)—R$^{27}$;

$R^6$ represents hydrogen or an alkyl group selected from the group consisting of isopropyl, n-butyl, sec-butyl, isobutyl, methyl, ethyl, and n-propyl;

$R^7$ represents hydrogen or —OH;

$R^8$ represents —CF$_3$; or tert-butyl;

T represents C—R$^{35}$; U represents C—R$^{36}$; V represents N, and W represents C—R$^{38}$;

$R^{13}$, $R^{16}$, $R^{17}$, $R^{22}$, $R^{23}$ and $R^{27}$ each independently represent a group selected from the group consisting of methyl, ethyl, n-propyl, isopropyl, n-butyl, sec-butyl, isobutyl, tert-butyl, n-pentyl, and ethenyl;

$R^{35}$, $R^{36}$, and $R^{37}$ each represent H;

$R^{38}$ represents —NHR$^{39}$; —NR$^{40}$R$^{41}$; —OR$^{42}$; or —SR$^{43}$;

$R^{39}$, $R^{42}$, and $R^{43}$ each independently represent a group selected from the group consisting of methyl, ethyl, n-propyl, n-butyl, sec-butyl, isobutyl, tert-butyl, n-pentyl, 3-pentyl, n-hexyl, and (3,3)-dimethylbutyl; or a group selected from the group consisting of cyclopropyl, cyclobutyl, cyclopentyl, cyclohexyl, and cycloheptyl, each of which optionally may be substituted by 1, 2, 3, 4, or 5 substituents independently selected from the group consisting of methyl, ethyl, n-propyl, isopropyl, n-butyl, sec-butyl, isobutyl, tert-butyl, and n-pentyl;

$R^{40}$ and $R^{41}$ together with the nitrogen atom to which they are bound form a group selected from the group consisting of pyrrolidinyl, piperidinyl, piperazinyl, morpholinyl, and azepanyl, wherein the heterocycloaliphatic moiety may be unsubstituted or optionally substituted by 1, 2, 3, 4, or 5 groups $R^{57}$; and $R^{57}$ represents an alkyl group selected from the group consisting of methyl, ethyl, n-propyl, isopropyl, tert-butyl, n-butyl, sec-butyl, and isobutyl;

or a salt thereof.

8. A compound according to claim 1, wherein:

n is 1;

$R^1$ represents H; F; Cl; Br or I;

$R^2$ represents H; F; Cl; Br; I; methyl; —OH; —NH$_2$ or —OR$^{16}$;

$R^3$ represents H; F; Cl; Br; I; —OH; —NH$_2$; —NH—C(=O)—R$^{13}$, —OR$^{16}$; SR$^{17}$; or —S(=O)—R$^{27}$;

$R^4$ represents H; F; Cl; Br; I; methyl, —OH; —NH$_2$ or —OR$^{16}$;

$R^5$ represents H; F; Cl; Br or I;

$R^6$ represents hydrogen or an alkyl group selected from the group consisting of isopropyl, n-butyl, sec-butyl, isobutyl, methyl, ethyl, and n-propyl;

$R^7$ represents hydrogen or —OH;

$R^8$ represents —CF$_3$; or tert-butyl;

T represents C—R$^{35}$; U represents C—R$^{36}$; V represents N, and W represents C—R$^{38}$;

$R^{13}$, $R^{16}$, $R^{17}$, $R^{22}$, $R^{23}$ and $R^{27}$ each independently represent a group selected from the group consisting of methyl, ethyl, n-propyl, isopropyl, n-butyl, sec-butyl, isobutyl, tert-butyl, n-pentyl, and ethenyl;

$R^{35}$, $R^{36}$, and $R^{37}$ each represent H;

$R^{38}$ represents —NHR$^{39}$; —NR$^{40}$R$^{41}$; —OR$^{42}$; or —SR$^{43}$;

$R^{39}$, $R^{42}$, and $R^{43}$ each independently represent a group selected from the group consisting of methyl, ethyl, n-propyl, n-butyl, sec-butyl, isobutyl, tert-butyl, n-pentyl, 3-pentyl, n-hexyl, and (3,3)-dimethylbutyl; or a group selected from the group consisting of cyclopropyl, cyclobutyl, cyclopentyl, cyclohexyl, and cycloheptyl, each of which optionally may be substituted by 1, 2, 3, 4, or 5 substituents independently selected from the group consisting of methyl, ethyl, n-propyl, isopropyl, n-butyl, sec-butyl, isobutyl, tert-butyl, and n-pentyl;

$R^{40}$ and $R^{41}$ together with the nitrogen atom to which they are attached form a group selected from the group comprising the group consisting pyrrolidinyl, piperidinyl, piperazinyl, morpholinyl, and azepanyl, wherein the heterocycloaliphatic moiety may be unsubstituted or optionally substituted by 1, 2, 3, 4, or 5 groups $R^{57}$; and $R^{57}$ represents an alkyl group selected from the group consisting of methyl, ethyl, n-propyl, isopropyl, tert-butyl, n-butyl, sec-butyl, and isobutyl;

or a salt thereof.

9. A compound according to claim 6, corresponding to formula Ia:

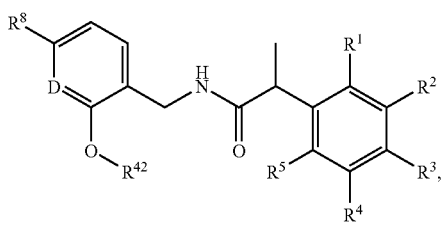

wherein

D represents N; and $R^1$, $R^2$, $R^3$, $R^4$, $R^5$, $R^8$, and $R^{42}$ have the respective meanings given in claim 6;

or a salt thereof.

10. A compound according to claim 7, corresponding to formula Ia:

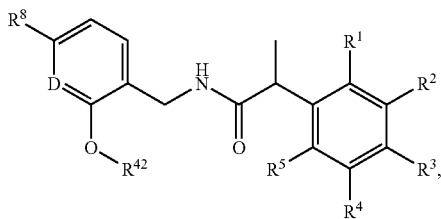

wherein

D represents N; and $R^1$, $R^2$, $R^3$, $R^4$, $R^5$, $R^8$, and $R^{42}$ have the respective meanings given in claim 7;

or a salt thereof.

11. A compound according to claim 8, corresponding to formula Ia:

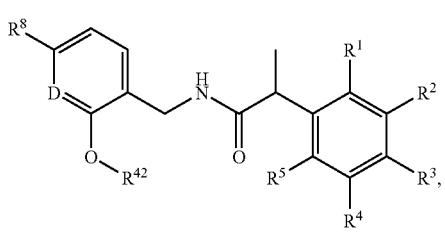

wherein

D represents N; and $R^1$, $R^2$, $R^3$, $R^4$, $R^5$, $R^8$, and $R^{42}$ have the respective meanings given in claim 8;

or a salt thereof.

12. A compound according to claim 6, corresponding to formula Ib:

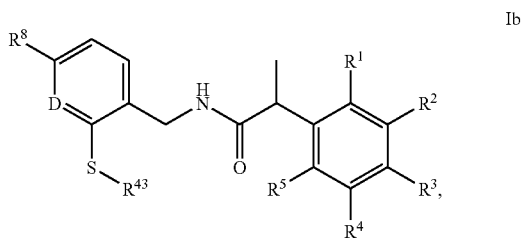

wherein

D represents N; and $R^1$, $R^2$, $R^3$, $R^4$, $R^5$, $R^8$, and $R^{42}$ have the respective meanings given in claim 3;

or a salt thereof.

13. A compound according to claim 7, corresponding to formula Ib:

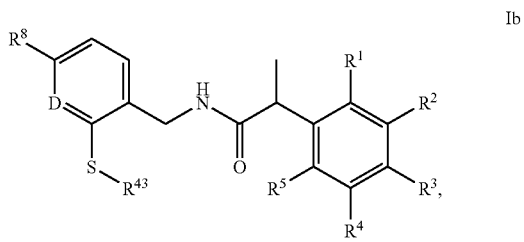

wherein

D represents N; and $R^1$, $R^2$, $R^3$, $R^4$, $R^5$, $R^8$, and $R^{42}$ have the respective meanings given in claim 7;

or a salt thereof.

14. A compound according to claim 8, corresponding to formula Ib:

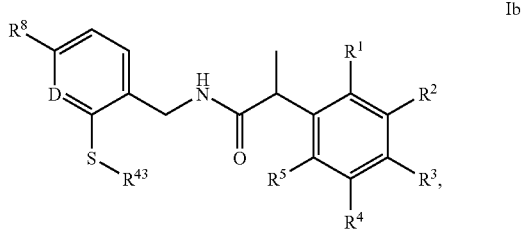

wherein

D represents N; and $R^1$, $R^2$, $R^3$, $R^4$, $R^5$, $R^8$, and $R^{42}$ have the respective meanings given in claim 8;

or a salt thereof.

15. A compound according to claim 6, corresponding to formula Ic:

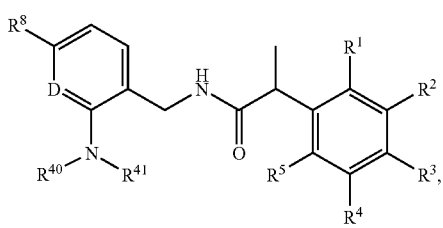

wherein
D represents N; and
R¹, R², R³, R⁴, R⁵, R⁸, and R⁴² have the respective meanings given in claim 6;
or a salt thereof.

16. A compound according to claim 7, corresponding to formula Ic:

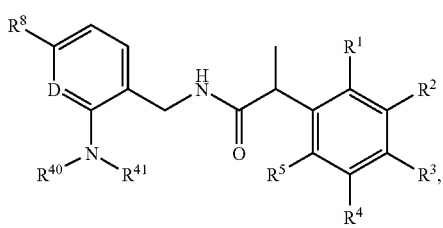

wherein
D represents N; and
R¹, R², R³, R⁴, R⁵, R⁸, and R⁴² have the respective meanings given in claim 7;
or a salt thereof.

17. A compound according to claim 8, corresponding to formula Ic:

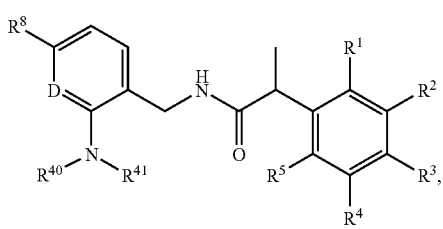

wherein
D represents N; and
R¹, R², R³, R⁴, R⁵, R⁸, and R⁴² have the respective meanings given in claim 8;
or a salt thereof.

18. A compound selected from the group consisting of:

[1] 2-(4-Amino-3-fluorophenyl)-N-((2-(4-methylpiperidin-1-yl)-6-(trifluoromethyl)pyridin-3-yl)methyl)propanamide,
[2] 2-(3,5-Dibromophenyl)-N-((2-(4-methylpiperidin-1-yl)-6-(trifluoromethyl)pyridin-3-yl)methyl)acetamide,
[3] 2-(4-Amino-3-bromo-5-methoxyphenyl)-N-((2-(4-methylpiperidin-1-yl)-6-(trifluoromethyl)pyridin-3-yl)methyl)acetamide,
[4] 2-(3-Fluorophenyl)-N-((2-(4-methylpiperidin-1-yl)-6-(trifluoromethyl)pyridin-3-yl)methyl)acetamide,
[5] 2-(2,4-Difluorophenyl)-N-((2-(4-methylpiperidin-1-yl)-6-(trifluoromethyl)pyridin-3-yl)methyl)acetamide,
[6] 2-(2,6-Difluorophenyl)-N-((2-(4-methylpiperidin-1-yl)-6-(trifluoromethyl)pyridin-3-yl)methyl)acetamide,
[7] 2-(2,5-Difluorophenyl)-N-((2-(4-methylpiperidin-1-yl)-6-(trifluoromethyl)pyridin-3-yl)methyl)acetamide,
[8] 2-(4-Fluorophenyl)-N-((2-(4-methylpiperidin-1-yl)-6-(trifluoromethyl)pyridin-3-yl)methyl)acetamide,
[9] 2-(4-Hydroxy-3-methoxyphenyl)-N-((2-(4-methylpiperidin-1-yl)-6-(trifluoromethyl)pyridin-3-yl)methyl)propanamide,
[10] 2-(3,5-Difluorophenyl)-N-((2-(4-methylpiperidin-1-yl)-6-(trifluoromethyl)pyridin-3-yl)methyl)propanamide,
[11] 2-(3,4-Difluorophenyl)-N-((2-(4-methylpiperidin-1-yl)-6-(trifluoromethyl)pyridin-3-yl)methyl)propanamide,
[12] 2-(4-Fluorophenyl)-N-((2-(4-methylpiperidin-1-yl)-6-(trifluoromethyl)pyridin-3-yl)methyl)propanamide,
[13] 2-(3-Fluorophenyl)-N-((2-(4-methylpiperidin-1-yl)-6-(trifluoromethyl)pyridin-3-yl)methyl)propanamide,
[14] 2-(3,4-Diaminophenyl)-N-((2-(4-methylpiperidin-1-yl)-6-(trifluoromethyl)pyridin-3-yl)methyl)propanamide,
[15] N-(2-Butoxy-6-tert-butylpyridin-3-ylmethyl)-2-(3,4-diamino-phenyl)-propanamide,
[16] N-((6-tert-Butyl-2-(4-methylpiperidin-1-yl)pyridin-3-yl)methyl)-2-(3,4-diaminophenyl)propanamide,
[17] N-((6-tert-Butyl-2-(cyclohexylthio)pyridin-3-yl)methyl)-2-(3,4-diaminophenyl)propanamide,
[18] 2-(4-Acetamido-3-fluorophenyl)-N-((2-(4-methylpiperidin-1-yl)-6-(trifluoromethyl)pyridin-3-yl)methyl)propanamide,
[19] 2-(3,5-Dibromo-4-hydroxyphenyl)-N-((2-(4-methylpiperidin-1-yl)-6-(trifluoromethyl)pyridin-3-yl)methyl)propanamide,
[20] 2-(4-Amino-3,5-dibromophenyl)-N-((2-(4-methylpiperidin-1-yl)-6-(trifluoromethyl)pyridin-3-yl)methyl)propanamide,
[21] 2-(3-Brom-4-hydroxy-5-methoxyphenyl)-N-((2-(4-methyl-piperidin-1-yl)-6-(trifluoromethyl)pyridin-3-yl)methyl)acetamide,
[22] 2-(4-Amino-3,5-dibromophenyl)-N-((2-(4-methylpiperidin-1-yl)-6-(trifluoromethyl)pyridin-3-yl)methyl)acetamide,
[23] 2-(3,5-Dibromo-4-hydroxyphenyl)-N-((2-(4-methylpiperidin-1-yl)-6-(trifluoromethyl)pyridin-3-yl)methyl)acetamide,
[24] 2-(3-Amino-4-hydroxyphenyl)-N-((2-(4-methylpiperidin-1-yl)-6-(trifluoromethyl)pyridin-3-yl)methyl)propanamide, and
[25] 2-(3,5-Dibromophenyl)-N-(4-methyl-6'-trifluoromethyl-3,4,5,6-tetrahydro-2H-[1,2']bipyridinyl-3'-ylmethyl)acetamide
[26] 2-(4-Amino-3,5-difluorophenyl)-N-((2-(4-methylpiperidin-1-yl)-6-(trifluoromethyl)pyridin-3-yl)methyl)propanamide,
[28] 2-(3-Chloro-4-(methylthio)phenyl)-N-((2-(4-methylpiperidin-1-yl)-6-(trifluoromethyl)pyridin-3-yl)methyl)propanamide,
[29] 2-(3-Chloro-4-(methylsulfonyl)phenyl)-N-((2-(4-methylpiperidin-1-yl)-6-(trifluoromethyl)pyridin-3-yl)methyl)propanamide,
[30] 2-(3-Fluoro-4-(methylthio)phenyl)-N-((2-(4-methylpiperidin-1-yl)-6-(trifluoromethyl)pyridin-3-yl)methyl)propanamide,
[31] 2-(3-Fluoro-4-(methylsulfonyl)phenyl)-N-((2-(4-methylpiperidin-1-yl)-6-(trifluoromethyl)pyridin-3-yl)methyl)propanamide,
[33] N-(2-Fluoro-4-(1-((2-(4-methylpiperidin-1-yl)-6-(trifluoromethyl)-pyridin-3-yl)methylamino)-1-oxopropan-2-yl)phenyl)acrylamide,
[34] N-(2-Fluoro-6-iodo-4-(1-((2-(4-methylpiperidin-1-yl)-6-(trifluoromethyl)-pyridin-3-yl)methylamino)-1-oxopropan-2-yl)phenyl)acrylamide,
[35] 2-(4-Methoxy-3,5-dimethylphenyl)-N-((2-(4-methylpiperidin-1-yl)-6-(trifluoromethyl)pyridin-3-yl)methyl)propanamide,
[36] 2-(3,5-Difluoro-4-methoxyphenyl)-N-((2-(4-methylpiperidin-1-yl)-6-(trifluoromethyl)pyridin-3-yl)methyl)propanamide,
[37] 2-(4-Hydroxy-3,5-dimethylphenyl)-N-((2-(4-methylpiperidin-1-yl)-6-(trifluoromethyl)pyridin-3-yl)methyl)propanamide, and
[38] 2-(3,5-Difluoro-4-hydroxyphenyl)-N-((2-(4-methylpiperidin-1-yl)-6-(trifluoromethyl)pyridin-3-yl)methyl)propanamide.

19. A compound according to claim 1, wherein, in the FLIPR assay using CHO-K1 cells transfected with a human VR1 gene, said compound in a concentration below 2000 nM, causes a 50 percent displacement of capsaicin present in a concentration of 100 nM.

20. A compound according to claim 19, wherein said compound in a concentration below 300 nM causes a 50 percent displacement of capsaicin present in a concentration of 100 nM.

21. A compound according to claim 20, wherein said compound in a concentration below 75 nM causes a 50 percent displacement of capsaicin present in a concentration of 100 nM.

22. A compound according to claim 21, wherein said compound in a concentration below 10 nM causes a 50 percent displacement of capsaicin present in a concentration of 100 nM.

23. A pharmaceutical composition comprising a compound according to claim 1, and at least one pharmaceutically acceptable carrier or adjuvant.

24. A process for producing a compound according to claim 1, said process comprising:

converting a compound corresponding to formula II:

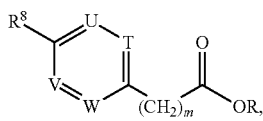

wherein
$R^8$, U, T, V and W have the meanings given in claim 1,
m is 0, 1, 2, or 3, and
R represents hydrogen or a linear or branched $C_{1-6}$ alkyl group,
in a reaction medium, in the presence of a reducing agent, to a compound of corresponding to formula III:

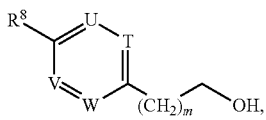

wherein
$R^8$, U, T, V, W and m have the meanings given above,
and optionally isolating or purifying the compound of formula III,
converting the compound of formula III,
in a reaction medium, and in the presence of diphenylphosphorylazide or of $HN_3$, to a compound corresponding to formula IV:

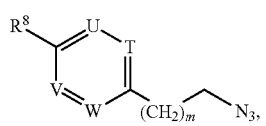

wherein
$R^8$, U, T, V, W and m have the meanings given above,
and optionally isolating or purifying the compound of formula IV,
converting the compound of formula IV in a reaction medium, and a) in the presence of a reducing agent, or
b) in the presence of a catalyst and of hydrogen or of hydrazine, or
c) in the presence of triphenylphosphine, to a compound corresponding to formula V:

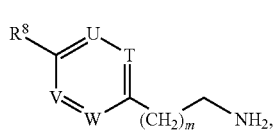

wherein
$R^8$, U, T, V, W and m have the respective meanings given above,
and optionally isolating or purifying the compound of formula V,
or
converting a compound corresponding to formula VI:

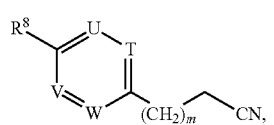

wherein
$R^8$, U, T, V, W and m have the respective meanings given above,
in a reaction medium,
a) in the presence of a catalyst under a blanket of hydrogen, optionally in the presence of an acid; or
b) in the presence of a reducing agent, optionally in the presence of $NiCl_2$, to form a compound corresponding to formula V or salt thereof,
and optionally isolating or purifying the compound of formula V,
reacting the compound corresponding to formula V
with a compound corresponding to formula VII:

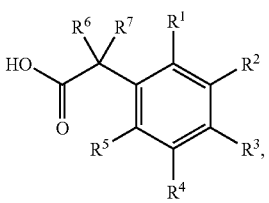

wherein
$R^1, R^2, R^3, R^4, R^5, R^6$, and $R^7$ have the respective meanings given in claim 1,
in a reaction medium, optionally in the presence of a coupling agent, and optionally in the presence of a base, or
with a compound corresponding to formula VIII:

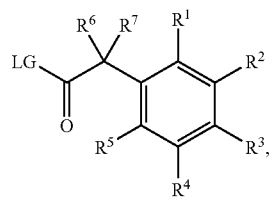

wherein $R^1, R^2, R^3, R^4, R^5, R^6$, and $R^7$ have the respective meanings given above, and LG represents a leaving group, in a reaction medium, optionally in the presence of a base, to yield a compound corresponding to formula I:

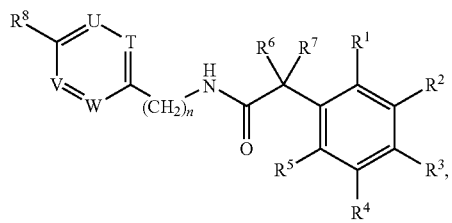

wherein

T, U, V, W, $R^1$, $R^2$, $R^3$, $R^4$, $R^5$, $R^6$, $R^7$, and $R^8$ have the respective meanings given above, and n is 1, 2, 3, or 4, and optionally isolating or purifying the compound of formula I.

25. A process according to claim 24, wherein:

a compound of formula II is reacted in the presence of a reducing agent selected from the group consisting of sodium hydride, sodium, potassium hydride, lithium aluminum hydride, sodium tetrahydridoborate, and di(isobutyl)aluminum hydride; or a compound of formula IV is converted in the presence of a reducing agent selected from the group consisting of sodium hydride, potassium hydride, lithium aluminum hydride, sodium tetrahydridoborate, and di(isobutyl)aluminum hydride; or the compound of formula IV is converted in the presence of a platinum or palladium catalyst; or a compound of formula VI is converted in the presence of a palladium or platinum catalyst and of hydrochloric acid; or a compound of formula VI is converted in the presence of a reducing agent selected from the group consisting of $BH_3$ bullet $S(CH_3)_2$, lithium aluminum hydride, and sodium tetrahydridoborate; or LG represents a chlorine or bromine atom.

26. A process for producing a compound according to claim 1, said process comprising:

reacting a compound corresponding to formula X:

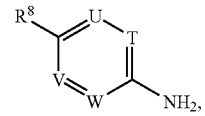

wherein $R^8$, U, T, V, and W have the respective meanings given in claim 1, with a compound corresponding to formula VII:

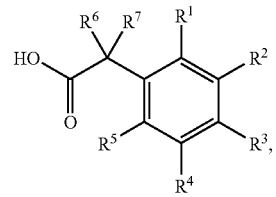

wherein $R^1, R^2, R^3, R^4, R^5, R^6$, and $R^7$, have the meanings given in claim 1, in a reaction medium, optionally in the presence of a coupling agent, and optionally in the presence of a base, or with a compound corresponding to formula VIII:

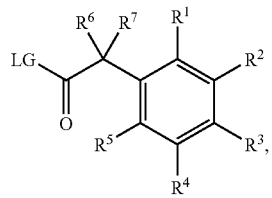

wherein $R^1, R^2, R^3, R^4, R^5, R^6$, and $R^7$ have the respective meanings given above, and LG represents a leaving group, in a reaction medium, optionally in the presence of a base, to form a compound corresponding to formula Im:

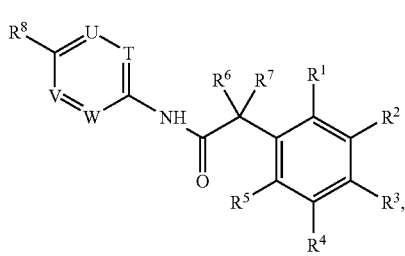

wherein

T, U, V, W, $R^1$, $R^2$, $R^3$, $R^4$, $R^5$, $R^6$, $R^7$, and $R^8$ have the respective meanings given above, and optionally isolating or purifying the compound of formula Im.

27. A method of treating or inhibiting pain in a subject, said method comprising administering to said subject a pharmacologically effective amount of a compound corresponding to formula I:

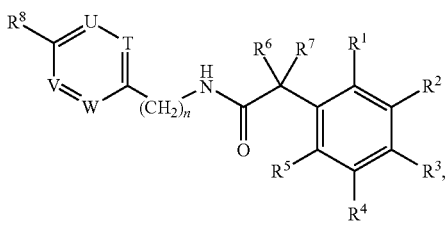

wherein
- n represents 1;
- $R^1$ represents H or F;
- $R^2$ represents H, F, Cl, Br, CN, $NH_2$, OH, $OR^{16}$, $CF_3$, or methyl;
- $R^3$ represents H, F, $CH=CH_2$, $NH_2$, OH, $C(=O)-NH_2$, $C(=NH)NH_2$, $NH-C(=O)-R^{13}$, $OR^{16}$, $SR^{17}$, $C(=O)-NHR^{18}$, $C(=O)R^{25}$, $S(=O)_2-R^{27}$; $CF_3$; or a methyl or ethyl radical which may be substituted by 1 or 2 substituents independently selected from the group consisting of OH, $NH_2$, $NHCH_3$, and $N(CH_3)_2$;
- $R^4$ represents H, F, Br, I, or methyl;
- $R^5$ represents H or F;
- $R^6$ represents H, or a linear or branched, saturated, unsubstituted aliphatic $C_{1-10}$ group;
- $R^7$ represents H;
- $R^8$ represents $CF_3$ or an unsubstituted tert-butyl group;
- T represents $CR^{35}$;
- U represents $CR^{36}$;
- V represents N or $CR^{37}$;
- W represents $CR^{38}$;
- $R^{13}$ represents phenyl, vinyl, or methyl;
- $R^{16}$ represents methyl;
- $R^{17}$ represents methyl;
- $R^{18}$ represents a methyl group; a phenyl group, wherein said phenyl group may be substituted by 1 substituent independently selected from the group consisting of F, Cl, and $CF_3$; 2 pyridinyl; thiazolyl; or tetrahydro-2H-pyranyl;
- $R^{25}$ represents methyl;
- $R^{27}$ represents methyl;
- $R^{35}$ represents H;
- $R^{36}$ represents H;
- $R^{37}$ represents H;
- $R^{38}$ represents n-propyl, which may be substituted by 1 $OCH_3$ group; a phenyl group, wherein said phenyl group may be substituted by 1 or 2 substituents independently selected from the group consisting of F, Cl, O—($C_{1-5}$-alkyl), ($C_{1-5}$-alkyl), $CH_2$-cyclohexyl, cyclohexyl, and cyclopentyl; $NHR^{39}$; $NR^{40}R^{41}$; $OR^{42}$; or S—$R^{43}$;
- $R^{39}$ represents n-butyl;
- $R^{40}$ and $R^{41}$ together with the nitrogen atom to which they are attached form a piperidinyl, pyrrolidinyl or morpholinyl group, which is unsubstituted or substituted by 1, 2 or 3 groups $R^{57}$;
- $R^{42}$ represents n-butyl, cyclohexyl, or cyclopentyl;
- $R^{43}$ represents cyclohexyl;
- $R^{57}$ represents $NR^{59}R^{60}$ or a methyl group;
- $R^{59}$ represents a methyl group; and
- $R^{60}$ represents a methyl group.

28. A method according to claim 27, wherein said pain is selected from the group consisting of acute pain, chronic pain, neuropathic pain and visceral pain; arthralgia; hyperalgesia; allodynia; causalgia; and migraine.

* * * * *